US007884086B2

(12) United States Patent
Bennett et al.

(10) Patent No.: US 7,884,086 B2
(45) Date of Patent: Feb. 8, 2011

(54) CONJUGATES FOR USE IN HEPATOCYTE FREE UPTAKE ASSAYS

(75) Inventors: C. Frank Bennett, Carlsbad, CA (US); Robert McKay, Poway, CA (US); Brett P. Monia, Encinitas, CA (US); Brenda F. Baker, Carlsbad, CA (US); Namir Sioufi, Beirut (LB)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 11/221,001

(22) Filed: Sep. 7, 2005

(65) Prior Publication Data

US 2006/0084094 A1 Apr. 20, 2006

Related U.S. Application Data

(60) Provisional application No. 60/608,482, filed on Sep. 8, 2004.

(51) Int. Cl.
*A61K 31/70* (2006.01)
*C07H 21/04* (2006.01)
(52) U.S. Cl. .................. 514/44; 536/23.1; 536/24.5
(58) Field of Classification Search .................. None
See application file for complete search history.

(56) References Cited

U.S. PATENT DOCUMENTS

| | | |
|---|---|---|
| 3,687,808 A | 8/1972 | Merigan et al. |
| 4,373,071 A | 2/1983 | Itakura |
| 4,381,344 A | 4/1983 | Rideout et al. |
| 4,401,796 A | 8/1983 | Itakura |
| 4,415,732 A | 11/1983 | Caruthers et al. |
| 4,426,330 A | 1/1984 | Sears |
| 4,458,066 A | 7/1984 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,507,433 A | 3/1985 | Miller et al. |
| 4,511,713 A | 4/1985 | Miller et al. |
| 4,534,899 A | 8/1985 | Sears |
| 4,587,044 A | 5/1986 | Miller |
| 4,605,735 A | 8/1986 | Miyoshi |
| 4,667,025 A | 5/1987 | Miyoshi |
| 4,668,777 A | 5/1987 | Caruthers et al. |
| 4,689,320 A | 8/1987 | Kaji |
| 4,720,483 A | 1/1988 | Jansz et al. |
| 4,725,677 A | 2/1988 | Koster et al. |
| 4,757,141 A | 7/1988 | Fung et al. |
| 4,760,017 A | 7/1988 | McCormick |
| 4,762,779 A | 8/1988 | Snitman |
| 4,789,737 A | 12/1988 | Miyoshi |
| 4,812,512 A | 3/1989 | Buendia et al. |
| 4,824,941 A | 4/1989 | Gordon |
| 4,828,979 A | 5/1989 | Klevan |
| 4,835,263 A | 5/1989 | Nguyen |
| 4,845,205 A | 7/1989 | Huynh Dinh et al. |
| 4,849,320 A | 7/1989 | Irving et al. |
| 4,849,513 A | 7/1989 | Smith et al. |
| 4,876,335 A | 10/1989 | Yamane |
| 4,904,582 A | 2/1990 | Tullis |
| 4,908,405 A | 3/1990 | Bayer et al. |
| 4,924,624 A | 5/1990 | Suhadolnik et al. |
| 4,948,882 A | 8/1990 | Ruth |
| 4,958,013 A | 9/1990 | Letsinger |
| 4,965,350 A | 10/1990 | Inoue et al. |
| 4,973,679 A | 11/1990 | Caruthers et al. |
| 4,981,957 A | 1/1991 | Lebleu |
| 5,000,000 A | 3/1991 | Ingram et al. |
| 5,013,556 A | 5/1991 | Woodle et al. |
| 5,013,830 A | 5/1991 | Ohtsuka et al. |
| 5,023,243 A | 6/1991 | Tullis |
| 5,034,506 A | 7/1991 | Summerton et al. |
| 5,082,830 A | 1/1992 | Brakel |
| 5,082,934 A | 1/1992 | Saba et al. |
| 5,108,921 A | 4/1992 | Low et al. |
| 5,109,124 A | 4/1992 | Ramathandran |
| 5,112,963 A | 5/1992 | Pieles |
| 5,118,800 A | 6/1992 | Smith et al. |
| 5,118,802 A | 6/1992 | Smith |
| 5,130,302 A | 7/1992 | Spielvogel et al. |
| 5,132,418 A | 7/1992 | Caruthers et al. |
| 5,134,066 A | 7/1992 | Rogers et al. |
| 5,138,045 A | 8/1992 | Cook |
| 5,142,047 A | 8/1992 | Summerton et al. |
| RE34,069 E | 9/1992 | Koster et al. |
| 5,149,782 A | 9/1992 | Chang et al. |
| 5,149,797 A | 9/1992 | Pederson et al. |
| 5,151,510 A | 9/1992 | Stec et al. |
| 5,166,315 A | 11/1992 | Summerton et al. |

(Continued)

FOREIGN PATENT DOCUMENTS

CA     2017369 C     1/2001

(Continued)

OTHER PUBLICATIONS

Branda et al. (1996) J. Lab. Clin. Med. 128:329-338.*

(Continued)

*Primary Examiner*—Tracy Vivlemore
(74) *Attorney, Agent, or Firm*—Isis Patent Department Woodcock Washburn LLP

(57) ABSTRACT

The present invention provides methods of identifying oligomeric compounds, such as siRNA and double-stranded RNA compounds, having bioactivity in vivo, and kits.

17 Claims, 8 Drawing Sheets

U.S. PATENT DOCUMENTS

| | | | |
|---|---|---|---|
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,212,295 A | 5/1993 | Cook |
| 5,213,804 A | 5/1993 | Martin et al. |
| 5,214,134 A | 5/1993 | Weis et al. |
| 5,214,135 A | 5/1993 | Srivastava et al. |
| 5,214,136 A | 5/1993 | Lin |
| 5,216,141 A | 6/1993 | Benner |
| 5,218,105 A | 6/1993 | Cook |
| 5,220,007 A | 6/1993 | Pederson |
| 5,223,618 A | 6/1993 | Cook et al. |
| 5,227,170 A | 7/1993 | Sullivan |
| 5,235,033 A | 8/1993 | Summerton et al. |
| 5,245,022 A | 9/1993 | Weis |
| 5,254,469 A | 10/1993 | Warren |
| 5,256,775 A | 10/1993 | Froehler |
| 5,258,506 A | 11/1993 | Urdea |
| 5,262,536 A | 11/1993 | Hobbs |
| 5,264,221 A | 11/1993 | Tagawa et al. |
| 5,264,423 A | 11/1993 | Cohen et al. |
| 5,264,562 A | 11/1993 | Matteucci |
| 5,264,564 A | 11/1993 | Matteucci |
| 5,272,250 A | 12/1993 | Spielvogel |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita |
| 5,317,098 A | 5/1994 | Shizuya |
| 5,319,080 A | 6/1994 | Leumann |
| 5,321,131 A | 6/1994 | Agrawal et al. |
| 5,354,844 A | 10/1994 | Beug et al. |
| 5,356,633 A | 10/1994 | Woodle et al. |
| 5,359,044 A | 10/1994 | Cook et al. |
| 5,366,878 A | 11/1994 | Pederson et al. |
| 5,367,066 A | 11/1994 | Urdea et al. |
| 5,371,241 A | 12/1994 | Brush |
| 5,378,825 A | 1/1995 | Cook et al. |
| 5,386,023 A | 1/1995 | Sanghvi et al. |
| 5,391,667 A | 2/1995 | Dellinger |
| 5,391,723 A | 2/1995 | Priest |
| 5,393,878 A | 2/1995 | Leumann |
| 5,395,619 A | 3/1995 | Zalipsky et al. |
| 5,399,676 A | 3/1995 | Froehler et al. |
| 5,403,711 A | 4/1995 | Walder et al. |
| 5,405,938 A | 4/1995 | Summerton et al. |
| 5,405,939 A | 4/1995 | Suhadolnik et al. |
| 5,414,077 A | 5/1995 | Lin |
| 5,416,016 A | 5/1995 | Low et al. |
| 5,416,203 A | 5/1995 | Letsinger |
| 5,417,978 A | 5/1995 | Tari et al. |
| 5,424,413 A | 6/1995 | Hogan et al. |
| 5,432,272 A | 7/1995 | Benner |
| 5,434,257 A | 7/1995 | Matteucci et al. |
| 5,446,137 A | 8/1995 | Maag |
| 5,451,463 A | 9/1995 | Nelson |
| 5,453,496 A | 9/1995 | Caruthers et al. |
| 5,455,233 A | 10/1995 | Spielvogel et al. |
| 5,457,187 A | 10/1995 | Gmeiner et al. |
| 5,457,191 A | 10/1995 | Cook et al. |
| 5,459,127 A | 10/1995 | Felgner et al. |
| 5,459,255 A | 10/1995 | Cook et al. |
| 5,462,854 A | 10/1995 | Coassin et al. |
| 5,466,677 A | 11/1995 | Baxter et al. |
| 5,466,786 A | 11/1995 | Buhr et al. |
| 5,469,854 A | 11/1995 | Unger et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,491,133 A | 2/1996 | Walder |
| 5,502,177 A | 3/1996 | Matteucci et al. |
| 5,506,212 A | 4/1996 | Hoke et al. |
| 5,506,337 A | 4/1996 | Summerton et al. |
| 5,506,351 A | 4/1996 | McGee |
| 5,508,270 A | 4/1996 | Baxter et al. |
| 5,510,475 A | 4/1996 | Agrawal |
| 5,512,295 A | 4/1996 | Kornberg et al. |
| 5,512,439 A | 4/1996 | Hornes |
| 5,512,667 A | 4/1996 | Reed |
| 5,514,785 A | 5/1996 | Van Ness |
| 5,514,786 A | 5/1996 | Cook et al. |
| 5,519,126 A | 5/1996 | Hecht |
| 5,519,134 A | 5/1996 | Acevedo et al. |
| 5,521,291 A | 5/1996 | Curiel et al. |
| 5,525,465 A | 6/1996 | Haralambidis |
| 5,525,711 A | 6/1996 | Hawkins et al. |
| 5,527,528 A | 6/1996 | Allen et al. |
| 5,527,899 A | 6/1996 | Froehler |
| 5,532,130 A | 7/1996 | Alul |
| 5,534,259 A | 7/1996 | Zalipsky et al. |
| 5,536,821 A | 7/1996 | Agrawal et al. |
| 5,539,082 A | 7/1996 | Nielsen et al. |
| 5,539,083 A | 7/1996 | Cook et al. |
| 5,541,306 A | 7/1996 | Agrawal et al. |
| 5,541,307 A | 7/1996 | Cook et al. |
| 5,541,313 A | 7/1996 | Ruth |
| 5,543,152 A | 8/1996 | Webb et al. |
| 5,543,158 A | 8/1996 | Gref et al. |
| 5,545,730 A | 8/1996 | Urdea |
| 5,547,932 A | 8/1996 | Curiel et al. |
| 5,550,111 A | 8/1996 | Suhadolnik et al. |
| 5,552,538 A | 9/1996 | Urdea |
| 5,552,540 A | 9/1996 | Haralambidis |
| 5,556,948 A | 9/1996 | Tagawa et al. |
| 5,561,043 A | 10/1996 | Cantor et al. |
| 5,561,225 A | 10/1996 | Maddry et al. |
| 5,563,253 A | 10/1996 | Agrawal et al. |
| 5,565,350 A | 10/1996 | Kmiec |
| 5,565,552 A | 10/1996 | Magda |
| 5,565,555 A | 10/1996 | Froehler et al. |
| 5,567,810 A | 10/1996 | Weis |
| 5,567,811 A | 10/1996 | Misiura et al. |
| 5,571,799 A | 11/1996 | Tkachuk et al. |
| 5,574,142 A | 11/1996 | Meyer |
| 5,576,302 A | 11/1996 | Cook et al. |
| 5,576,427 A | 11/1996 | Cook et al. |
| 5,578,717 A | 11/1996 | Urdea |
| 5,578,718 A | 11/1996 | Cook |
| 5,580,575 A | 12/1996 | Unger et al. |
| 5,580,731 A | 12/1996 | Chang |
| 5,582,188 A | 12/1996 | Benderev et al. |
| 5,583,020 A | 12/1996 | Sullivan |
| 5,585,481 A | 12/1996 | Arnold |
| 5,587,361 A | 12/1996 | Cook et al. |
| 5,587,371 A | 12/1996 | Sessler |
| 5,587,469 A | 12/1996 | Cook et al. |
| 5,591,584 A | 1/1997 | Chang |
| 5,591,721 A | 1/1997 | Agrawal et al. |
| 5,591,722 A | 1/1997 | Montgomery et al. |
| 5,594,121 A | 1/1997 | Froehler et al. |
| 5,595,726 A | 1/1997 | Magda |
| 5,595,756 A | 1/1997 | Bally et al. |
| 5,596,086 A | 1/1997 | Matteucci et al. |
| 5,596,091 A | 1/1997 | Switzer et al. |
| 5,597,696 A | 1/1997 | Linn |
| 5,597,909 A | 1/1997 | Urdea |
| 5,599,797 A | 2/1997 | Cook et al. |
| 5,599,923 A | 2/1997 | Sessler |
| 5,599,925 A | 2/1997 | Torii |

| Patent | Date | Inventors | Patent | Date | Inventors |
|---|---|---|---|---|---|
| 5,599,928 A | 2/1997 | Hemmi et al. | 5,808,023 A | 9/1998 | Sanghvi et al. |
| 5,602,240 A | 2/1997 | De Mesmaeker et al. | 5,808,036 A | 9/1998 | Kool |
| 5,607,922 A | 3/1997 | De Clercq et al. | 5,817,781 A | 10/1998 | Swaminathan et al. |
| 5,607,923 A | 3/1997 | Cook et al. | 5,830,635 A | 11/1998 | Agnello |
| 5,608,046 A | 3/1997 | Cook | 5,830,653 A | 11/1998 | Froehler et al. |
| 5,610,289 A | 3/1997 | Cook et al. | 5,837,835 A | 11/1998 | Gryaznov et al. |
| 5,610,300 A | 3/1997 | Altmann | 5,837,852 A | 11/1998 | Chung et al. |
| 5,612,469 A | 3/1997 | Goodchild | 5,840,876 A | 11/1998 | Beigelman et al. |
| 5,614,617 A | 3/1997 | Cook et al. | 5,854,410 A | 12/1998 | Arnold, Jr. et al. |
| 5,614,621 A | 3/1997 | Ravikumar et al. | 5,859,221 A | 1/1999 | Cook et al. |
| 5,618,704 A | 4/1997 | Sanghvi et al. | 5,861,493 A | 1/1999 | Cook et al. |
| 5,623,065 A | 4/1997 | Cook et al. | 5,872,232 A | 2/1999 | Cook et al. |
| 5,623,070 A | 4/1997 | Cook et al. | 5,874,553 A | 2/1999 | Peyman et al. |
| 5,625,050 A | 4/1997 | Beaton et al. | 5,891,683 A | 4/1999 | Usman et al. |
| 5,627,053 A | 5/1997 | Usman | 5,891,684 A | 4/1999 | Usman et al. |
| 5,631,148 A | 5/1997 | Urdea | 5,898,031 A | 4/1999 | Crooke |
| 5,633,360 A | 5/1997 | Bischofberger et al. | 5,914,396 A | 6/1999 | Cook et al. |
| 5,634,488 A | 6/1997 | Martin, Jr. | 5,936,080 A | 8/1999 | Stec et al. |
| 5,635,488 A | 6/1997 | Cook et al. | 5,945,521 A | 8/1999 | Just et al. |
| 5,639,647 A | 6/1997 | Usman et al. | 5,955,443 A | 9/1999 | Bennett et al. |
| 5,639,873 A | 6/1997 | Barascut et al. | 5,962,425 A | 10/1999 | Walder et al. |
| 5,643,889 A | 7/1997 | Suhadolnik et al. | 5,965,720 A | 10/1999 | Gryaznov et al. |
| 5,645,985 A | 7/1997 | Froehler et al. | 5,965,721 A | 10/1999 | Cook et al. |
| 5,646,265 A | 7/1997 | Mcgee | 5,969,116 A | 10/1999 | Martin |
| 5,646,269 A | 7/1997 | Matteucci et al. | 5,969,118 A | 10/1999 | Sanghvi et al. |
| 5,652,355 A | 7/1997 | Metelev | 5,986,083 A | 11/1999 | Dwyer et al. |
| 5,652,356 A | 7/1997 | Agrawal | 5,998,203 A | 12/1999 | Matulic-Adamic et al. |
| 5,658,731 A | 8/1997 | Sproat et al. | 5,998,588 A | 12/1999 | Hoffman et al. |
| 5,658,873 A | 8/1997 | Bertsch-Frank | 6,001,841 A | 12/1999 | Cook et al. |
| 5,661,134 A | 8/1997 | Cook et al. | 6,005,087 A | 12/1999 | Cook et al. |
| 5,663,312 A | 9/1997 | Chaturvedula | 6,005,094 A | 12/1999 | Simon et al. |
| 5,663,360 A | 9/1997 | Bortolaso et al. | 6,005,096 A | 12/1999 | Matteucci et al. |
| 5,670,633 A | 9/1997 | Cook et al. | 6,007,992 A | 12/1999 | Lin et al. |
| 5,672,662 A | 9/1997 | Harris et al. | 6,013,785 A | 1/2000 | Bruice et al. |
| 5,672,695 A | 9/1997 | Eckstein et al. | 6,015,886 A | 1/2000 | Dale et al. |
| 5,672,697 A | 9/1997 | Buhr et al. | 6,020,475 A | 2/2000 | Capaldi et al. |
| 5,677,289 A | 10/1997 | Torrence et al. | 6,025,140 A | 2/2000 | Langel et al. |
| 5,677,437 A | 10/1997 | Teng et al. | 6,028,188 A | 2/2000 | Arnold, Jr. et al. |
| 5,677,439 A | 10/1997 | Weis et al. | 6,033,910 A | 3/2000 | Monia et al. |
| 5,681,940 A | 10/1997 | Wang et al. | 6,037,463 A | 3/2000 | Uhlmann et al. |
| 5,681,941 A | 10/1997 | Cook et al. | 6,043,060 A | 3/2000 | Imanishi |
| 5,684,142 A | 11/1997 | Mishra et al. | 6,043,352 A | 3/2000 | Manoharan et al. |
| 5,684,143 A | 11/1997 | Gryaznov et al. | 6,046,306 A | 4/2000 | Breipohl et al. |
| 5,684,243 A | 11/1997 | Gururaja et al. | 6,051,699 A | 4/2000 | Ravikumar |
| 5,688,941 A | 11/1997 | Cook | 6,087,484 A | 7/2000 | Goodchild |
| 5,698,687 A | 12/1997 | Eckstein et al. | 6,096,875 A | 8/2000 | Khan et al. |
| 5,700,785 A | 12/1997 | Suhadolnik et al. | 6,107,094 A | 8/2000 | Crooke |
| 5,700,920 A | 12/1997 | Altmann | 6,111,085 A | 8/2000 | Cook et al. |
| 5,700,922 A | 12/1997 | Cook | 6,117,657 A | 9/2000 | Usman et al. |
| 5,714,166 A | 2/1998 | Tomalia et al. | 6,121,437 A | 9/2000 | Guzaev et al. |
| 5,714,331 A | 2/1998 | Buchardt et al. | 6,127,346 A | 10/2000 | Peyman et al. |
| 5,716,824 A | 2/1998 | Beigelman et al. | 6,127,533 A | 10/2000 | Cook et al. |
| 5,719,262 A | 2/1998 | Buchardt et al. | 6,133,246 A | 10/2000 | McKay et al. |
| 5,719,271 A | 2/1998 | Cook et al. | 6,147,200 A | 11/2000 | Manoharan et al. |
| 5,721,218 A | 2/1998 | Froehler et al. | 6,150,510 A | 11/2000 | Seela et al. |
| 5,726,297 A | 3/1998 | Gryaznov et al. | 6,153,737 A | 11/2000 | Manoharan et al. |
| 5,750,666 A | 5/1998 | Caruthers et al. | 6,166,188 A | 12/2000 | Cook et al. |
| 5,750,669 A | 5/1998 | Rosch et al. | 6,169,177 B1 | 1/2001 | Manoharan |
| 5,750,692 A | 5/1998 | Cook et al. | 6,172,208 B1 | 1/2001 | Cook |
| 5,760,202 A | 6/1998 | Cook et al. | 6,172,209 B1 | 1/2001 | Manoharan et al. |
| 5,760,209 A | 6/1998 | Cheruvallath et al. | 6,172,216 B1 | 1/2001 | Bennett et al. |
| 5,763,588 A | 6/1998 | Matteucci et al. | 6,207,646 B1 * | 3/2001 | Krieg et al. ............... 514/44 |
| 5,770,713 A | 6/1998 | Imbach et al. | 6,210,892 B1 | 4/2001 | Bennett et al. |
| 5,770,716 A | 6/1998 | Khan et al. | 6,222,025 B1 | 4/2001 | Cook et al. |
| 5,777,092 A | 7/1998 | Cook et al. | 6,227,982 B1 | 5/2001 | Wurster |
| 5,780,607 A | 7/1998 | Goodnow, Jr. et al. | 6,239,265 B1 | 5/2001 | Cook |
| 5,789,576 A | 8/1998 | Daily et al. | 6,239,272 B1 | 5/2001 | Beigelman et al. |
| 5,792,608 A | 8/1998 | Swaminathan et al. | 6,262,036 B1 | 7/2001 | Arnold, Jr. et al. |
| 5,792,747 A | 8/1998 | Schally | 6,262,241 B1 | 7/2001 | Cook et al. |
| 5,792,844 A | 8/1998 | Sanghvi et al. | 6,268,490 B1 | 7/2001 | Imanishi et al. |
| 5,792,847 A | 8/1998 | Buhr et al. | 6,271,358 B1 | 8/2001 | Manoharan et al. |
| 5,801,154 A | 9/1998 | Baracchini et al. | 6,274,723 B1 | 8/2001 | Nilsen |
| 5,804,683 A | 9/1998 | Usman et al. | 6,277,634 B1 * | 8/2001 | McCall et al. ............... 435/325 |

| | | |
|---|---|---|
| 6,277,967 B1 | 8/2001 | Manoharan |
| 6,281,201 B1 | 8/2001 | Suhadolnik et al. |
| 6,284,538 B1 | 9/2001 | Monia et al. |
| 6,287,860 B1 | 9/2001 | Monia et al. |
| 6,294,522 B1 | 9/2001 | Zablocki et al. |
| 6,300,319 B1 | 10/2001 | Manoharan |
| 6,307,040 B1 | 10/2001 | Cook et al. |
| 6,326,358 B1 | 12/2001 | Manoharan |
| 6,326,478 B1 | 12/2001 | Cheruvallath et al. |
| 6,329,346 B1 | 12/2001 | Muhlegger et al. |
| 6,331,617 B1 | 12/2001 | Weeks et al. |
| 6,335,432 B1 | 1/2002 | Segev |
| 6,335,434 B1 | 1/2002 | Guzaev et al. |
| 6,335,437 B1 | 1/2002 | Manoharan et al. |
| 6,344,436 B1 | 2/2002 | Smith et al. |
| 6,358,931 B1 | 3/2002 | Cook et al. |
| 6,365,379 B1 | 4/2002 | Lima et al. |
| 6,380,169 B1 | 4/2002 | Adams et al. |
| 6,395,437 B1 | 5/2002 | Wollesen |
| 6,395,474 B1 | 5/2002 | Buchardt et al. |
| 6,395,492 B1 | 5/2002 | Manoharan et al. |
| 6,410,702 B1 | 6/2002 | Swaminathan et al. |
| 6,414,127 B1 | 7/2002 | Lin et al. |
| 6,420,549 B1 | 7/2002 | Cook et al. |
| 6,426,220 B1 | 7/2002 | Bennett et al. |
| 6,436,640 B1 | 8/2002 | Simmons et al. |
| 6,440,943 B1 | 8/2002 | Cook et al. |
| 6,444,806 B1 | 9/2002 | Veerapanani et al. |
| 6,465,628 B1 | 10/2002 | Ravikumar et al. |
| 6,476,205 B1 | 11/2002 | Buhr et al. |
| 6,486,308 B2 | 11/2002 | Kutyavin et al. |
| 6,506,559 B1 | 1/2003 | Fire et al. |
| 6,525,031 B2 | 2/2003 | Manoharan |
| 6,528,631 B1 | 3/2003 | Cook et al. |
| 6,531,584 B1 | 3/2003 | Cook et al. |
| 6,534,639 B1 | 3/2003 | Manoharan et al. |
| 6,559,279 B1 | 5/2003 | Manoharan et al. |
| 6,573,072 B1 | 6/2003 | Goodchild |
| 6,593,466 B1 | 7/2003 | Manoharan et al. |
| 6,656,730 B1 | 12/2003 | Manoharan |
| 6,670,461 B1 | 12/2003 | Wengel et al. |
| 6,673,611 B2 | 1/2004 | Thompson et al. |
| 6,683,167 B2 | 1/2004 | Metelev et al. |
| 6,794,499 B2 | 9/2004 | Wengel et al. |
| 6,818,759 B2 | 11/2004 | Beigelman et al. |
| 6,849,726 B2 | 2/2005 | Usman et al. |
| 6,887,906 B1 | 5/2005 | Teng et al. |
| 7,022,828 B2 | 4/2006 | McSwiggen |
| 2002/0049173 A1 | 4/2002 | Bennett et al. |
| 2002/0068708 A1 | 6/2002 | Wengel et al. |
| 2002/0071826 A1* | 6/2002 | Tamarkin et al. .......... 424/85.1 |
| 2002/0081577 A1 | 6/2002 | Kilkuskie et al. |
| 2002/0081736 A1 | 6/2002 | Conroy et al. |
| 2002/0102267 A1 | 8/2002 | Lu et al. |
| 2002/0132788 A1 | 9/2002 | Lewis et al. |
| 2002/0147332 A1 | 10/2002 | Kaneko |
| 2002/0156235 A1 | 10/2002 | Manoharan et al. |
| 2002/0160393 A1 | 10/2002 | Symonds et al. |
| 2002/0162126 A1 | 10/2002 | Beach et al. |
| 2002/1051512 | 10/2002 | Peyman et al. |
| 2002/0165189 A1 | 11/2002 | Crooke |
| 2003/0004325 A1 | 1/2003 | Cook et al. |
| 2003/0027780 A1 | 2/2003 | Hardee et al. |
| 2003/0096286 A1 | 5/2003 | Crooke |
| 2003/0096287 A1 | 5/2003 | Crooke |
| 2003/0096784 A1 | 5/2003 | Crooke |
| 2003/0119777 A1 | 6/2003 | Crooke |
| 2003/0125241 A1 | 7/2003 | Wissenbach et al. |
| 2003/0139585 A1 | 7/2003 | Uhlmann et al. |
| 2003/0143732 A1* | 7/2003 | Fosnaugh et al. .......... 435/325 |
| 2003/0158403 A1 | 8/2003 | Manoharan et al. |
| 2003/0166282 A1 | 9/2003 | Brown et al. |
| 2003/0175906 A1 | 9/2003 | Manoharan et al. |
| 2003/0187240 A1 | 10/2003 | Cook et al. |
| 2003/0190635 A1 | 10/2003 | McSwiggen |
| 2003/0206887 A1 | 11/2003 | Morrissey et al. |
| 2003/0207804 A1 | 11/2003 | Manoharan et al. |
| 2003/0224377 A1 | 12/2003 | Wengel et al. |
| 2004/0001811 A1* | 1/2004 | Kreutzer et al. .......... 424/93.21 |
| 2004/0009938 A1 | 1/2004 | Manoharan et al. |
| 2004/0014957 A1 | 1/2004 | Eldrup et al. |
| 2004/0018999 A1 | 1/2004 | Beach et al. |
| 2004/0029275 A1 | 2/2004 | Brown et al. |
| 2004/0102618 A1 | 5/2004 | Crooke et al. |
| 2004/0146867 A1 | 7/2004 | Slattum et al. |
| 2004/0171033 A1 | 9/2004 | Baker et al. |
| 2004/0180351 A1 | 9/2004 | Giese et al. |
| 2004/0259247 A1* | 12/2004 | Tuschl et al. ............... 435/375 |
| 2005/0020525 A1 | 1/2005 | McSwiggen et al. |
| 2005/0080246 A1 | 4/2005 | Allerson et al. |
| 2005/0142535 A1 | 6/2005 | Damha et al. |
| 2005/0164209 A1 | 7/2005 | Bennett et al. |
| 2005/0181382 A1 | 8/2005 | Zamore et al. |
| 2005/0221275 A1 | 10/2005 | Bennett et al. |
| 2005/0245474 A1 | 11/2005 | Baker et al. |
| 2005/0260755 A1* | 11/2005 | Baker et al. ................ 435/455 |
| 2005/0273868 A1 | 12/2005 | Rana |
| 2006/0127891 A1 | 6/2006 | McSwiggen et al. |
| 2007/0032446 A1 | 2/2007 | Cook et al. |

FOREIGN PATENT DOCUMENTS

| | | |
|---|---|---|
| DE | 3915432 A1 | 11/1990 |
| DE | 4110085 A1 | 1/1992 |
| DE | 10100588 A1 | 7/2002 |
| EP | 0260032 A2 | 3/1988 |
| EP | 0266168 A2 | 5/1988 |
| EP | 0269574 A2 | 6/1988 |
| EP | 0287313 A2 | 10/1988 |
| EP | 0339330 A2 | 11/1989 |
| EP | 339842 A2 | 11/1989 |
| EP | 0417999 A1 | 3/1991 |
| EP | 1389637 A1 | 2/2004 |
| JP | 2-264792 A | 10/1990 |
| WO | WO 86/05518 A1 | 9/1986 |
| WO | WO 89/12060 A1 | 12/1989 |
| WO | WO 90/15814 A1 | 12/1990 |
| WO | WO 91/06556 A1 | 5/1991 |
| WO | WO 91/10671 A1 | 7/1991 |
| WO | WO 91/15499 A1 | 10/1991 |
| WO | WO 92/02258 A1 | 2/1992 |
| WO | WO 92/03452 A1 | 3/1992 |
| WO | WO 92/03568 A1 | 3/1992 |
| WO | WO 92/07065 A1 | 4/1992 |
| WO | WO 92/20822 A1 | 11/1992 |
| WO | WO 92/20823 A1 | 11/1992 |
| WO | WO 92/22651 A1 | 12/1992 |
| WO | WO 93/07883 A1 | 4/1993 |
| WO | WO 93/24510 A1 | 12/1993 |
| WO | WO 94/01550 A1 | 1/1994 |
| WO | WO 94/02498 A1 | 2/1994 |
| WO | WO 94/02499 A1 | 2/1994 |
| WO | WO 94/02501 A1 | 2/1994 |
| WO | WO 94/17093 A1 | 8/1994 |
| WO | WO 94/23026 A1 | 10/1994 |
| WO | WO 94/26764 A1 | 11/1994 |
| WO | WO 96/07392 A2 | 3/1996 |
| WO | WO 96/11205 A1 | 4/1996 |
| WO | WO 97/26270 A2 | 7/1997 |
| WO | WO 97/30064 A1 | 8/1997 |
| WO | WO 97/46570 A1 | 12/1997 |
| WO | WO 98/16550 A1 | 4/1998 |
| WO | WO 98/39352 A1 | 9/1998 |
| WO | WO 98/52614 A2 | 11/1998 |
| WO | WO 99/14226 A2 | 3/1999 |
| WO | WO 99/32619 A1 | 7/1999 |

| | | | |
|---|---|---|---|
| WO | WO 00/08044 A1 | 2/2000 |
| WO | WO 00/44895 A1 | 8/2000 |
| WO | WO 00/44914 A1 | 8/2000 |
| WO | WO 00/49035 A1 | 8/2000 |
| WO | WO 00/63364 A2 | 10/2000 |
| WO | WO 00/76554 A1 | 12/2000 |
| WO | WO 01/29058 A1 | 4/2001 |
| WO | WO 01/36641 A2 | 5/2001 |
| WO | WO 01/36646 A1 | 5/2001 |
| WO | WO 01/48183 A2 | 7/2001 |
| WO | WO 01/49687 A2 | 7/2001 |
| WO | WO 01/75164 A2 | 10/2001 |
| WO | WO 02/36743 A2 | 5/2002 |
| WO | WO 02/38578 A1 | 5/2002 |
| WO | WO 02/44321 A2 | 6/2002 |
| WO | WO 03/004602 A2 | 1/2003 |
| WO | WO 03/070918 A2 | 8/2003 |
| WO | WO 03/072705 A2 | 9/2003 |
| WO | WO 2004/015107 A2 | 2/2004 |
| WO | WO 2004/041889 A2 | 5/2004 |
| WO | WO 2004/043977 A2 | 5/2004 |
| WO | WO 2004/043978 A2 | 5/2004 |
| WO | WO 2004/043979 A2 | 5/2004 |
| WO | WO 2004/044133 A2 | 5/2004 |
| WO | WO 2004/044136 A2 | 5/2004 |
| WO | WO 2004/044138 A2 | 5/2004 |
| WO | WO 2004/044139 A2 | 5/2004 |
| WO | WO 2004/044140 A2 | 5/2004 |
| WO | WO 2004/083430 A2 | 9/2004 |
| WO | WO 2004/097049 A1 | 11/2004 |
| WO | WO 2004/113496 A2 | 12/2004 |
| WO | WO 2005/027962 A2 | 3/2005 |

OTHER PUBLICATIONS

McIntyre et al. (1993) Antisense Res. Dev. 3:309-322.*
Zhao et al. (1996) Biochemical Pharmacology 51:173-182.*
McCaffrey et al. (2002) Nature 418:38-39.*
Fire et al. (1998) Nature 391:806-811.*
Graham et al. (1998) "In Vivo Distribution and Metabolism of a Phosphorothioate Oligonucleotide within Rat Liver after Intravenous Administration" J. Pharmacol. Exp. Therapeutics 286:447-458.*
Nicolazzi et al. Current Medicinal Chemistry, 2003, 10, 1263-1277.*
Butler, M. et al., "Specific Inhibition of PTEN Expression Reverses Hyperglycemia in Diabetic Mice," *Diabetes* (2002) 51:1028-1034.
Caplen, N. J. et al., "Specific inhibition of gene expression by small double-stranded RNAs in invertebrate and vertebrate systems," *Proc. Natl. Acad. Sci. USA* (2001) 98(17):9742-9747.
Cossum, P. A. et al., "Disposition of the $^{14}$C-Labeled Phosphorothioate Oligonucleotide ISIS 2105 after Intravenous Administration to Rats," *J. Pharmacol. Exp. Ther.* (1993) 267(3):1181-1190.
Crawford, J. M., "Role of Vesicle-Mediated Transport Pathways in Hepatocellular Bile Secretion," *Semin. Liver Dis.* (1996) 16(2):169-189.
Elbashir, S. M. et al., "Duplexes of 21-nucleotide RNAs mediate RNA interference in cultured mammalian cells," *Nature* (2001) 411:494-498.
Fraser, A. G. et al., "Functional genomic analysis of *C. elegans* chromosome I by systematic RNA interference," *Nature* (2000) 408:325-330.
Geary, R. S. et al., "Pharmacokinetic Properties of 2'-O-(2-Methoxyethyl)-Modified Oligonucleotide Analogs in Rats," *J. Pharmacol. Exp. Therap.* (1998) 296(3):447-458.
Graham, M. J. et al., "In Vivo Distribution and Metabolism of a Phosphorothioate Oligonucleotide within Rat Liver after Intravenous Administration," *J. Pharmacol. Exp. Therap.* (1998) 286(1):447-458.
Grishok, A. et al., "Genetic Requirements for Inheritance of RNAi in *C. elegans*," *Science* (2000) 287:2494-2497.
Leeds, J. M. et al., "Pharmacokinetic Properties of Phosphorothioate Oligonucleotides," *Nucleosides Nucleotides* (1997)16(7-9):1689-1693.

Lewis, D. L. et al., "Efficient delivery of siRNA for inhibition of gene expression in postnatal mice," *Nature Genetics* (2002) 32:107-108.
Marwick, C., "First "Antisense" Drug Will Treat CMV Retinitis," *J. Am. Med. Assoc.* (1998) 280(10):871.
McCaffrey, A. P. et al., "RNA interference in adult mice," *Nature* (2002) 418:38-39.
McQueen, C. A. et al., "Effect of Nalidixic Acid on DNA Repair in Rat Hepatocytes," *Cell Biol. Toxicol.* (1989) 5(2):201-206.
Nestle, F. O. et al., "Cationic Lipid is not Required for Uptake and Selective Inhibitory Activity of ICAM-1 Phosphorothioate Antisense Oligonucleotides in Keratinocytes," *J. Invest. Dermatol.* (1994) 103:569-575.
Nykänen, A. et al., "ATP Requirements and Small Interfering RNA Structure in the RNA Interference Pathway," *Cell* (2001) 107:309-321.
Schwartz, D. S. et al., "Evidence that siRNAs Function as Guides, Not Primers, in the *Drosophila* and Human RNAi Pathways," *Mol. Cell.* (2002) 10:537-548.
Song, E. et al., "RNA interference targeting Fas protects mice from fulmiant hepatitis," *Nature Med.* (2003) 9(3):347-351.
Vickers, T. A. et al., "Efficient Reduction of Target RNAs by Small Interfering RNA and RNase H-dependent Antisense Agents," *J. Biol. Chem.* (2003) 278(9):7108-7118.
Zamecnik, P. C. et al., "Inhibition of Rous sarcoma virus replication and cell transformation by a specific oligodeoxynucleotide," *Proc. Natl. Acad. Sci. USA* (1978) 75(1):280-284.
Zamore, P. D. et al., "RNAi: Double-Stranded RNA Directs the ATP-Dependent Cleavage of mRNA at 21 to 23 Nucleotide Intervals," *Cell* (2000) 101:25-33.
Zamore, P. D., "Ancient Pathways Programmed by Small RNAs," *Science* (2002) 296:1265-1269.
Zhang, H. et al., "Reduction of liver Fas expression by an antisense oligonucleotide protects mice from fuminant hepatitis," *Nature Biotech.* (2000) 18:862-867.
Leydier, C. et al., "4'-Thio-RNA: Synthesis of Mixed Base 4'-Thio-Oligoribonucleotides, Nuclease Resistance, and Base Pairing Properties with Complementary Single and Double Strand," Antisense Research and Development, 1995, 5, 167-174.
Olie, R.A. et al., "Analysis of ribosyl-modified, mixed backbone analogs of a bcl-2/bcl-xL antisense oligonucleotide," Biochimica et Biophysica Acta, 1576 (2002), 101-109.
Braasch, D.A. et al., "RNA Interference in Mammalian Cells by Chemically-Modified RNA," Biochemistry, 2003, 42, 7967-7975.
Grünweller, A. et al., "Comparison of different antisense strategies in mammalian cells using locked nucleic acids, 2'-O-methyl RNA, phosphorothioates and small interfering RNA," Nucleic Acids Research, 2003, 31(12), 3185-3193.
Abe, A., et al., "Conformational energies and the random-coil dimensions and dipole moments of the polyoxides CH3O[CH2)yO]xCH3," J. Am. Chem. Soc., 1976, 98(21), 6468-6476.
Afonina, I. et al., "Sequence-specific arrest of primer extension on single-stranded DNA by an oligonucleotide-minor groove binder conjugate," Proc. Natl. Acad. Sci. USA (1996) 93:3199-3204.
Agarwal, et al., "Oligodeoxynucleoside Phosphoramidates and Phosphorothioates as Inhibitors of Human Immunodeficiency Virus" Proc. Natl. Acad. Sci. USA , 1988, 85, 7079-7083.
Agarwal, et al., "Synthesis and Enzymatic Properties of Deoxyribooligonucleotides Containing Methyl and Phenylphosphonate Linkages", Nucleic Acid Research 1979, 6, 3009-3024.
Agrawal, S. et al., "Synthesis and Anti-HIV Activity of Oligoribonucleotides and Their Phosphorothioate Analogs," Ann. N.Y. Acad. Sci., 1992, 2-10.
Agrawal, S. et al., "Antisense therapeutics: is it as simple as complementary base recognition?," Molecular Med. Today, vol. 6(2), pp. 72-81 (2000).
Agrawal, S., "Antisense Oligonucleotides: Towards Clinical Trials," TIBTECH, 1996, 14, 376-388.
Agris, et al., "Inhibition of Vesicular Stomatitis Virus Protein Synthesis and Infection by Sequence-Specific Oligodeoxyribonucleoside Methylphosphonates", Biochemistry 1986, 25, 6268-6275.

Akashi, et al., "Novel Stationary Phases for Affinity Chromatography. Nucleobase-Selective Recognition of Nucleosides and Nucleotides on Poly(9-vinyladenine)-Supported Silica Gel)", Chem. Letters, 1988, 1093-1096.

Alahari, "Novel chemically modified oligonucleotides provide potent inhibition of P-glycoprotein expression," J. Pharmacology and Experimental Therapeutics, 1998, 286(1), 419-428.

Alberts, et al., "DNA-Cellulose Chromatography", Meth. Enzymol., 1971, 21, 198-217.

Allerson, C.R. et al., Abstract of the 227th ACS National Meeting, Anaheim, CA, Mar. 28-Apr. 1, 2004.

Allerson, C.R. et al., "Fully 2'-Modified Oligonucleotide Duplexes with Improved in Vitro Potency and Stability Compared to Unmodified Small Interfering RNA," J. Med. Chem., 2005, 48, 901-904.

Altmann, K. -H. et al., "Second generation antisense oligonucleotides—inhibition of PKC-alpha and c-RAF kinase expression by chimeric oligonucleotides incorporating 6' -substituted carbocyclic nucleosides and 2' -O-ethylene glycol substituted ribonucleosides," Nucleosides & Nucleotides, 1997, 16(7-9), 917-926.

Altmann, K.-H., et al., "Second generation of antisense oligonucleotides: from nuclease resistance to biological efficacy in animals," Chimia, 1996, 50, 168-176.

Altmann, K.H., et al., "Second-generation antisense oligonucleotides: structure-activity relationships and the design of improved signal-transduction inhibitors," Biochem. Soc. Trans., 1996, 24, 630-637.

Altschul, S.F. et al., "Basic Local Alignment Search Tool," J. Mol. Biol., 1990, 215, 403-410.

Amarzguioui, M., et al., "Tolerance for mutations and chemical modifications in a siRNA," Nucleic Acids Res., 2003, 31(2), 589-595.

Ambros, V. et al., "A uniform system for MicroRNA annotation," RNA (2003) 9: 277-279.

Ambros, V. et al., "MicroRNAs and Other Tiny Endogenous RNAs in *C. elegans*," Curr Biol. (2003) 13: 807-818.

Ambros, V. et al., "MicroRNAs: Tiny Regulators with Great Potential," Cell (2001) 107: 823-826.

Antopolsky, M. et al., "Peptide-Oligonucleotide Phosphorothioate Conjugates with Membrane Translocation and Nuclear Localization Properties," Bioconjuxate Chem. (1999) 10(4):598-606.

Arar, K. et al., "Synthesis and Antiviral Activity of Peptide-Oligonucleotide Conjugates Prepared by Using Na-(Bromoaceytl)peptides," Bioconjugate Chem. (1995) 6(5):573-577.

Arndt-Jovin, et al., "Covalent Attachment of DNA to Agarose", Eur. J. Biochem., 1975, 54, 411-418.

Arnott, S., et al., "Optimised parameters for A-DNA and B-DNA," Biochem. & Biophys. Res. Comm., 1972, 47(6), 1504-1510.

Arya, S. K. et al., "AInhibition of RNA Directed DNA Polymerase of Murine Leukemia Virus by 2'-O-Alkylated Polyadenylic Acids," Biochemical and Biophysical Research Communications, 1974, 59(2), 608-615.

Arya, S. K. et al., "Inhibition of Synthesis of Murine Leukemia Virus in Cultured Cells by Polyribonucleotides and Their 2'-O-Alkyl Derivatives," Molecular Pharmacology, 1976, 12, 234-241.

Asseline, U. et al., "Nucleic acid-binding molecules with high affinity and base sequence specificity: Intercalating agents covalently linked to oligodeoxynucleotides," Proc. Natl. Acad. Sci USA (1984) 81: 3297-3301.

Astriab-Fisher et al., "Conjugates of antisense olgonucleotides with the TAT and antennapedia cell-penetrating peptides: effects on cellular update, binding to target sequences and biologic actions," Pharmaceutical Research (2002) 19(6): 744-754.

Astriab-Fisher, A. et al., "Antisense Inhibition of P-glycoprotein Expression Using Peptide-Oligonucleotide Conjugates," Biochem. Pharmacol. (2000) 60, 83-90.

Baker, B. F. et al., "Oligonucleotide-europium complex conjugate designed to cleave the 5' cap structure of the ICAM-I transcript potentiates antisense activity in cells," Nucleic Acids Res. (1999) 27(6):1547-1551.

Baker, B.F., et al., "2'-O-(2-methoxy)ethyl-modified anti-intercellular adhesion molecule 1 (ICAM-1) oligonucleotides selectively increase the ICAM-1 mRNA level and inhibit formation of the ICAM-1 translation initiation complex in human umbilical vein endothelial cells," J. Biol. Chem., 1997, 272(18), 11944-12000.

Bartel, B. et al., "MicroRNAs: At the Root of Plant Development," Plant Physiol. (2003) 132: 709-717.

Bass, B.L., "Double-stranded RNA as a template for gene silencing," Cell, 2000, 101, 235-238.

Bayer, E. et al., "A New Support for Polypeptide Synthesis in Columns," Tetrahedron Letters, 1970, 51, 4503-4505.

Beaucage et al. "The Functionalization of Oligonucleotides Via Phosphoramidite Derivatives", (1993) Tetrahedron 49(10):1925-1963.

Beaucage S. and Iyer, R., "Advances in the synthesis of oligonucleotides by the phosphoramidite approach", Tetrahedron Letters, 1992, 48, 2223-2311.

Beaucage S. And Iyer, R., "The synthesis of modified oligonucleotides by the phosphoramidite approach and their applications", Tetrahedron, 1993, 49, 6123-6194.

Beaucage, S.L. et al., "Deoxynucleoside Phosphoramidites—A New Class of Key Intermediates for Deoxypolynucleotide Synthesis,", Tetrahedron Letts., 1981, 22, 1859-1862.

Beigelman, L., et al., "Chemical modification of hammerhead ribozymes," J. of Biological Chem,. 1995, 270(43), 25702-25708.

Berger, "Crystal structures of B-DNA with incorporated 2'-deoxy-2'-fluoro-arabino-furanosyl thymines: implications of conformational preorganization for duplex stability," Nucleic Acids Research, 1998, 26, 2473-2480.

Bevilacqua et al., "Minor-Groove Recognition of Double-Stranded RNA by the Double-Stranded RNA-Binding Domain from the RNA-Activated Protein Kinase PKR," Biochemistry, 1996, 35, 9983-9994.

Bhat, et al., "A Simple and Convenient Method for the Selective N-Acylations of Cytosine Nucleosides", Nucleosides and Nucleotides, 1989, 8, 179-183.

Biggadike, et al., "Short convergent route to homochiral carbocylic 2'-deoxynucleosides and carbocyclic robonucleosides", J. Chem. Soc. Chem. Commun. 1987, 1083-1084.

Blanks, et al., "An oligodeoxynucleotide affinity column for the isolation of sequence specific DNA binding proteins", Nucleic Acids Res., 1988, 16, 10283-10299.

Blomberg, P., "Control of replication of plasmid R1: the duplex between the antisense RNA, CopA, and its target, CopT, is processed specifically in vivo and in vitro by Rnase III", EMBO J., 1990, 9, 2331-2340.

Bollig, F. et a]., "Affinity purification of ARE-binding proteins identifies poly(A)-binding protein 1 as a potential substrate in MK2-induced mRNA stabilization," Biochem. Bioophys. Res. Commun. (2003) 301: 665-670.

Bongartz, J.-P. et al., "Improved biological activity of antisense oligonucleotides conjugated to a fusogenic peptide," Nucleic Acids Res. (1994) 22(22):4681-4688.

Bonora, G. M. et al., "Antisense activity of an anti-HIV oligonucleotide conjugated to linear and branched high molecular weight polyethylene glycols," Farmaco (1998) 53:634-637.

Bonora, G. M. et al., "Biological Properties of Antisense Oligonucleotides Conjugated to—Different High-Molecular Mass Poly(Ethylen Glycols)," Nucleosides Nucleotides (1999) 18(6&7):1723-1725.

Bonora, G.M., et al., "A liquid-phase process suitable for large-scale synthesis of phosphorothioate oligonucleotides," Organic Process Res. & Develop., 2000, 225-231.

Borer, et al., "Stability of ribonucleic acid double-stranded helices," J. Mol. Biol., 1974, 86, 843-853.

Boutla, A. et al., "Short 5'-phosphorylated double-stranded RNAs induce RNA interference in *Drosophila*," Current Biology, 2001, 11(22), 1776-1780.

Braasch, D.A. et al., "Locked nucleic acid (LNA): fine-tuning the recognition of DNA and RNA," Chem Biol, 2001, 8, 1-7.

Braasch, D.A. et al., "RNA Interference in Mammalian Cells by Chemically-Modified RNA," Biochemistry, 2003, 42, 7967-7975.

Braasch, D.A., et al., "Novel antisense and peptide nucleic acid strategies for controlling gene expression," Biochemistry, Apr. 9, 2002, 41(14), 4503-4510.

Branch, A., "A Good Antisense is Hard to Find," TIBS, 1998, 23, 45-50.

Branden, L. J. et al., "A peptide nucleic acid-nuclear localization signal fusion that mediates nuclear transport of DNA," Nature Biotech (1999) 17:784-787.

Brantl, S., "Antisense-RNA regulation and RNA interference," Biochimica et Biophysica Acta, 2002, 1575, 15-25.

Brazma, A., et al., "Gene expression data analysis," FEBS Lett., 2000, 480, 17-24.

Brill, et al., "Synthesis of Oligodeoxynucleoside Phosphorodithioates Via Thioamidites", J. Am. Chem. Soc. 1989, 111, 2321-2322.

Brown-Driver et al., "Inhibition of Translation of Hepatitis C Virus RNA by 2'-Modified Antisense Oligonucleotides," Antisense Nucleic Acid Drug Dev. (1999) 9(2): 145-154.

Buhr, C.A. et al., "Oligodeoxynucleotides containing C-7 propyne analogs of 7-deaza-2'-deoxyguanosine and 7-deaza-2'-deoxyadenosine," Nucleic Acids Research, 1996, 24(15), 2974-2980.

Bunemann, et al., Immobilization of denatured DNA to macroporous supports: I. Efficiency of different coupling procedures, Nucleic Acids Res., 1982, 10, 7163-7180.

Bunemann, H., "Immobilization of denatured DNA to macroporous supports: II. Steric and kinetic parameters of heterogeneous hybridization reactions", Nucleic Acids Res., 1982, 10, 7181-7196.

Butke, et al., "Facile synthesis of 2'amino-2deoxynucleoside from the corresponding arabino derivative," Nucleic Acid Chemistry, 1986, Part Three, 149-152.

Caplen et al., "dsRNA-mediated gene silencing in cultured *Drosophila* cells: a tissue culture model for the analysis of RNA interference," Gene (2000) 252: 95-105.

Carmell, M.A. et al., "The argonaute family: tentacles that reach into RNAi, developmental control, stem cell maintenance, and tumorigenesis," Genes and Development, 2002, 16, 2733-2742.

Carulli, J.P., et al., "High throughput analysis of differential gene expression," J. Cellular Biochem. Suppl., 1998, 30(31), 286-296.

Caruthers, M., "Synthesis of Oligonucleotides and Oligonucleotide Analogues", in "Oligonucleotides. Antisense Inhibitors of Gene Expression.", J.S. Cohen, Ed., CRC Press, Inc., 7-24, (1989).

Castle, et al., "Imidazo[4, 5-D]pyridazines. I. Synthesis of 4,7-disubstituted derivatives", Journal of Organic Chemistry, 1958, 23, 1534-1538.

Cazalla, D. et al., "Nuclear Export and Retention Signals in the RS Domain of SR Proteins," Mol. Cell. Biol. (2002) 22(19):6871-6882.

Cazenave, C. et al., "Enzymatic amplification of translation inhibition of rabbit β-globin mRNA mediated by anti-messenger oligodeoxynucleotides covalently linked to intercalating agents", Nucl. Acids Res., 1987, 15, 4717-4736.

Celis, J.E., et al., "Gene expression profiling: monitoring transcription and translation production using DNA microarrays and proteomics," FEBS Lett., 2000, 480, 2-16.

Cerutti, H., "RNA interference: traveling in the cell and gaining functions?" Trends in Genetics (2003) 19(1): 39-46.

Chaloin, L. et al., "Design of Carrier Peptide-Oligonucleotide Conjugates with Rapid Membrane Translocation and Nuclear Localization Properties," Biochem. Biophys. Res. Commun. (1998) 243:601-608.

Chaput, J.C., et al., "DNA polymerase-mediated DNA synthesis on a TNA template," J. Am. Chem. Soc., 2003, 125, 856-857.

Chen and Wu, "Studies on Fluoroalkylation and Fluroalkoxylation. Part 33. Direct Trifluoromethylation of Aryl Halides with Fluorosulphonyldifluoromethyl Iodide in the Presence of Copper: an Electron Transfer Induced Process," J. Chem. Soc., Perkin Transactions, 1989, 1, 2385-2387.

Chiang et al., "Antisense Oligonucleotides Inhibit Intercellular Adhesion Molecule 1 Expression by Two Distinct Mechanisms," J. Biol. Chem., 1991, 266, 18162-18171.

Chirila, T.V. et al., "The use of synthetic polymers for delivery of therapeutic antisense oligodeoxynucleotides," Biomaterials, vol. 23(2), pp. 321-342 (2002).

Chiu et al., "siRNA function in RNAi: a chemical modification analysis," RNA, 2003, 9, 1034-1048.

Chiu, Y.-L. et al., "RNAi in human cells: basic structural and functional features of small interfering RNA," Molecular Cell, Sep. 2002, 10, 549-561.

Chladek, et al., "Facile Synthesis of 2'Amino-2'Deoxyadenosine," J. Carbohydtrates, Necleosides & Nucleotides, 1980, 7, 63-75.

Chodosh, et al., "A Single Polypeptide Possesses the Binding and Transcription Activities of the Adenovirus Major Late Transcription Factor", Mol. Cell. Biol., 1986, 6, 4723-4733.

Choung, S. et al., "Chemical modification of siRNAs to improve serum stability without loss of efficacy," Biochemical and Biophysical Research Communications, 2006, 342, 919-927.

Christofferson et al., "Ribozymes as human therapeutic agents", J. Med. Chem., 1995, 38(12), 2023-2037.

Chun-Nam Lok et al., "Potent gene-specific inhibitory properties of mixed backbone antisense oligonucleotides comprised of 2'-deoxy-2'-fluoro-D-arabinose and 2'-deoxyribose nucleotides," Biochemistry, 2002, 41, 3457-3467.

Cogoni, C. et al., "Post-transcriptional gene silencing across kingdoms," Curr. Opin. Genet Dev., 2000, 10(6), 638-643.

Cohen, G. L. et al., "Sequence Dependent Binding of cis-Dichlorodiamrnineplatinum(II) to DNA," J. Am. Chem. Soc. (1980) 102(7), 2487-2488.

Concise Encyclopedia of Polymer Science and Engineering, pp. 858-859, Kroschwitz, J.I., Ed., John Wiley & Sons, 1990.

Constant et al., "Heterodimeric Molecules Including Nucleic Acid Bases and 9-Aminoacridine Spectroscopic Studies, Conformations, and Interactions with DNA", Biochemistry, 1988, 27, 3997-4003.

Conte, M.R., et al., "Conformational properties and thermodynamics of the RNA duplex r(CGCAAAUUUGCG)2: comparison with the DNA analogue d(CGCAAATTTGCG)2," Nucleic Acids Res., 1997, 25(13), 2627-2634.

Cook, "Medicinal chemistry of antisense oligonucleotides—future opportunities," Anti-Cancer Drug Design, 1991, 6, 585-607.

PCT International Search Report dated Jan. 24, 2005 (PCTUS03/35087).

The PCT International Search Report dated Aug. 13, 2004 (PCT/US03/35072).

The PCT International Search Report dated Aug. 2, 2004 (PCT/US03/35068).

The PCT International Search Report dated Aug. 23, 2004 (PCT/US03/35063).

The PCT International Search Report dated Dec. 1, 2003 (PCT/US03/19043).

Corey, D. R. et al., "Generation of a Hybrid Sequence-Specific Single-Stranded Deoxyribonuclease," Science (1987) 238:1401-1403.

Corey, D. R. et al., "Sequence-Selective Hydrolysis of Duplex DNA by an Oligonucleotide-Directed Nuclease," J. Am. Chem. Soc. (1989) 111(22):8523-8525.

Corey, D. R., "48000-fold Acceleration of Hybridization by Chemically Modified Oligonucleotides," J. Am. Chem. Soc. (1995) 117(36):9373-9374.

Cornell, W. D. et al., "A Second Generation Force Field for the Simulation of Proteins, Nucleic Acids, and Organic Molecules," J. Am. Chem. Soc., 1995, 117, 5179-5197.

Couzin, J., "Small TNAs Make Big Splash," Science (2002) 298: 2296-2297.

Crooke, et al., "Kinetic characteristics of *Escherichia coli* Rnase H1: cleavage of various antisense oligonucleotide-RNA duplexes", Biochem. J., 1995, 312, 599-608.

Crooke, et al., "Pharmacokinetic Properties of Several Novel Oligonucleotide Analogs in mice", J. Pharmacol. Exp. Therm., 1996, 277, 923-937.

Crooke, S.T. And Bennett, C.F., "Progress in Antisense Oligonucleotide Therapeutics", Annu. Rev. Pharmacol. Toxicol., 1996, 36, 107-129.

Crooke, S.T., Antisense Research & Application, Chapter 1, pp. 1-50, Publ. Springer-Verlag, Ed. S.T. Crooke (1998).

Cummins, L.L. et al., "Characterization of fully 2'modified oligoribonucleotide hetero- and homoduplex hybridization and nuclease sensitivity," Nucleic Acids Research, 1995, 23(11), 2019-2024.

Czauderna, F., et al., "Structural variations and stabilizing modifications of synthetic siRNAs in mammalian cells," Nucleic Acids Res., 2003, 31(11), 2705-2716.

Dagle, et al., "Pathways of Degradation and Mechanism of Action of Antisense Oligonucleotides in *Xenopus laevis* Embryos", Antisense Res. And Dev., 1991, 1, 11-20.

Dagle, et al., "Physical properties of oligonucleotides containing phosphoramidate-modified internucleoside linkages", Nucleic Acids Research, 1991, 19, 1805-1810.

Dagle, et al., "Targeted degradation of mRNA in *Xenopus oocytes* and embryos directed by modified oligonucleotides: studies of An2 and cyclin in embryogenesis", Nucleic Acids Research, 1990, 18, 4751-4757.

Dahl, B.H. et al., "A Highly Reactive, Odourless Substitute for Thiphenol/Triethylmaine as a Deprotection Reagent in the Synthesis of Oligonucleotides and their Analogues," Acta Chem. Scand., 1990, 44, 639-641.

Dake, et al., "Purification and Properties of the Major Nuclease from Mitochondria of *Saccharomyces cerevisiae*", J. Biol. Chem., 1988, 263, 7691-7702.

Damha, et al., "Solution and solid phase chemical synthesis of arabinonucleotides", Can J. Chem., 1989, 831-839.

Damha, M.J., et al., "Hybrids of RNA and arabinonucleic acids (ANA and 2'F-ANA) are substrates of ribonuclease H," J. Am. Chem. Soc., 1998, 120, 12976-12977.

Dande, P. et al., Abstract from The 227th ACS National Meeting, Anaheim, CA, Mar. 28-Apr. 1, 2004.

Day, et al., "Immobilization of polynucleotides on magnetic particles", Biochem. J., 1991, 278, 735-740.

De las Heras, et al., "3'-C-Cyano-3'-Deoxythymidine," Tetrahedron Letters, 1988, 29, 941-944.

De Mesmeker, et al., "Antisense Oligonucleotides", Acc. Chem. Res., 1995, 28, 366-374.

DeClercq, E. et al., "Influence of various 2- and 2'-substituted polyadenyl acids on murine leukemia virus reverse transcriptase," Cancer Letters, 1979, 7, 27-37.

Dellinger, D.J. et al., "Solid-Phase Chemical Synthesis of Phosphonoacetate and Thiophosphonoacetate Oligodexynucleotides," J. Am. Chem. Soc., 2003, 125(4), 940-950.

Denny, W.A., "DNA-intercalating ligands as anti-cancer drugs: prospects for future design," Anti-Cancer Drug Design, 1989, 4, 241-263.

Dignam, et al., "Accurate transcription initiation by RNA polymerase II in a soluble extract from isolated mammalian nuclei," Nucleic Acids Res., 1983, 11, 1475-1489.

Divakar, et al., "Approaches to the Synthesis of 2'-Thio Analogues of Pyrimidine Ribosides", J. Chem. Soc., Perkins Trans., I, 1990, 969-974.

Divakar, et al., "Reaction Between 2,2'-Anhydro-1-β-D-arrabinofuranosyluracil and Thiolate Ions", J. Chem. Soc., Perkins Trans. I, 1982, 1625-1628.

Dreyer, et al., "Sequence-specific cleavage of single-stranded DNA: Oligodeoxynucleotide-EDTA-Fe(II)", Proc. Natl. Acad. Sci. USA, 1985, 82, 968-972.

Drmanac, et al., "DNA Sequence Determination by Hybridization: A Strategy for Efficient Large-Scale Sequencing", Science, 1993, 260, 1649-1652.

Duff, R. J. et al., "[17] Intrabody Tissue-Specific Delivery of Antisense Conjugates in Animals: Ligand-Linker-Antisense Oligomer Conjugates," Methods Enzymol. (2000) 313:297-321.

Duncan, et al., "Affinity Chromatography of a Sequence-Specific DNA Binding Protein Using Teflon-Linked Oligonucleotides", Anal. Biochem., 1988, 169, 104-108.

Dunn, J.J. and Studier, F.W., "Effect of RNAase III Cleavage on Translation of Bacteriophage T7 Messenger RNAs", J. Mol. Biol., 1975, 99, 487-499.

Eckstein, et al., "Polynucleotides Containing 2'Chloro-2'Deoxyribose", Biochemistry, 1972, 11, 4336-4344.

Eddy, S.R., "Non-Coding RNA Genes and the Modern RNA World," Nature Rev. Genetics (2001) 2: 919-929.

Eder, P.S. and Walder, J.A., "Ribonuclease H from K562 Human Erythroleukemia Cells", J. Biol. Chem., 1991, 266, 6472-6479.

Efimov, V. A. et al., "Synthesis of Polyethylene Glycol—Oligonucleotide Conjugates," Bioorg. Khim. (1993) 19(8):800-804.

Egli, M. et al., "RNA Hydration: A Detailed Look," Biochemistry, 1996, 35, 8489-8494.

Elayadi, A.N. et al., "Application of PNA and LNA oligomers to chemotherapy," Curr. Opin. Investig. Drugs, 2001, 2(4), 558-561.

Elbashir, S.M., "RNA interference is mediated by 21- and 22-nucleotide RNAs," Genes & Devel., 2001, 15, 188-200.

Elbashir, S.M., et al., "Functional anatomy of siRNAs for mediating efficient RNAi in *Drosophila* melanogaster embryo lysate," EMBO J., 2001, 20(23), 6877-6888.

Elela, et al., "RNase III Cleaves Eukaryotic Preribosomal RNA at a U3 snoRNP-Dependent Site", Cell, 1996, 85, 115-124.

Elmén, J. et al., "Locked nucleic acid (LNA) mediated improvements in siRNA stability and functionality," Nucleic Acids Res. 2005, 33(1), 439-447.

Englisch, U. And Gauss, D.H., "Chemically Modified Oligonucleotides as Probes and Inhibitors", Angewandt Chemie, International Edition Engl., 1991, 30, 613-629.

EP Supplementary Search Report for EP 03716922 dated May 12, 2006.

Fahy, et al., "Design and synthesis of polyacrylamide-based oligonucleotide supports for use in nucleic acid diagnostics", Nucl. Acids Res., 1993, 21, 1819-1826.

Faria, M. et al., "Phosphoramidate oligonucleotides as potent antisense molecules in cells and in vivo," Nature Biotech., 2001, 19, 40-44.

Fazakerley, G.V., et al., "A→Z transition in the synthetic hexanucleotide (dCdGfl)3," FEBS, 1985, 182(2), 365-369.

Fedoroff, O.Y. et al., "Structure of a DNA:RNA Hybrid Duplex," J. Mol. Biol., 1993, 233, 509-523.

Fire et al., "RNA-triggered gene silencing," TIG (1999) 15(9): 358-363.

Firestone, R. A., "Low-Density Lipoprotein as a Vehicle for Targeting Antitumor Compounds to Cancer Cells," Bioconjugate Chem. (1994) 105-113.

Fishel, et al., "Z-DNA Affinity Chromatography", Methods Enzymol., 1990, 184, 328-342.

Flanagan, W. M. et al., "A cytosine analog that confers enhanced potency to antisense oligonucleotides," Proc. Natl. Acad. Sci. USA, Mar. 1999, 96, 3513-3518.

Flanagan, W.M. et al., "Cellular penetration and antisense activity by a phenoxazine-substituted heptanucleotide," Nature Biotechnol. (1999) 17(1): 48-52.

Fluiter, K. et al., "In vivo tumor growth inhibition and biodistribution studies of locked nucleic acids (LNA) antisense oligonucleotides," Nucleic Acids Res., 2003, 31(3), 953-962.

Fodor, et al., "Light-Directed, Spatially Addressable Parallel Chemical Synthesis", Science, 1991, 251, 767-773.

Fox, et al., "Nucleosides. XVIII. Synthesis of 2'-Fluorothymidine, 2'-Flurodeoxyuridine, and Other 2'-Halogeno-2'-Deoxy Nucleosides 12", J Org. Chem., 1964, 29, 558-564.

Francis, A.W. et al., "Probing the Requirements for Recognition and Catalysis in Fpg and MutY with Nonpolar Adenine Isosteres," J. Am. Chem. Soc. (2003) 125(52): 16235-16242.

Fraser, A., et al., "Synthesis and conformational properties of 2'-deoxy-2'-methylthiopyrimidine and -purine nucleosides:potential antisense applications," J. Heterocycl. Chem., 1993, 30, 1277-1287.

Freier, S. M. et al., "The ups and downs of nucleic acid duplex stability: structure-stability studies on chemically-modified DNA:RNA duplexes," Nucleic Acids Research, 1997, 25(22), 4429-4443.

Freskos, "Synthesis of 2'Deoxypyrimidine Nucleosides Via Copper (I) Iodine Catalysis," Nucleosides & Nucleotides, 1989, 8, 1075, 1076.

Frieden, M. et al., Expanding the design horizon of antisense oligonucleotides with alpha-L-LNA, Nucleic Acids Res., 2003, 31(21), 6365-6372.

Fromageot, H.P.M. et al., "The Synthesis of Oligonucleotides," Tetrahedron, 1967, 23, 2315-2331.

Fuchs, B. et al., "Identification of Differentially Expressed Genes by Mutually Subtracted RNA Fingerprinting," Anal. Biochem., 2000, 286, 91-98.

Fusi, et al., "Ribonucleases from the extreme thermophilic archaebacterium *S. Solfataricus*", Eur. J. Biochem., 1993, 16, 305-310.

Gabrielsen, et al., AMagnetic DNA affinity purification of yeast transcription factor T-a new purification principle for the ultrarapid isolation of near homogeneous factor, Nucleic Acids Research, 1989, 17, 6253-6267.

Gaffney, et al., "A New Strategy for the Protection of eoxyguanosine During Oligonucleotide Synthesis," Tetrahedron Letters, 1982, 23, 2257-2260.

Gait, M.J. et al., "Application of chemically synthesized RNA," RNA: Protein Interactions (1998) Smith (ed.), pp. 1-36.

Gait, M.J., Oligoribonucleotides, Antisense Research and Applications, 1993, Crooke, S.T. and Lebleu, B. (eds.), CRC Press, Boca Raton, pp. 289-301.

Gallo, M. et al., "2'-C-Methyluridine phosphoramidite: a new building block for the preparation of RNA analogues carrying the 2'-hydroxyl group," Tetrahedron, 2001, 57(27), 5707-5713.

Gao, J. et al., "Expanded-Size Bases in Naturally Sized DNA: Evaluation of Steric Effects in Watson-Crick Pairing," J. Am. Chem. Soc. (2004) 126(38): 11826-11831.

Gbenle, "Simultaneous Isolation of Cytoplasmic Endoribonuclease and Exoribonucease of *Trypanosoma Brucei*", Mol. Biochem. Parasitol., 1985, 15, 37-47.

Gbenle, "*Trypanosoma brucei*: Calcium-Dependent Endoribonuclease is Associated with Inhibitor Protein", Exp. Parasitol., 1990, 71, 432-438.

Gerdes, K., et al., "Mechanism of Killer Gene Activation. Antisense RNA-dependent Rnase III Cleavage Ensures Rapid Turn-over of the Stable-Hok, SrnB and PndA Effector Messenger RNAs", J. Mol. Biol., 1992, 226, 637-649.

Gingeras, et al., "Hybridization properties of immobilized nucleic acids", Nucl. Acids Res., 1987, 15, 5373-5391.

Going, J.J., et al., "Molecular pathology and future developments," Eur. J. Cancer, 1999, 35(14), 1895-1904.

Goldkorn, T. And Prockop, D.J., "A simple and efficient enzymatic method for covalent attachment of DNA to cellulose. Application for hybridization-restriction analysis and for in vitro synthesis of DNA probes", Nucleic Acids Res., 1986, 14, 9171-9191.

Gonzalez, C. et al., "Structure and Dynamics of a DNA-RNA Hybrid Duplex with a Chral Phosphorothioate Moiety: NMR and Molecular Dynamics with Conventional and Time-Averaged Restraints," Biochemistry, 1995, 34, 4969-4982.

Goodchild, et al., "Conjugates of Oligonucleotides and Modified Oligonucleotides: A Review of their Synthesis and Properties", Bioconjugate Chem., 1990, 1(3), 165-187.

Gorlach, M. et al., "The rnRNA Poly(A)-Binding Protein: Localization, Abundance, and RNABinding Specificity," Exp. Cells Res. (1994) 211:400-407.

Goss, T.A. and Bard, M., "High-performance affinity chromatography of DNA", J. Chromatogr., 1990, 508, 279-287.

Graham, et al., "Tritium Labeling of Antisense Oligonucleotides by Exchange with Tritiated Water," Nucleic Acids. Res., 1993, 16, 3737-3743.

Gravert, D.J., et al., "Organic synthesis on soluble polymer supports," Chem. Rev., 1997, 97, 489-509.

Griffey, R.H. et al., "2'-O-Aminopropyl Ribonucleotides: A Zwitterionic Modification that Enhances the Exonuclease Resistance and Biological Activity of Antisense Oligonucleotides," J. Med. Chem., 1996, 39(26), 5100-5109.

Griffin, B.E. et al., "The Synthesis of Oligoribonucleotides," Tetrahedron, 1967, 23, 2301-2313.

Gryaznov, S. et al., "Oligodeoxynucleotide N3'P5' Phosphoramidates: Synthesis and Hybridization Properties," J. Am. Chem. Soc., 1994, 116(7), 3143-3144.

Guckian, K.M. et al., "Structure and Base Pairing Properties of a Replicable Nonpolar Isostere for Deoxyadenosine," J Org Chem (1998) 63(26);9652-9656.

Guillerm, D. et al., "Synthesis of 4'-fluoroadenosine as an inhibitor of S-adenosyl-L-homocysteine hydrolase," Bioorganic & Medicinal Chemistry Letters, 1995, 5(14), 1455-1460.

Guo, et al., "Direct fluorescence analysis of genetic polymorphisms by hybridization with oligonucleotide arrays on glass supports", Nucl. Acids Res., 1994, 22, 5456-5465.

Guo, S. et al., "par-1, a Gene Required for Establishing Polarity in *C. elegans* Embryos, Encodes a Putative Ser/Thr Kinase That is Asymmetrically Distributed," Cell, 1995, 81(4), 611-620.

Gura, T., "A silence that speaks volumes," Nature, 2000, 404, 804-808.

Guschlbauer, et al., "Nucleoside conformation is Determined by the Electronegativity of the Sugar Substituent," Nucleic Acids Res., 1980, 8, 1421-1433.

Guschlbauer, W. et al., "Poly-2'-deoxy-2'-fluoro-cytidylic acid: enzymatic synthesis, spectroscopic characterization and interaction with poly-inosinic acid," Nucleic Acid Research, 1977, 4(6),1933-1943.

Guschlbauer, W., et al., "Use of 2'-deoxy-2'-fluoro-neclleosides in the study of polynucleotide conformation: a progress report," Nucleic Acid Research Symposium Series, 1982, 11,113-116.

Gutierrez, A.J. et al., "Antisense Gene Inhibition by C-5 Substituted Deoxyuridine-Containing Oligodeoxynucleotides," Biochemistry, 1997, 36(4), 743-748.

Guzaev, A. et al., "Conjugation of Oligonucleotides Via an Electrophilic Tether: N-Chloroacetarnidohexyl Phosphoramidite Reagent," Bioorg. Med. Chem. lett . (1998) 8:3671-3676.

Haeuptle and Dobberstein, "Translation arrest by oligonucleotides complementary to mRNA coding sequences yields polypeptides of predetermined length", Nucleic Acids Res., 1986, 14, 1427-1448.

Hakimelahi, G.H. et al., "High Yield Selective 3'-Silylation of Ribonucleosides," Tetrahedron Lett., 1981, 22(52), 5243-5246.

Hall, J. et al., "Efficient sequence-specific cleavage of RNA using novel europium complexes conjugated to oligonucleotides," Chem. Biol. (1994) 1(3):185-190.

Hamada et al., "Effects on RNA Interference in Gene Expression (RNAi) in Cultured Mammalian Cells of Mismatches and the Introduction of Chemical Modifications at the 3'Ends of siRNAs," Antisense and Nucleic Acid Drug Development (2002) 12:301-309.

Hamilton et al., "A species of small antisense RNA in post-transcriptional gene silencing in plants," Science (1999) 286 (5441): 950-952.

Hammond et al., "Post-Transcriptional Gene Silencing byDouble-Stranded RNA," Nature, 2001, 2, 110-119.

Hansske, et al., "2'and 3'-ketonucleosides and their arabino and XYLO reduction products," Tetrahedron, 1984, 40, 125-135.

Hariton-Gazal, E. et al., "Targeting of Nonkaryophilic Cell-Permeable Peptides into the Nuclei of Intact Cells by Covalently Attached Nuclear Localization Signals," Biochemistry (2002) 41(29):9208-9214.

Harry O'Kuru, R.E. et al., "A Short, Flexible Route toward 2'-C-Branched Ribonucleosides," J. Org. Chem., 1997, 62(6), 1754-1759.

Heasman, J., "Morpholino Oligos: Making Sense of Antisense?" Dev. Biol., 2002, 243, 209-214.

Henderson, B. R. et al., "A Comparison of the Activity, Sequence Specificity, and CRM1- Dependence of Different Nuclear Export Signals," Exp. Cell Res. (2000) 256:213-224.

Hertel, et al., "Synthesis of 2-deoxy-2,2-difluoro-D-ribose and 2-deoxy-2,2-difluoro-D-ribofuranosyl nucleosides," J. Org. Chem., 1988, 53, 2406-2409.

Hill, F. et al., "Polymerase recognition of synthetic oligodeoxyribonucleotides incorporating degenerate pyrimidine and purine bases," Proc. Natl. Acad. Sci. USA, 1998, 95, 4258-4263.

Hobbs, J. et al., "Poly 2'-Deoxy-2'-Aminouridylic Acid," Biochem. Biophys. Res. Commun., 1972, 46(4), 1509-1515.

Hobbs, J. et al., "Polynucleotides Containing 2'-Amino 2'-deoxyribose and 2'-Azido-2'-deoxyribose," Biochem., 1973, 12, 5138-5145.

Hobbs, J. et al., "Polynucleotides Containing 2'-Chloro-2'-deoxyribose," Biochem., Eckstein et al., Ed., 1972, 11, 4336-4344.

Hoffman, K., "Imidazole and its Derivatives" in The Chemistry of Heterocyclic Compounds, Weissberger, A., Ed.,Interscience Publishers, Inc., New York, 1953, 447.

Holen, T., et al., "Similar behaviour of single-strand and double-strand siRNAs suggests they act through a common RNAi pathway," Nucleic Acids Res., 2003, 31(9), 2401-2407.

Hornbeck, P. et al., Enzyme-Linked Immunosorbet Assays (ELIASE), Curr. Protocols Mol. Biol., 1991, John Wiley & Sons, pp. 11.2.1-11.2.22.

Hornung, V. et al., "Sequence-specific potent induction of IFN-a by short ineterfering RNA in plasmacytoid dendritic cells through TLR7," Nature Med., 2005, 11(3), 263-270.

Horton, N. C. et al., "The Structure of an RNA/DNA Hybrid: A Substrate of the Ribonuclease Activity of HIV-1 Reverse Transcriptase," J. Mol. Biol., 1996, 264, 521-533.

Huang, L. et al., "Oligonucleotide conjugates of Eu(III) tetraazamacrocycles with pendent alcohol and amide groups promote sequence-specific RNA cleavage," J Biol Inorg. Chem (2000) 5:85-92.

Huh, N. et al., "Design, Synthesis, and Evaluation of Mitomycin-Tethered Phosphorothioate Oligodeoxynucleotides," Bioconiugate Chem. (1996) 7:659-669.

Hunter, "Genetics: a touch of elegance with RNAi," Current Biology, Current Science (1999) 9(12): R440-R442.

Hunziker, J. et al., "Nucleic acid analogues: synthesis and properties," Modern Synthetic Methods, 1995, 331, 334-417.

Hyrup, B. And Nielsen, P., "Peptide Nucleic Acids (PNA): Synthesis, Properties and Potential Applications", Bioorganic & Med. Chem., 1996, 4, 5-23.

Ikehara, et al, "Studies of Nucleosides and Nucleotides-LXV' Purine Cyclonucleosides-26 A Versatile Method for the Synthesis of Purine O-Cyclo-Bucleosides. The First Synthesis of 8,2'Anhydro-8-Oxy 9-B-D-Arabinofuranosylguanine," Tetrahedron, 1975, 31, 1369-1372.

Ikehara, et al, "Studies of Nucleosides and Nucleotides-LXXXVII. 1, Purine Cyclonucleosides. XLII. Synthesis of 2'deoxy-2'fluorofunaosine," Chem. And Pharm. Bull., 1981, 29, 1034-1038.

Ikehara, et al. "Purine cyclonucleosides. (43). Synthesis and properties of 2'halogen-2'deoxyguanosines 1," Chem and Pharm Bull., 1981, 29, 3281-3285.

Ikehara, et al., "A Linear Relationship Between Electronegativity of 2'-Substituents and Conformation of Adenine Nucleosides," Tetrahedron Letters, 1979, 42, 4073-4076.

Ikehara, et al., "Improved Synthesis of 2'-fluoro-2'deoxyadenosine and Synthesis and Carbon-13 NMR Spectrum of its 3',5'-cyclic Phosphate Derivative," Nucleosides & Nucleotides, 1983, 2, 373-385.

Ikehara, et al., "Polynucleotides. L. synthesis and properties of poly (2'chloro-2'-deoxyadenylic acid) and poly (2'-bromo-2'-deoxyadenylic acid)", Nucleic Acids Res., 1978, 4, 4249-4260.

Ikehara, et al., "Polynucleotides. LII. Synthesis and properties of poly (2'-deox-2'-fluoroadenylic acid)," Nucleic Acids Research, 1978, 5, 1877-1887.

Ikehara, et al., "Polynucleotides. LVI. Synthesis and Properties of Poly(2'-deoxy-2'-fluoroinosinic Acid)", Nucleic Acids Res., 1978, 5, 3315-3324.

Ikehara, et al., "Purine 8-Cyclonucleosides," Accts. Chem Res., 1969, 2, 47-53.

Ikehara, et al., "Studies of Nucleosides and Nucleotides-LXXIV1 Purine Cyclonucleosides-34 A New Method for the Synthesis of 2'-substituted 2'-deoxyadenosines," Tetrahedron, 1978, 34, 1133-1138.

Ikehara, et al., "Studies of Nucleosides and Nucleotides-LXXXII. 1 Cyclonucleosides. (39). 2 Synthesis and properties of 2'halogen-2'-deoxyadenosines," Chem. Pharm. Bull., 1978, 26, 2449-2453.

Ikehara, M., "2'-substituted 2'-deoxypurineucleotides their conformation and properties," Heterocycles, 1984, 21(1), 75-90.

Imazawa, et al., "Nucleosides and nucleotides. Xll.1) Synthesis and properties of 2'-deoxy-2'-mercaptouridine and its derivates", Chem. Pharm. Bull., 1975, 23, 604-610.

Inoue et al., "Sequence dependent hydrolysis of RNA using modified oligonucleotide splints and Rnase H", FEBS Lett., 1987, 215(2), 327-330.

Inoue, et al., "Synthesis and hybridization studies on two complementary nona(2'-O-methyl) ribonucleotides", Nucleic Acid Res., 1987, 15, 6131-6148.

International Search Report Dated Aug. 23, 2004 for International Application No. PCT/US03/09808.

International Search Report dated Mar. 24, 2005 for International Application No. PCT/US03/35088.

International Search Report dated Nov. 18, 2004 for International Application No. PCT/US03/29294.

Jacobson, K.A. et al., "Methanocarba Analogues of Purine Nucleosides as Potent and Selective Adenosine Receptor Agonists," J. Med. Chem., 2000, 43(11), 2196-2203.

Jäger, A. et al., "Oligonucleotide N-alkylphosphoramidates: Synthesis and binding to polynucleotides", Biochemistry 1988, 27, 7237-7246.

Janik, B., et al., "Synthesis and Properties of Poly 2'-Fluoro-2'-Deoxyuridylic Acid," Biochem. Biophys. Res. Comm., 1972, 46(3), 1153-1160.

Jarvi, et al., "Synthesis and biological evaluation of dideoxunucleosides containing a difluoromethylene unit", Nucleosides & Nucleotides, 1989, 8, 1111-1114.

Jaschke, A. et al., "Synthesis and properties of oligodeoxyribonucleotide-polyethyleneg lycol conjugates," Nucleic Acids Res. (1994) 22(22):4810-4817.

Jayaraman, et al., "Selective Inhibition of *Escherichia Coli* Protein Synthesis and Growth by Nonionic Oligonucleotides Complementary to the 3' end of 16S rRNA", Proc. Natl. Acad. Sci. USA 1981, 78(3), 1537-1541.

Jen et al., "Suppression of Gene Expression by Targeted Disruption of Messenger RNA: Available Options and Current Strategies," Stem Cells, 2000, 18, 307-319.

Jones, et al., "4'-substituted nucleosides. 5. hydroxymethylation of nucleoside 5'-aldehydes", J. Org. Chem., 1979, 44, 1309-1317.

Jones, et al., "Transient protection: Efficient one-flask synthesis of protected deoxynucleosides", J. Am. Chem. Soc., 1982, 104, 1316-1319.

Jones, L.J. et al., "RNA Quantitation by Fluorescence-Based Solution Assay: RiboGreen Reagent Characterization," Anal. Biochem., 1998, 265, 368-374.

Jones, S.S. et al., "Migration of t-Butyldimethylsilyl Protecting Groups," J.C.S. Perkin 1, 1979, 2762-2764.

Jorgensen. R. A. et al., "Chalcone synthase cosuppression phenotypes in petunia flowers: comparison of sense vs. antisense constructs and single-copy vs. complex T-DNA sequences," Plant Mol. Biol., 1996, 31(5), 957-973.

Juby, C. D. et al., "Facile Preparation of 3'0ligonucleotide-Peptide Conjugates," Tetrahedron Letters (1991) 32(7):879-882.

Jungblut, P.R., et al., "Proteomics in human disease: cancer, heart and infectious diseases," Electrophoresis, 1999, 20, 2100-2110.

Jurecic, R., et al., "Long-distance DD-PCR and cDNA microarrays," Curr. Opin. Mocrobiol., 2000, 3, 316-321.

Kabanov, A.V.,"A new class of antivirals: antisense olgonucleotides combined with a hydrophobic substituent effectively inhibit influenza virus reproduction and synthesis of virus-specific proteins in MDCK cells", FEBS Letts., 1990, 259, 327-330.

Kadonaga, J.T. and Tjian, R.,"Affinity purification of sequence-specific DNA binding proteins", Proc. Natl. Acad. Sci. USA, 1986, 83, 5889-5893.

Kadonaga, J.T., "Purification of Sequence-Specific Binding Proteins b DNA Affinity Chromatography", Methods in Enzymology, 1991, 208, 10-23.

Kasher, et al., "Rapid Enrichment of HeLa Trancription Factors IIIB and IIIC by Using Affinity Chromatography Based on Avidin-Biotin Interactions", Mol. And Cell. Biol., 1986, 6, 3117-3127.

Kawaguchi, et al., "Purification of DNA-binding transcription factors by their selective adsorption of the affinity atex particles", Nucleic Acids Research, 1989, 17, 6229-6240.

Kawasaki, et al., "Synthesis and Biophysical Studies of 2'-dRIBO-2'-F Modified Oligonucleotides", Conf. on Nucleic Acid Therapeutics, Clearwater, FL, Jan. 13-16, 1991, 10 pages.

Kawasaki, et al., "Uniformly Modified 2'-Deoxy-2'-fluoro Phosphorothioate Oligonucleotides as Nuclease-Resistant Antisense Compounds with High Affinity and Specificity for RNA Targets", J. Med. Chem., 1993, 36, 831-841.

Kawasaki, H/ et al., "Hes1 is a target of MicroRNA-23 during retinoic-acid-induced neuronal differentiation of NT2 cells," Nature (2003) 423: 838-842.

Kennedy, "Hydrophobic Chromatography", Methods in Enzymology, 1990, 182, 339-343.

Khurshid et al., "The unique conformational stability of poly 2'-O-Ethyladenylic Acid," FEBS Letters, 1972, 28(1), 25.

Khvorova, A. et al., "Functional siRNAs Exhibit Strand Bias," Cell, 2003, 115(2), 209-216.

Kiaris, H. et al., "Antagonists of Growth Hormone-Releasing Hormone Inhibit the Growth of U-87MG Human Gliobastoma in Nude mice," Neoplasia, 2000, 2(3), 242-250.

Kielanowska et al., "Preparation and properties of poly 2'-O-ethylcytidylic acid," Nucl. Acids Res., 1976, 3(3), 817-824.

Kimura-Harada, "5-methyl-2-thiouridine: A new sulfur-containing minor constituent from rat liver glutamic acid and lysine tRNAs," FEBS Lett., 1971, 13, 335-338.

Kingston, R.E. et al., "Calcium Phosphate Transfection", Current Protocols in Neuroscience, 1997, Supplement 1, A.1C.1-A.1C.8.

Klopffer, A.E. et al., "Synthesis of 2'-Aminoalkyl-Substituted Fluorinated Nucleobases and Their Influence on the Kinetic Properties of Hammerhead Ribozymes," ChemBioChem (2004) 5: 707-716.

Klopffer, A.E. et al., "The effect of universal fluorinated nucleobases on the catalytic activity of ribozymes ," Nucleosides Nucleotides Nucleic Acids (2003) 22(5-8): 1347-1350.

Knecht, D., "Application of Antisense RNA to the Study of the Cytoskeleton: Background, Principles, and a Summary of Results Obtained with Myosin Heavy Chain", Cell Motil. Cytoskel., 1989, 14, 92-102.

Knochbin et al., "An antisense RNA involved in p53 mRNA maturation in murine erythroleukemia cells induced to differentiate", EMBO J., 1989, 8, 4107-4114.

Knorre, et al., "Complementary-Addressed Sequence-Specific Modification of Nucleic Acids", Progress in Nucleic Acid Research and Molecular Biology 1985, 32, 291-321.

Koizumi, M. et al., "Design of RNA enzymes distinguishing a single base mutation in RNA," Nucleic Acids Research, 1989, 17, 7059-7071.

Koole, et al., "Synthesis of phosphate-methylated DNA fragments using 9-fluorenylmethoxycarbonyl as transient base protecting group", J. Org. Chem., 1989, 54, 1657-1664.

Koshkin, A.A., et al., "LNA (locked nucleic acid): an RNA mimic forming exceedingly stable LNA:LNA duplexes," J. Am. Chem. Soc., 1998, 120, 13252-13253.

Koshkin, A.A., et al., "LNA (locked nucleic acids): synthesis of the adenine, cytosine, guanine, 5-methylcytosine, thymine and uracil bicyclonucleoside monomers, oligomerisation, and unprecedented nucleic acid recognition," Tetrahedron, 1998, 54, 3607-3630.

Kraynack, B.A. et al., "Small interfering RNAs containing full 2'-O-methylribonucleotide-modified sense strands display Argonaute2/eIF2C2-dependent activity," RNA, 2006, 12, 163-176.

Krieg, A. M. et al., "Uptake of Oligodeoxyribonucleotides by Lymphoid Cells Is Heterogeneous and Inducible," Antisense Research and Development (1991) 1:161-171.

Krinke, L. et al., "RNase III-dependent hybrolysis of ÿcII-O gene mRNA mediated by ÿ OOP antisense RNA", Genes & Devel., 1990, 4, 2223-2233.

Kroschwitz, J.I. (Ed.), The Concise Encyclopedia of Polymer Science and Engineering, John Wiley & Sons, 1990, 858-859.

Krug, A., et al., "Synthesis of oligonucleotide probes containing 2'-deoxy-2'-fluoronucleosides for cleavage of RNA by RNase H," Biomed. Biochem. Acta, 1990, 49, 161-166.

Krug, A., et al., "The behaviour of 2'-deoxy-2'-fluorouridine incorporated into oligonucleotides by the phosphoramidite approach," Nucleosides & Nucleotides, 1989, 8(8), 1473-1483.

Krystal et al., "N-myc mRNA Forms an RNA-RNA Duplex with Endogenous Antisense Transcripts", Mol. And Cell. Biol., 1990, 10, 4180-4191.

Kuijpers, W. H. A. et al., "Specific Recognition of Antibody-Oligonucleotide Conjugates by Radiolabeled Antisense Nucleotides: A Novel Approach for Two-Step Radioimmunotherapy of Cancer," Bioconjugate Chem. (1993) 4(1):94-102.

Kuimelis, "Synthesis of oligodeoxynucleotides containing 2-thiopyrimidine residues—a new protection scheme," Nucleic Acids Res. 1994, 22(8), 1429-1436.

Kumar et al., "Antisense RNA: function and fate of duplex RNA in cells of higher eukaryotes," Microbiology and Molecular Biology Reviews (1998) 62(4): 1415-1434.

Kumar, R., et al., "The first analogues of LNA (locked nucleic acids): phosphorothioate-LNA and 2'-thio-LNA," Bioorg. Med. Chem. Lett., 1998, 8, 2219-2222.

Kurchavov, N. A., et al., "A new phosphoramidite reagent for the incorporation of diazaphenoxazinone nucleoside with enhanced base-pairing properties into oligodeoxynucleotides," Nucleosides and Nucleotides, 1997, 16, 1837-1846.

Kurreck, J., "Antisense technologies, Improvement through novel chemical modifications," Eur. J. Biochem., 2003, 270(8), 1628-1644.

Kusmierek et al., "Alkyation of cytidine-5'-phosphate: Mechanisms of alkylation, influence of O'-alkylation on susceptibility of pyrimidine nucleotides to some nucleolytic enzymes, and synthesis of 2'-O-alkyl polynucleotides," ACTA Biochim. Polonica, 1973, 20(4), 365-381.

Lacerra, G., et al., "Restoration of hemoglobin a synthesis in erythroid cells from peripheral blood of thalassemic patients," Proc. Natl. Acad. Sci. USA, Aug. 15, 2000, 97(17), 9591-9596.

Lai J. S. et al., "Fluorinated DNA Bases as Probes of Electrostatic Effects in DNA Base Stacking," Angew. Chem. Int. Ed. (2003) 42: 5973-5977.

Lai, J. S. et al., "Selective Pairing of Polyfluorinated DNA Bases," J. Am. Chem. Soc. (2004) 126(10): 3040-3041.

Lane, A. N. et al., "NMR Assignments and Solution Conformation of the DNA-RNA Hybrid Duplex d(GTGAACTT)-r(AAGUUCAC)," Eur. J. Biochem., 1993, 215, 297-306.

Larson, E.J., et al., "Rapid DNA fingerprinting of pathogens by flow cytometry," Cytometry, 2000, 41, 203-208.

Larsson, M., et al., "High-throughput protein expression of cDNA products as a tool in functional genomics," J. Biotechnol., 2000, 80, 143-157.

Le Doan et al., "Sequence-Targeted Chemical Modifications of Nucleic Acids by Complementary Oligonucleotides Covalently Linked to Porphyrins", Nucleic Acid Research, 1987, 15, 8643-8659.

Lee, R.C. et al., "The C. elegans heterochronic gene lin-4 encodes small RNAs with antisense complementarity to lin-14," Cell, 1993, 75(5), 843-854.

Lee, K. et al., "Ring-Constrained (N)-Methanocarba Nucleosides as Adenosine Receptor Agonists: Independent 5'-Uronamide and 2'-Deoxy Modifications," Bioorganic & Medicinal Chemistry Letters, 2001, 11(10), 1333-1337.

Lee, Y. et al., "MicroRNA maturation: stepwise processing and subcellular localization," EMBO J. (2002) 21(17): 4663-4670.

Lee, Y. et al., "The nuclearRNase III Drosha initiates microRNA processing," Nature (2003) 425: 415-419.

Lengyel, P., "Double-stranded RNA and interferon action," J. Interferon Res., 1987, 7, 511-519.

Lesnik, E.A. et al., "Relative thermodynamic stability of DNA, RNA, and DNA:RNA hybrid duplexes: relationship with base composition and structure," Biochemistry, 1995, 34, 10807-10815.

Letsinger et al., "Effects of Pendant Groups at Phosphorus on Binding Properties of D-ApA Analogues", Nucleic Acids Research, 1986, 14, 3487-3499.

Letsinger, R.L. et al., "Cholesteryl-conjugated oligonucleotides: Synthesis, properties and activity as inhibitors of replication of human immunodeficiency virus in cell culture," Proc. Natl. Acad. Sci.,1989, 86, 6553-6556.

Li, S. et al., "Folate-Mediated Targeting of Antisense Oligodeoxynucleotides to Ovarian Cancer Cells," Pharm. Res. (1998) 15(10):1540-1545.

Liao, "A pyrimidine-guanine sequence-specific ribonuclease from Rana catesbeiana (bullfrog) oocytes", Nucl. Acids Res., 1992, 20, 1371-1377.

Lima, W. F. et al., "Highly efficient endonucleolytic cleavage of RNA by a CyszHisz zinc-finger peptide," Proc. Natl. Acad. Sci. USA (1999) 96:10010-10015.

Lima, W.F. et al., "Binding affinity and specificity of *Escherichia coli* RNase H1: impact on the kinetics of catalysis of antisense oligonucleotide-RNA hybrids," Biochemistry, vol. 36, pp. 390-398 (1997).

Limbach, P.A. et al., "Summary: the modified nucleosides of RNA," Nucleic Acids Res., 1994, 22(12), 2183-2196.

Lin, K.-Y. et al., "A Cytosine Analogue Capable of Clamp-Like Binding to a Guanine in Helical Nucleic Acids," J. Am. Chem. Soc., 1998, 120(33), 8531-8532.

Lin, K.-Y. et al., "Tricyclic 2'-Deoxycytidine Analogs: Synthesis and Incorporation into Oligodeoxynucleotides Which Have Enhanced Binding to Complementary RNA," J. Am. Chem. Soc., 1995, 117, 3873-3874.

Lin, M. et al., "Inhibition of collagenase type I expression by psoralen antisense oligonucleotides in dermal fibroblasts," Faseb J. 1995, 9, 1371-1377.

Lipardi, C., et al., "RNAi as random degradative PCR: siRNA primers convert mRNA into dsRNAs that are degraded to generate new siRNAs," Cell, 2001, 107, 297-307.

Liu, H. et al. "A Four Base Paired Genetic Helix with Expanded Size," Science (2003) 302; 868-871.

Liu, H. et al., "Toward a New Genetic System with Expanded Dimensions: Size-Expanded Analogues of Deoxyadenosine and Thymidine," J. Am Chem Soc. (2004) 126(4) 1102-1109.

Liu, K. et al., "Efficient Nuclear Delivery of Antisense Oligodeoxynucleotides and Selective Inhibition of CETP Expression by Apo E Peptide in a Human CETP-Stably Transfected CHO Cell Line," Arterioscler. Thromb. Vasc. Biol. (1999) 19:2207-2213.

Lixin, R. et al., "Novel Properties of the Nucleolar Targeting Signal of Human Angiogenin," Biochem. Biophys. Res. Comm. (2001) 284:185-193.

Loakes, D. et al., "The applications of universal DNA base analogues," Nucleic Acids Res., 2001, 29(12), 2437-2447.

Lohrmann et al.,"New Solid Supports for DNA Synthesis", DNA, 1984, 3, 122.

Lukhtanov, E. A. et al., "Direct, Solid Phase Assembly of Dihydropyrroloindole Peptides with Conjugated Oligonucleotides," Bioconjugate Chem. (1996) 7(5):564-567.

Lund et al., "Assessment of methods for covalent binding of nucleic acids to magnetic beads, Dynabeads™, and the characteristics of the bound nucleic acids in hybridization reactions", Nucl. Acids Res., 1988, 16, 10861-10880.

Madden, S.L., et al., "Serial analysis of gene expression: from gene discovery to target identification," Drug Discov. Today, Sep. 2000, 5(9), 415-425.

Mahato et al., "Modulation of gene expression by antisense and antigene oligodeoxynucleotides and small interfering RNA," Expert Opinion on Drug Delivery, Jan. 2005, 2(1), 3-28.

Manche et al., "Interactions between double-stranded RNA regulators and the protein kinase DAI," Mol. Cell Biol., 1992, 12(11), 5238-5248.

Maniak, M. et al., "Evidence for a feedback regulated back-up promoter which controls permanent expression of a Dictyostelium gene", Nucl. Acids Res., 1990, 18, 5375-5380.

Manoharan M. et al., "Cholic Acid-Oligonucliotide Conjugates for Antisense Applications", Bioorganic Med. Chem. Letts., 1994, 4, 1053-1060.

Manoharan M. et al., "Oligonucleotide Conjugates: Alteration of the Pharmacokinetic Properties of Antisense Agents", Nucleosides and Nucleotides, 1995, 14, 969-973.

Manoharan, M. et al., "Chemical Modifications to Improve Uptake and Bioavailability of Antisense Oligonucleotides", Annals NY Acad. Sciences, 1992, 660, 306-309.

Manoharan, M. et al., "Introduction of a Lipophilic Thioether Tether in the Minor Groove of Nucleic Acids for Antisense Applications," Bioorg. Med. Chem. Letts., 1993, 3, 2765-2770.

Manoharan, M. et al., "Novel Functionalization of the Sugar Moiety of Nucleic Acids for Multiple Labeling in the Minor Groove," Tetrahedron Letters (1991) 32(49):7171-7174.

Manoharan, M. et al., "Lipidic Nucleic Acids", Tetrahedron Letts., 1995, 36, 3651-3654.

Manoharan, M., "2'-Carbohydrate modifications in antisense oligonucleotide therapy: importance of conformation, configuration and conjugation," Biochimica et Biophysica Acta, 1999, 1489, 117-130.

Manoharan, M., "Designer Antisense Oligonucleotides: Conjugation Chemistry and Functionality Placement," Antisense Research and Applications, Crooke and Lebleu, eds., CRC Press Boca Raton. FL, 1993, Chapter 17, 303-349.

Manoharan, M., "Oligonucleotide Conjugates as Potential Antisense Drugs with Improved Uptake, Biodistribution, Targeted Delivery and Mechanism of Action," Antisense & Nucleic Acid Drug Development (2002) 12:103-128.

Manoharan, M., "Oligonucleotide Conjugates in Antisense Technology," Antisense Drug Technology, Principles, Strategies, and Applications, Crooke, S. T. ed., Marcel Dekker, New York, (2001) Chapter 16, 391-467.

Manoharan, M., "RNA interference and chemically modified small interfering RNAs," Current Opinion in Chemical Biology, 2004, 8, 570-579.

Marcus-Sekura, "Comparative inhibition of chloramphenicol acetyltransferase gene expression by antisense oligonucleotide analogues having alkyl phosphotriester, methylphosphonate and phosphorothioate linkages", Nucleic Acids Res., 1987, 15, 5749-5763.

Marcus-Sekura, "Techniques for Using Antisense Oligodeoxyribonucleotides to Study Gene Expression", Anal. Biochemistry, 1988, 172, 289-295.

Markiewicz, et al., "Simultaneous Protection of 3'- and 5'-Hydroxyl Groups of Nucleosides", Nucleic Acid Chemistry, Part 3, pp. 229-231, L.B. Townsend, et al., Eds., J. Wiley and Sons, New York, 1986, 229-231.

Martin, "Ein neuer Zugang zu 2'-O-Alkylribonucleosiden und Eigenschaften deren Oligonucleotide", Helv. Chim. Acta., 1995, 78, 486-504.

Martinez, J., et al., "Single-stranded antisense siRNAs guide target RNA cleavage in RNAi," Cell, 2002, 110, 563-574.

Maruenda, H. et al., "Antisense Sequence-Directed Cross-Linking of DNA Oligonucleotides by Mitomycin C," Bioconjugate Chem. (1996) 7(5):541-544.

Maruenda, H. et al., "Antisense sequence-directed cross-linking of RNA oligonucleotides by mitomycin," Anti-Cancer Drug. Des. (1997) 12, 473-479.

Maskos, U. And Southern, E.M., "Oligonucleotide hybridisations on glass supports: a novel linker for oligonucleotide synthesis and hybridisation properties of oligonucleotides synthesised in situ", Nucl. Acids. Res., 1992, 20, 1679-1684.

Matson, et al., "Biopolymer Synthesis on Polypropylene Supports", Anal. Biochem., 1994, 217, 306-310.

Matsukura, M. et al., "Phosphorothioate Analogs of Oligodeoxynucleotides: Inhibitors of Replication and Cytopathic Effects of Human Immunodeficiency Virus", Proc. Natl. Acad. Sci. USA, 1987, 84, 7706-7710.

Matteucci, M.D. et al., "Synthesis of Deoxyoligonucleotides on a Polymer Support," J. Am. Chem. Soc., 1981, 103(11), 3185-3191.

McBride, L.J. and Caruthers, M.H., "An Investigation of Several Deoxynucleoside Phosphoramidites Useful for Synthesizing Deoxyoligonucleotides", Tetrahedron Letters, 1983, 24, 245-248.

Meegan, J.M. et al., "Double-Stranded Ribonuclease Coinduced with Interferon", Science, 1989, 244, 1089-1091.

Mellitzer et al., "Spatial and temporal 'knock down' of gene expression by electroporation of double-stranded RNA and morpholinos into early postimplantation mouse embryos," Mechanisms of Development, 2002, 118(1-2), 57-63.

Metelev, V. et al., "Study of antisense oligonucleotide phosphorothioates containing segments of oligodeoxynucleotides and 2'-o-methyloligoribonucleotides," Bioorg. & Med. Chem. Letts., 1994, 4(24), 2929-2934.

Meunier, L. et al., "The nuclear export signal-dependent localization of oligonucleopeptides enhances the inhibition of the protein expression from a gene transcribed in cytosol," Nucleic Acids Res. 1999, 27(13):2730-2736.

Meyer, et al., "Efficient, Specific Cross-Linking and Cleavage of DNA by Stable, Synthetic Complementary Oligodeoxynucleotides", J. Am. Chem. Soc. 1989, 111, 8517-8519.

Mili, S. et al., "Distinct RNP Complexes of Shuttling hnRNP Proteins with Pre-mRNA and rnRNA. Candidate Intermediates in Formation and Export of mRNA," Mol. Cell Biol. (2001) 21(21):7307-7319.

Miller, et al., "A New Approach to Chemotherapy Based on Molecular Biology and Nucleic Acid Chemistry: Matagen (Masking Tape for Gene Expression", Anti-Cancer Drug Design, 1987, 2, 117-128.

Miller, et al., "Biochemical and Biological Effects of Nonionic Nucleic Acid Methylphosphonates", Biochemistry 1981, 20, 1874-1880.

Miller, et al., "Nonionic nucleic acid analogues. Synthesis and characterization of dideoxyribonucleoside methylphosphonates", Biochemistry 1979, 18, 5134-5143.

Miller, et al., "Synthesis and properties of adenine and thymine nucleoside alkyl phosphotriesters, the neutral analogs of dinucleoside monophosphates", J. Am. Chem. Soc. 1971, 93, 6657-6664.

Milligan, "Current concepts in antisense drug design," J. Med. Chem., 1993, 36, 1923-1937.

Min, K. -L. et al., "Oligonucleotides comprised of alternating 2'-deoxy-2'-fluoro-beta-D-arabinonucleosides and D-2'-deoxyribonucleosides (2'F-ANA/DNA 'Altimers') induce efficient RNA cleavage mediated by RNase H," Bioorganic & Medicinal Chemistry Letters, Sep. 2002, 12, 2651-2654.

Mishra et al., "Improved leishmanicidal effect of phosphorotioate antisense oligonucleotides by LDL-medicated delivery", Biochim. Biophys. Acta, 1995, 1264, 229-237.

Miura et al., "Fluorometric determination of total mRNA with oligo(dT) immobilized on microtiter plates", Clin. Chem., 1996, 42(11), 1758-1764.

Monia, et al., "Antitumor activity of a phosphorothioate antisense oligodeoxynucleotide targeted against c-raf kinase", Nature Medicine, 1996, 2, 668-675.

Monia, et al., "Evaluation of 2'-Modified Oligonucleotides Containing 2'-Deoxy Gaps as Antisense Inhibitors of Gene Expression", J. Biol. Chem., 1993, 268, 14514-14522.

Monia, et al., "Selective Inhibition of Mutant Ha-ras mRNA Expression by Antisense Oligonucleotides", J. Biol. Chem., 1992, 267, 19954-19962.

Montgomery, M.K. et al., "RNA as a target of double-stranded RNA-mediated genetic interference in Caenorhabditis elegans," Proc. Natl. Acad. Sci. USA, 1998, 95(26), 15502-15507.

Moran, S. et al., "A thymidine triphosphate shape analog lacking watson-crick pairing ability is replicated with high sequence selectivity," Proc. Natl. Acad. Sci. USA (1997) 94, 10506-10511.

Moran, S. et al., "Difluorotoluene, a Nonpolar Isostere for Thymine, Codes Specifically and Efficiently for Adenine in DNA Replication," J Am Chem Soc. (1997) 119(8) 2056-2057.

Morita, K. et al., "2'-O,4'-C-Ethylene-Bridged Nucleic Acids (ENA): Highly Nuclease-Resistant and Thermodyamically Stable Oligonucleotides for Antisense Drug," Bioorganic & Medicinal Chemistry Letters, 2002, 12(1), 73-76.

Morita, K. et al., "Synthesis and Properties of 2'-O,4'-C-Ethylene-Bridged Nucleic Acids (ENA) as Effective Antisense Oligonucleotides," Bioorg. Med. Chem., 2003, 11, 2211-2226.

Moulds, C. et al., "Site and Mechanism of Antisense Inhibition by C-5 Propyne Oligonucleotides," Biochemistry, 1995, 34(15), 5044-5053.

Napoli, C. et al., "Introduction of a Chimeric Chalcone Synthase Gene into Petunia Results in Reversible Co-Suppression of Homologous Genes in trans," Plant Cell, 1990, 2(4), 279-289.

Narhi, et al., "Hydrophobic Interaction Chromatography in Alkaline pH", Anal. Biochem., 1989, 182, 266-270.

Nasevicius, A. et al., "Effective targeted gene 'knockdown' in zebrafish," Nature Genetics, 2000, 26, 216-220.

Nellen, W., C., "What makes an mRNA anti-sense-itive?", Curr. Opin. Cell. Biol., 1993, 18, 419-424.

Nellen, W., et al., "Mechanisms of gene regulation by endogenous and artificially introduced antisense RNA", Biochem., Soc. Trans., 1992, 20, 750-754.

Nelson, P. S. et al., "Bifunctional oligonucleotide probes synthesized using a novel CPG support are able to detect single base pair mutations," Nucleic Acids Res. (1989) 17(18):7187-7194.

Nielsen et al., "Sequence-Selective Recognition of DNA by Strand Displacement with a Thymine-Substituted Polyamide", Science, 1991, 254, 1497-1500.

Nishikura, K. et al., "A Short Primer on RNAi: RNA-Directed RNA Polymerase Acts as a Key Catalyst," Cell, 2001, 107(4), 415-418.

Nitta, et al., "Purification and Some Properties of Ribonuclease from *Xenopus laevis* Eggs", Biol. Pharm. Bull. (Jpn.), 1993, 16, 353-356.

Noguchi, et al., "Characterization of an Antisense Inr Element in the eIF-2α Gene", J. Biol. Chem., 1994, 269, 29161-29167.

Noyes, et al., "Nucleic Acid Hybridization Using DNA Covalently Coupled to Cellulose", Cell, 1975, 5, 301-310.

Oberhauser et al., "Effective incorporation of 2'-O-methyl-oligonucleotides into liposomes and enhanced cell association through modification with thiocholesterol", Nucl. Acids Res., 1992, 20(3), 533-538.

Ogilvie, K.K. et al., "The Use of Silyl Groups in Protecting the Hydroxyl Functions of Ribonucleosides," Tetrahedron Letters, 1974, 15(33), 2861-2863.

Ohtsuka et al., "Recognition by Restriction Endonuclease EcoRI of Deoxyoctanucleotides containing modified sugar moieties," Eur. J. Biochem., Mar. 1984, 447-450.

Ohtsuki, et al., "Isolation and purification of double-stranded ribonuclease from calf thymus", J. Biol. Chem., 1977, 252, 483-491.

Olsen, D.B., et al., "Study of a Hammerhead Ribozyme Containing 2'-Modified Adenosine Residues," Biochemistry, 1991, 30:, 9735-9741.

O'Neill, B.M. et al., "A Highly Effective Nonpolar Isostere of Deoxyguanosine: Synthesis, Structure, Stacking, and Base Pairing," J. Org. Chem. (2002) 67(17):5869-5875.

Opalinska et al., "Nucleic-acid therapeutics: basic principles and recent applications," Nature Review, 2002, 1, 503-514.

Ørum, H. et al., "Locked nucleic acids: A promising molecular family for gene-function analysis and antisense drug development," Curr. Opin. Mol. Therap., 2001, 3(3), 239-243.

Outten, et al., "Synthetic 1-methoxybenzo[d]naphtho[1,2-b]pyran-6-one c-glycosides", J. Org. Chem. 1987, 52, 5064-5066.

Owen, et al., "Transcriptional activation of a conserved sequence element by ras requires a nuclear factor distinct from c-fos or c-jun", Proc. Natl. Acad. Sci USA, 1990, 87, 3866-3870.

Owen, G.R. et al., "4'-Substituted Nucleosides. 3. Synthesis of Some 4'-Fluorouridine Derivatives," J. Org. Chem., 1976, 41(18), 3010-3017.

Paddison, P.J., et al., "Stable suppression of gene expression by RNAi in mammalian cells," PNAS, 2002, 99(3), 1443-1448.

Parker, J.S. et al., "Structure insights into mRNA recognition from a PIWI domain-siRNA guide complex," Nature, 2005, 434, 663-666.

Parkes, et al., "A short synthesis of 3'-cyano-3'-Deoxythymidine", Tetra. Lett., 1988, 29, 2995-2996.

Parr, W. et al., "Solid-Phase Peptide Synthesis on an Inorganic Matrix having Organic Groups on the Surface," Angew Chem. Internat. Edit, 1972, 11 (4), 314-315.

Parrish, S. et al., "Functional Anatomy of a dsRNA Trigger: Differential Requirement for the Two Trigger Strands in RNA Interference," Molecular Cell, 2000, 6, 1077-1087.

Patzel et al., "A Theoretical Approach to Select Effective Antisense Oligodeoxyribonucleotides at High Statistical Probability," Nucleic Acids Research (1999) pp. 4328-4334.

Pease, et al., "Light-generated oligonucleotide arrays for rapid DNA sequence analysis", Proc. Natl. Acad. Sci. USA, 1994, 91, 5022-5026.

Peracchi, A., "Prospects for antiviral ribozymes and deoxyribozymes," Rev. Med. Virol., vol. 14, pp. 47-64 (2004).

Petersen, M. et al., "The conformations of locked nucleic acids (LNA)," J. Mol. Recognit., 2000, 13, 44-53.

Petersheim, et al., "Base-Stacking and Base-Pairing contributions to helix stability: thermodynamics of double-helix formation with CCGG, CCGGp, CCGGAp, ACCGGp, CCGGUp, and ACCGGUp", Biochemistry, 1983, 22, 256-263.

Pichon, C. et al., "Intracellular Routing and Inhibitory Activity of Oligonucleopeptides Containing a KDEL Motif," Mol. Pharmacol. (1997) 51:431-438.

Pieken, W.A. et al., "Kinetic Characterization of Ribonuclease-Resistant 2'-Modified Hammerhead Ribozymes," Science, 1991, 253, 314-317.

Pieken, W.A., et al., "Structure-Function Relationship of Hammerhead Ribozymes as Probed by 2'-Modifications," Nucleic Acids Symp Ser., 1991, 24, 51-53.

Pike et al., "Mixed Alkylation (Methylation and Ethylation) of Adenosine by Diazoethane in Aqueous 1,2-Dimethoxyethane," J. Org. Chem., 1974, 39(25), 3674-3676.

Pilet, J. et al., "Structural parameters of single and double helical polyribonucleotides," Biochem Biophys Res Commun, 1973, 52(2), 517-523.

Pitts, A.E. et al., "Inhibition of human telomerase by 2'-O-methyl-RNA," Proc. Natl. Acad. Sci. USA, 1998, 95, 11549-11554.

Pon, et al., "Derivatization of Controlled Pore Glass Beads for Solid Phase Oligonucleotide Synthesis", BioTech., 1988, 6, 768-773.

Poopeiko, N. E. et al., "*Xylo*-configured Oligonucleotides (XNA, Xylo Nucleic Acid): Synthesis of Conformationally Restricted Derivatives and Hybridization Towards DNA and RNA Complements," Biorganic & Medicinal Chemistry Letters 2003, vol. 13, pp. 2285-2290.

Porta, H. et al., "An allosteric hammerhead ribozyme," Biotechnology (N.Y.), 1995, 13(2), 161-164.

Prakash, T. P. et al., Abstract of The 227th ACS National Meeting, Anaheim,CA, Mar. 28-Apr. 1, 2004.

Prakash, T. P. et al., "Synthesis of Site-Specific Oligonucleotide-Polyamine Conjugates," Bioorg. Med. Chem. Lett. (1994) 4(14):1733-1738.

Prashar, Y., et al., "A method for display of 3'-end fragments of restriction enzyme-digested cDnAs for analysis of differential gene expression," Methods Enzymol., 1999, 303, 258-272.

Prokipcak, et al., "Purification and Properties of a Protein that Binds to the C-terminal Coding Region of Human c-myc mRNA", J. Biol. Chem., 1994, 269, 9261-9269.

Puglisi, et al., "Absorbance melting curves of RNA", Methods in Enzymology, 1989, 180, 304-325.

Rajur, S. B. et al., "Covalent Protein-Oligonucleotide Conjugates for Efficient Delivery of Antisense Molecules," Bioconjugate Chem. (1997) 8(6):935-940.

Rajwanshi, V.K., et al., "LNA stereoisomers: xylo-LNA (β-D-xylo configured locked nucleic acid) and α-L-ribo configured locked nucleic acid)," Chem. Commun., 1999, 1395-1396.

Ranganathan, "Modification of the 21-Position of Purine Nucleosides: Synthesis of 21-a-Substituted-21-Deoxyadenosine Analogs", Tetrahedron Letters, 1977, 15, 1291-1294.

Ransford et al., "2'-O-Ethyl Pyrimidine Nucleosides," J. Carbohydrates—Nucleosides—Nucleotides, 1974, 1(3), 275-278.

Rao, et al., "A Novel One-step Procedure for the Conversion of Thymidine into 2,3'-Anhydrothymidine", J. Chem. Soc. Chem. Commun., 1989, 997-998.

Rausch, J.W. et al., "Hydrolysis of RNA/DNA hybrids containing nonpolar pyrimidine isosteres defines regions essential for HIV type 1 polypurine tract selection," PNAS (2003) 100(20): 11279-11284.

Reddy, M.P. et al., "Fast Cleavage and Deprotection of Oligonucleotides," Tetrahedron Letters, 1994, 35(25), 4311-4314.

Reese, C.B. et al., "An Acetal Group Suitable for the Protection of 2'hydroxy Functions in Rapid Oligoribonucleotide Synthesis," Tetrahedron Letters, 1986, 27(20), 2291-2294.

Reese, C.B., et al., "4-(1,2,4-Triazol-1-yl)-and 4-(3-Nitro-1,2,4-triazol-1-yl)-1-(β-D-Arabinofuranosyl)cytosine(Ara-C)", J. Chem. Soc. Perkin Trans. I, 1982, pp. 1171-1176.

Renneberg, D. et al. "Antisense properties of tricyclo-DNA," Nucleic Acids Res., 2002, 30(13), 2751-2757.

Renneberg, D., et al., "Watson—Crick base-pairing properties of tricycle-DNA," J. Am. Chem. Soc., 2002, 124, 5993-6002.

Revankar et al., "Synthesis and Antiviral/Antitumor of Certain 3-Seazaguanine Nucleosides and Nucleotides", J. Med. Chem. 1984, 24, 1389-1396.

Rhodes, J. et al., "Therapeutic potentation of the immune system by costimulatory Schiff-baseforming drugs," Nature (1995) 377(6544):71-75.

Robins, et al., "Nucleic acid related compounds. 41. Restricted furanose conformations of 3',5'-O(1,1,3,3-tetraisoprpyldisilox-1,3-diyl)nucleosides provide a convenient evaluation of anomeric configuration1,2", Can. J. Chem., 1983, 61, 1911-1920.

Robins, et al., "Nucleic Acid Related Compounds. 42. A General Procedure for the Efficient Deoxygenation of Secondary Alcohols. Regiospecific and Stereoselective Conversion of Ribonucleosides to 2'-Deoxynucleosides", J. Am. Chem. Soc., 1983, 105, 4059-4065.

Robins, et al., "Synthesis of 2'-Deoxytubercidin, 2'-Deoxyadenosine, and Related 2'-Deoxynucleosides via a Novel Direct Stereospecific Sodium Salt Glycosylation Procedure", J. Am. Chem. Soc., 1984, 106, 6379-6382.

Roelen et al., "Synthesis of Nucleic Acid Methylphos-Phonothioates", Nucleic Acids Research 1988, 16(15), 7633-7645.

Rottman et al., "Influence of 2'-O-Alkylation on the Structure of Single-Stranded Polynucleotides and the Stability of 2'-O-Alkylated Polynucleotide Complexes," Biochem., 1974, 13, 2762-2771.

Rottman, F. et al., "Polymers Containing 2'-O-Methylnucleotides. II. Synthesis of Heteropolymers," Biochem, 1969, 8(11), 4354-4361.

Rottman, F. et al., "Polynucleotides Containing 2'-0-Methyladenosine. I. Synthesis by Polynucleotide Phosphorylase," Biochem, 1968, 7, 2634-2641.

Ruby, et al., "An Early Hierarchic Role of U1 Small Nuclear Ribonucleoprotein in Splicesome Assembly", Science, 1988, 242, 1028-1035.

Rump, E. T. et al., "Preparation of Conjugates of Oligodeoxynucleotides and Lipid Structures and Their interaction with Low-Density Lipoprotein," Bioconjugate Chem. (1998) 9(3):341-349.

Ryan, et al., "Synthesis of 2-Thio-D-ribose and 2'-Thioadenosine Derivatives", J. Org. Chem., 1971, 36(18), 2646-2657.

Saison-Behmoaras, T., et al., "Short modified antisense oligonucleotides directed against Ha-ras point mutation induce selective cleavage of the mRNA and inhibit T24 cells proliferation", EMBO, 1991, 10, 1111-1118.

Saito, H. And Richardson, C., "Processing of mRNA by Ribonuclease III Regulates Expression of Gene 1.2 of Bacteriophage T7", 1981, Cell, 27, 533-542.

Sambrook, et al., "Molecular Cloning. A Laboratory Manual", Cold Spring Harbor Laboratory Press, 1989, vol. 2, pp. 11.31-11.32.

San et al., "Safety and short term toxicity of a novel cationic lipid formulation for human gene therapy", Human Gene Therapy, 1993, 4, 781-788.

Sands, et al., Biodistribution and Metabolism of Internally 3H-Labeled Oligonucleotides. II. 3',5'-Blocked Oligonucleotides, Mol. Pharmacol., 1995, 47, 636-646.

Sanghvi, Y.S. et al., "Heterocyclic Base Modifications in Nucleic acids and their Applications in Antisense Oligonucleotides", Antisense Research and Applications, CRC Press, Boca Raton, Chapter 15, 1993, 273-288.

Scaringe, S.A. et al., "Novel RNA Synthesis Method Using 5'-O-Silyl-2'-O-orthoester Protecting Groups," J. Am. Chem. Soc., 1998, 120(45), 11820-11821.

Scaringe, S.A., "RNA Oligonucleotide Synthesis via 5'-Silyl-2'-Orthoester Chemistry," Methods, 2001, 23, 206-217.

Scaringe, S.A., Thesis entitled, "Design and Development of New Protecting Groups for RNA Synthesis," University of Colorado (1996).

Scherer et al., "Approaches for the sequence-specific knockdown of mRNA," Nat. Biotechnol., 2003, 21(12), 1457-1465.

Schöning, K.-U., et al., "Chemical etiology of nucleic acid structure: the α-threofuranosyl-(3'→2') oligonucleotide system," Science, 2000, 290, 1347-1351.

Schott, "Template-Chromatographie an Stationar Gebundenen Oligonukleotiden", J. Chromatogr., 1975, 115, 461-476.

Schwartz, et al., "A microtransfection method using the luciferase-encoding reporter gene for the assay of human immunodeficiency virus LTR promoter activity", Gene, 1990, 88, 197-205.

Schwartz, M.E. et al., "Rapid Synthesis of Oligoribonucleotides Using 2'-O-(o-Nitrobenzyloxymethyl)-Protected Monomers," Bioorg. Med. Chem. Lett., 1992, 2(9), 1019-1024.

Schwarz, D.S. et al., "Asymmetry in the Assembly of the RNAi Enzyme Complex," Cell, 2003, 115(2), 199-208.

Searle, M. S. et al., "On the Stability of Nucleic Acid Structures in Solution: Enthalpy-Entropy Compensations, Internal Rotations and Reversibility," Nucl. Acids Res., 1993, 21(9), 2051-2056.

Seela, et al., "Palindromic Octa- and Dodecanucleotides Containing 2'-Deoxytubercidin: Synthesis, Hairpin Formation, and Recognition by the Endodeoxyribonuclease", Biochemistry, 1987, 26, 2232-2238.

Seliger, H., et al., "Synthetic Oligonucleotides for Biomedical Applications," Nucleic Acids Symp Ser., 1991, 24:193-196.

Seliger, H., "Handelsubliche Polymere als Trager in der Oligonucleotidsynthese, 1", Die Makromolekulart Chemie, 1975, 176, 1611-1627.

Seliger, H., and Aumann, G., "Trager-Oigonucleotidsynthese an unvernetzten Copolymeren aus Vinylalkohol und N-Vinylpyrrolidon", Die Makromolekulare Chemie, 1975, 176, 609-627.

Seliger,H. And Aumann, G., "Oligonucleotide Synthesis on a Polymer Support Soluble in Water and Pyridine", Tetrahedron Letters, 1973, No. 31, 2911-2914.

Shea et al., "Synthesis, hybridization properties and antiviral activity of lipid-oligodeoxynucletide conjugates", Nucl. Acids Res., 1990, 18(13), 3777-3783.

Sheehan, D. et al., "Biochemical properties of phosphonoacetate and thiophosphonoactate oligodeoxyribonucleotides," Nucleic Acids Res., 2003, 31(14), 4109-4118.

Shi, Y., "Mammalian RNAi for the masses," Trends in Genetics (2003) 19(1): 9-12.

Shibahara, S. et al., "Inhibition of human immunodeficiency virus (HIV-1) replication by synthetic oligo-RNA derivatives," Nucl. Acids Res., 1989, 17(1), 239-252.

Shuman, S. et al., "Site-specific Interaction of Vaccinia Virus Topoisomerase I with Base and Sugar Moieties in Duplex DNA," J. Biol Chem, 1993, 268, 18943-18950.

Siddell, S.G., "RNA Hybridization to DNA Coupled with Cyanogen-Bromide-Activated Sephadex", Eur. J. Biochem., 1978, 92, 621-629.

Sigman, "Nuclease Activity of 1,10-Phenanthroline-Copper Ion", Acc. Chem. Res., 1986, 19, 180-186.

Sijen, T. et al., "On the role of RNA amplification in dsRNA-triggered gene silencing," Cell, Nov. 16, 2001, 107, 465-476.

Singer et al., "Alkylation of Ribose in RNA Reacted with Ethylnitrosourea at Neutrality," Biochem., 1976, 15(23), 5052.

Singh, S.K. et al., "LNA (locked nucleic acids): synthesis and high-affinity nucleic acid recognition," Chem. Commun., 1998, 4, 455-456.

Singh, S.K., et al., "Synthesis of 2'-amino-LNA: a novel conformationally restricted high-affinity oligonucleotide analogue with a handle," J. Org. Chem., 1998, 63, 10035-10039.

Skorski, T. et al., "Antileukemia effect of c-myc N3'P5' phosphoramidate antisense oligonucleotides in vivo," Proc. Natl. Acad. Sci. USA, 1997, 94, 3966-3971.

Smith et al., "Antiviral effect of an oligo(nucleoside methylphosphonate) complementary to the splice junction of herpes simplex virus type 1 immediate early pre-mRNAs 4 and 5", Proc. Natl. Acad. Sci. USA, 1986, 83, 2787-2791.

Smith, et al., "The synthesis of oigonucleotides containing an aliphatic amino group at the 5' terminus: synthesis of fluorescent DNA primers for use in DNA sequence analysis", Nucl. Acids Res., 1985, 13, 2399-2412.

Smith, T.F. et al., "Comparison of Biosequences," Adv. Appl. Math., 1981, 2, 482-489.

Song, E. et al., "RNA interference targeting Fas protects mice from fulmiant hepatitis," Nature Med., 2003, 9(3), 347-351.

Song, J.-J. et al., "The Crystal Structure of Argonaute and Its Implication for RISC Slicer Activity," Science, 2004, 305, 1434-1437.

Soutschek, J. et al., "Therapeutic silencing of a endogenous gene by systemic administration of modified siRNAs," Nature, 2004, 432(7014), 173-178.

Sproat, et al., "Highly Efficient Chemical Synthesis of 2'-O-methylioligoribunocleotides and Tetrabiotinylated Derivatives; Novel Probes That are Resistant to Degradation by RNA or DNA Specific Nucleases", Nucleic Acids Research, 1989, 17, 3373-3386.

Sproat, et al., "New synthetic routes to protected purine 2'-O-methylriboside-3'-O-phosphoramidites using a novel alkylation procedure", Nucleic Acids Research, 1990, 18, 41-49.

Steffens, R., et al., "168. Nucleic-acid analogs with constraint conformational flexibility in the sugar-phosphate backbone tricycle-DNA," Helv. Chim. Acta, 1997, 80, 2426-2439.

Steffens, R., et al., "Synthesis and thermodynamic and biophysical properties of tricycle-DNA," Am. Chem. Soc., 1999, 121(14), 3249-3255.

Stein, C.A. et al., Antisense Oligonucleotides as Therapeutic Agents—Is the Bullet Really Magical?, Science, 1993, 261, 1004-1012.

Stein, et al., "Oligodeoxynucleotides as Inhibitors of Gene Expression: A Review", Cancer Research, 1988, 48, 2659-2668.

Stein, et al., "Physicochemical properties of phosphorothioate oligodeoxynucleotides", Nucleic Acids Research, 1988, 16, 3209-3221.

Stolt, P. And Zillig, W., "Antisense RNA mediates transcriptional processing in an archaebacterium, indicating a novel kind of RNase activity", Mol. Microbiol., 1993, 7, 875-882.

Strickland, et al., "Antisense RNA Directed Against the 3' Noncoding Region Prevents Dormant mRNA Activation in Mouse Oocytes", Science, 1988, 241, 680-684.

Struck, "Vaccine R&D Success Rates and Development Times," Nature Biotechnology, May 1996, 14, 591-593.

Stufkens, et al., "Dynamic Jahn-Teller Effect in the Excited States of SeCl62-, SeBr62-, TeCl62- and TeBr62-", Recueil des Travaux Chimiques des Pays-Bas 1970, 89, 1185-1201.

Stull, et al., "Antigene, Ribozyme and Aptamer Nucleic Acid Drugs: Progress and Prospects", Pharm. Res., 1995, Pharm. Rev., 12, 465-482.

Suciu et al., "Synthesis of 9-(2,5-dideoxy-β-D-glycero-pent-4-enofuranosyl)adenine", Carbohydrate Research, 1975, 44, 112-115.

Sui, G., et al., "A DNA vector-based RNAi technology to suppress gene expression in mammalian cells," PNAS, 2002, 99(8), 5515-5520.

Sutcliffe, J.G. et al., "TOGA: An automated parsing technology for analyzing expression of nearly all genes," PNAS, 2000, 97(5), 1976-1981.

Svinarchuk, F.P. et al., "Inhibition of HIV proliferation in MT-4 cells by antisense oligonucleotide conjugated to lipophilic groups," Biochimie, 1993, 75, 49-54.

Syvanen, et al., "Quantification of polymerase chain reaction products by affinity-based hybrid collection", Nucl. Acids Res., 1988, 16, 11327-11338.

Szyf, et al., "Growth Regulation of Mouse DNA Methyltransferase Gene Expression", J. Biol. Chem., 1991, 266, 10027-10030.

Tabara, H. et al., "RNAi in C. elegans: Soaking in the Genome Sequence," Science, 1998, 282(5388), 430-431.

Tamanini, F. et al., "The fragile X-related proteins FXRIP and FXRZP contain a functional nucleolar-targeting signal equivalent to the HIV-1 regulatory proteins," Hum. Mol. Genet. (2000) 9(10):1487-1493.

Tang, X.-Q. et al., "2'-C-Branched Ribonucleosides: Synthesis of the Phosphoramidite Derivatives of 2'-C-Beta-Methylcytidine and Their Incorporation into Oligonucleotides," J. Org. Chem., 1999, 64(3), 747-754.

Tazawa et al., "A Novel Procedure for the Synthesis of 2'-O-Alkyl Nucleotides" Biochem., 1972, 11(26), 4931.

Thompson," Applications of Antisense and siRNAs During Preclinical Drug Development," DDT (2002) 7(17): 912-917.

Tidd, D.M. et al., "Evaluation of N-ras oncogene anti-sense, sense and nonsense sequence methylphosphonate oligonucleotide analogues," Anti-Cancer Drug Design, 1988, 3(2), 117-127.

Tijsterman, M. et al., "RNA Helicase MUT-14-Dependent Gene Silencing Triggered in C. elegans by Short Antisense RNAs," Science, 295(5555), 694-697.

Timmons, L. et al., "Ingestion of bacterially expressed dsRNAs can produce specific and potent genetic interference in Caenorhabditis elegans," Gene, 2001, 263(1-2), 103-112.

Timmons, L. et al., "Specific interference by ingested dsRNA," Nature, 1998, 395(6705), 854.

To, K.-Y. "Identification of differential gene expression by high throughput analysis," Comb. Chem. & High Throughput Screen, 2000, 3, 235-241.

Tosquellas, G. et al., "The pro-oligonucleotide approach: solid phase synthesis and preliminary evaluation of model pro-dodecathymidylates," Nucleic Acids Research, 1998, 26(9), 2069-2074.

Tracewell et al., In Vivo Modulation of Rat Cytochrome P450 1A1 by Double-Stranded Phosphorothioate Oligodeoxynucleotides, Toxicology and Applied Pharmacology, 1995, 135, 179-184.

Tseng et al., "Antisense Oligonucleotide Technology in the Development of Cancer Therapeutics", Cancer Gene Therapy, 1994, 1, 65-71.

Tuschl et al., "Targeted mRNA degradation by double-stranded RNA in vitro," Genes Dev, 1999, 13(24), 3191-3197.

Tuschl, T. et al., "Small interfering RNAs: a revolutionary tool for the analysis of gene function and gene therapy," Molecular Interventions, 2002, 2(3), 158-167.

U.S. Appl. No. 09/315,298, filed May 20, 1999, by Teng et al.

U.S. Appl No. 60/423,760, filed Nov. 5, 2002, by Baker et al.

Uhlmann et al., "Antisense Oligonucleotides: A New Therapeutic Principle", Chem. Rev., 1990, 90, 543.

Van der Krol, et al., "Modulation of Eukaryotic Gene Expression by Complementary RNA or DNA Sequences", BioTechniques, 1988, 6, 958-976.

Van Ness et al., "A versatile solid support system for oligodeoxynucleotide probe-based hybridization assays", Nucleic Acids Research, 1991, 19, 3345-3350.

Veronese et al., "Bioconjugation in pharmaceutical chemistry," II Farmaco, 1999, 54, 497-516.

Volk et al., "An antisense transcript from the *Xenopus laevis* bFGF gene coding for an evolutionariy conserved 24 kd protein", EMBO J., 1989, 8, 2983-2988.

Wada, A. et al., "Nuclear export of actin: a novel mechanism regulating the subcellular localization of a major cytoskeletal protein," EMBO J. (1998) 17:1635-1641.

Wahlestedt, C., et al., "Potent and nontoxic antisense oligonucleotides containing locked nucleic acids," Proc. Natl. Acad. Sci. U.S.A., 2000, 97(10), 5633-5638.

Walder, et al., "Antisense DNA and RNA: Progress and Prospects", Genes & Development, 1988, 2, 502-504.

Walder, et al., "Role of RNase H in Hybrid-Arrested Translation by Antisense Oligonucleotides", Proc. Natl. Acad. Sci. USA 1988, 85, 5011-5015.

Wang, J., et al., "Cyclohexene nucleic acids (CeNA): Serum stable oligonucleotides that activate RNase H and increase duplex stability with complementary RNA," J. Am. Chem. Soc., 2000, 122, 8595-8602.

Wang, J., et al., "Syhthesis and binding property of an oligonucleotide containing tetrafluorophenoxazine," Tetrahedron Lett., 1998, 39, 8385-8388.

Wang, X. et al., "Modular Recognition of RNA by a Human Pumilio-Homology Domain," Cell (2002) 110:501-512.

Wei, Z. et al., "Hybridization properties of oligodeoxynucleotide pairs bridged by polyarginine peptides," Nucleic Acids Res. (1996) 24(4):655-661.

Wein, G. et al., "The 3'-UTR of the mRNA coding for the major protein kinase C substrate MARCKS contains a novel CU-rich element interacting with MRNA stabilizing factors HuD and HuR," Eur. 1. Biochem. (2003) 270:350-365.

Wengel, J., et al., "LNA (locked nucleic acid)," Nucleosides, Nucleotides, 1999, 18(6 & 7), 1365-1370.

Westermann et al., "Inhibition of expression of SV40 virus large T-antigen by antisense oligodeoxyribonucleotides", Biomed. B. Acta., 1989, 48, 85-93.

Wetlaufer et al., "Surfactant-Mediated Protein Hydrophobic-Interaction Chromatography", J. Chromatography, 1986, 359, 55-60.

Wianny et al., "Specific interference with gene function by double-stranded RNA in early mouse development," Nature Cell Biology (2000) 2: 70-75.

Wilds et al., "2'-Deoxy-2'-fluoro-B-D-arabinonucleosides and oligonucleotides (2'F-ANA): synthesis and phisicochemical studies," Nucleic Acids Res., 2000, 28, 3625-3635.

Wilds, C.J., et al., "Duplex recognition by oligonucleotides containing 2'-deoxy-2'-fluoro-D-arabinose and 2'-deoxy-2'-fluoro-D-ribose. Intermolecular 2'-OH-phosphate contacts versus sugar puckering in the stabilization of triple-helical complexes," Bioconjugate Chem., 1999, 10, 299-305.

Williams, D.M., et al., Properties of 2'-Fluorothymidine-Containing Oligonucleotides: Interaction with Restriction Endonuclease EcoRV, Biochemistry, 1991, 30, 4001-4009.

Wincott et al., "Synthesis, deprotection, analysis and purification of RNA and ribozymes," Nucl. Acids Res., 1995, 23(14), 2677-2684.

Wolfe, S., et al., "The guache effect. Some stereochemical consequences of adjacent electron pairs and polar bonds," Acc. Of Chem. Res., 1972, 5, 102-111.

Wouters, J. et al., "5-Substituted Pyrimidine 1,5-Anhydronhexitols: Conformational Analysis and Interaction with Viral Thymidine Kinase," Bioorg. Med. Chem. Lett., 1999, 9, 1563-1566.

Wright, P. et al., "Large Scale Synthesis of Oligonucleotides via Phosphoramidite Nucleosides and a High-loaded Polystyrene Support," Tetrahedron Lett., 1993, 34(21), 3373-3376.

Wu et al., "High Resolution Separation and Analysis of Biological Macromolecules", Methods in Enzymology, 1996, 270, 27-47.

Wu et al., "Purification and Properties of *Drosophila* Heat Shock Activator Protein", Science, 1987, 238, 1247-1253.

Wu, H. et al., "Identification and partial purification of human double strand RNase activity. A novel terminating mechanism for oligoribonucleotide antisense drugs," J. Biol. Chem, 1998, 273(5), 2532-2542.

Wu, H. et al., "Properties of Cloned and Expressed Human RNase H1," Journal of Biological Chemistry 1999, vol. 274, pp. 28270-28278.

Wu, X., et al., "Base-pairing systems related to TNA: α-threofuranosyl oligonucleotides containing phosphoramidate linkages," Organic Lett., 2002, 4(8), 1279-1282.

Yang, Y. et al., "HIV-1 TAT-mediated protein transduction and subcellular localization using novel expression vectors," FEBS Letters (2002) 532, 36-44.

Yashima et al., "High-performance affinity chromatography of oligonucleotides on nucleic acid analogue immobilized silica gel columns", J. Chromatog., 1992, 603, 111-119.

Yasuda et al., "Purification and characterization of a ribonuclease from human spleen", Eur. J. Biochem., 1990, 191, 523-529.

Yeung et al., "Photoreactives and Thermal Properties of Psoralen Cross-Links", Biochemistry 1988, 27, 3204-3210.

Yu, Bioorganic and Medicinal Chemistry, 1996, 4, 1685-1692.

Yu, D. et al., "Hybrid oligonucleotides: synthesis, biophysical properties, stability studies, and biological activity," Bioorganic and Medicinal Chemistry, 1996, 4(10), 1685-1692.

Yu, J.-Y., et al., "RNA interference by expression of short-interfering RNAs and hairpin RNAs in mammalian cells," PNAS, 2002, 99(9), 6047-6052.

Yu, Y.T. et al., "A new method for detecting sites of 2'-O-methylation in RNA molecules," RNA, 1997, 3(3), 324-331.

Zanta, M. A. et al., "Gene delivery: A single nuclear localization signal peptide is sufficient to carry DNA to the cell nucleus," Proc. Natl. Acad. Sci. USA (1999) 96:91-96.

Zarytova, et al., "Affinity Chromatography of DNA Fragments and P-Modified Oligonucleotides", Analyt. Biochem., 1990, 188, 214-218.

Zhang et al., "Single Processing Center Models for Human Dicer and Bacterial RNase III," Cell, 2004, 118, 57-68.

Zhang et al., "Targeted Gene Silencing by Small Interfering RNA-Based Knock-Down Technology," Current Pharmaceutical Biotechnology, 2004, 5, 1-7.

Zhang, J., et al., "PowerBLAST: A new network BLAST application for interactive or automated sequence analysis and annotation," Genome Res., 1997, 7, 649-656.

Zhang, Z. et al., "Uptake of N-(4'-pyridoxyl)amines and release of amines by renal cells: A model for transporter-enhanced delivery of bioactive compounds," Proc. Natl. Acad. Sci. USA (1991) 88:10407-10410.

Zhao, Q. et al., "Effect of Different Chemically Modified Oligodeoxynucleotides on Immune Stimulation," Biochemical Pharmacology, 1996, 51, 173-182.

Zhu, T. et al., "Oligonucleotide-Poly-L-ornithine Conjugates: Binding to Complementary DNA and RNA." Antisense Res. Dm. 119931 3:265-275.

Zmudzka, B. et al., "Poly 2'-0-methylcytidylic acid and the role of the 2'-hydroxyl in polynucleotide structure," Biochem Biophys Res Commun, 1969, 37(6), 895-901.

Zon, "Oligonucleotide Analogues as Potential Chemotherapy Agents", Pharm. Res., 1988, 5(9), 539-549.

Zon, "Synthesis of Backbone-Modified DNA Analogues for Biological Applications", J. Protein Chemistry, 1987, 6, 131-145.

Zuckermann, et al., "Efficient methods for attachment of thiol specific probes to the 3'-ends of synthetic oligodeoxyribonucleotides," Nucleic Acids Research, 1987, 15, 5305-5321.

Zuckermann, R. N. et al., "Site-Selective Cleavage of RNA by a Hybrid Enzyme," J. Am. Chem. SOC. (1988) 110:1614-1615.

* cited by examiner

CONJUGATES FOR USE IN HEPATOCYTE FREE UPTAKE ASSAYS

CROSS-REFERENCE TO RELATED APPLICATIONS

This application claims priority to U.S. provisional application Ser. No. 60/608,482 filed Sep. 8, 2004, which is incorporated herein by reference in its entirety.

FIELD OF THE INVENTION

The present invention is directed, in part, to methods of identifying oligomeric compounds, such as double-stranded RNA molecules, having bioactivity in vivo and to kits therefore.

BACKGROUND OF THE INVENTION

The concept of using antisense oligonucleotides (ASOs) to reduce protein expression was first proposed by Zamecnik and Stephenson in 1978 when they demonstrated that an oligonucleotide complementary to 13 nucleotides of the Rous sarcoma virus 35S RNA inhibited virus production in Rous infected chick embryo fibroblasts (Zamecnik et al., Proc. Natl. Acad. Sci., 1978, 75, 280-284). Advances in antisense therapeutics since this time have been substantial, with the first therapeutic ASO being approved for human use in 1998 (Marwick, J. Am. Med. Assoc., 1998, 280, 871). The recent introduction of RNA interference as a method to analyze gene function in invertibrates and plants (Fraser et al., Nature, 2000, 408, 325-330) has suggested that double-stranded RNA, specifically small nucleotide interfering RNAs (siRNAs), may also have therapeutic applications (Vickers et al., J. Biol. Chem., 2003, 278, 7108-7118).

When double-stranded RNA molecules are introduced into cells they are metabolized to small 21-23 nucleotide siRNAs with two-nucleotide (2-nt) 3'-overhangs via the endogenous ribonuclease Dicer (Grishok et al., Science, 2000, 287, 2494-2497; and Zamore et al., Cell, 2000, 101, 25-33). Inside cells, siRNA molecules bind to an RNA-induced silencing protein complex. This complex, which possesses helicase activity, unwinds the double-stranded siRNA, thereby allowing the antisense strand to bind to the targeted RNA. An endonuclease then hydrolyzes the target RNA (Zamore et al., Cell, 2000, 101, 25-33; and Zamore, Science, 2002, 296, 1265-1269). Since ultimately a single stranded RNA molecule binds to the target RNA molecule according to Watson-Crick base pairing rules, siRNA driven RNA interference is essentially an antisense mechanism of action (Vickers et al., J. Biol. Chem., 2003, 278, 7108-7118). siRNA duplexes used for silencing mammalian genes in cultured cells are usually chemically synthesized 21-23 nucleotide (21-23-nt) siRNAs, where the siRNA's sense and antisense strands are paired, containing 2-nt 3'-overhangs (Harborth et al., J. Cell. Sci., 2001, 114, 4557-4565). siRNA molecules were designed with a 2 nucleotide (2 nt) 3'-overhang because this form of siRNA has been shown to be most effective in vitro (Elbashir et al., Nature, 2001, 411, 494-498). The 5'-hydroxyl is not blocked by methylation or a 5'-phosphodiester linkage, as both prevent the 5'-phosphorylation of the antisense siRNA, a step necessary for target RNA degradation inside cells (Nykanen et al., Cell, 2001, 107, 309-321; and Schwartz et al., Mol. Cell., 2002, 10, 537-548).

Zamore and others have reported that single-stranded antisense oligonucleotides are less potent and less effective than siRNAs at reducing gene transcript levels (Zamore et al., 2000, Cell, 101, 25-33; and Caplen et al., Proc. Natl. Acad. Sci. USA, 2001, 98, 9742-9747). As the antisense molecules used in those studies were single-stranded unmodified RNA, which are rapidly degraded by endogenous nucleases, here we compare antisense siRNA molecules to "second generation" phosphorothioate (PS) oligodeoxynucleotides modified to contain 2'-O-methoxyethyls (MOEs), both in vitro and in vivo. These second generation antisense oligonucleotides are chimeric molecules, which by design, contain a stretch of RNAse H sensitive 2'deoxy residues in the middle, flanked on both sides with a region of 2'MOE modifications. These molecules, termed MOE gapmers, take advantage of: 1) 2'-MOE modifications, which form higher affinity complexes and possess higher nuclease resistance relative to "first generation" PS oligonucleotides, resulting in increased ASO potency both in vitro and in vivo (Altmann et al., Biochem. Soc. Trans., 1996, 24, 630-637; Dean, N. M., Pharmacology of 2'-O-(2-methoxy)-ethyl modified antisense oligonucleotides, in Antisense Technology: Principles, Strategies and Applications, S. Crooke, Editor, Marcel Dekker, 2001; and Kurreck, Eur. J. Biochem., 2003, 270, 1628-1644); and 2) PS 2'deoxyoligonucleotides, which when duplexed with RNA, serve as efficient substrates for the robust endogenous RNAse H antisense-mediated cleavage of RNA (Baker et al., Biochim. Biophys. Acta, 1999, 1489, 3-18). Indeed, antisense MOE gapmer reduction of target mRNA levels can be in the order of 85-90% of control levels (Crooke et al., Annu. Rev. Pharmacol. Toxicol., 1996, 36, 107-129; and Baker et al., Biochim. Biophys. Acta, 1999, 1489, 3-18).

Antisense oligonucleotides are known to preferentially accumulate in hepatic tissue in vivo (Cossum et al., J. Pharmacol. Exp. Ther., 1993, 267, 1181-1190; and Graham et al., J. Pharmacol. Exp. Therap., 1998, 286, 447-458). Nestle and colleagues have previously reported that cultured hepatocytes rapidly internalize antisense compounds in the absence of cationic lipid transfection reagents (Nestle et al., J. Invest. Dermatol., 1994, 103, 569-575). These observations are likely related to the remarkable transport rates displayed by hepatocytes, where fluid-phase endocytosis at the basolateral membrane is estimated to be 8% of the total membrane surface area per minute per cell (Crawford, Semin. Liver Dis., 1996, 16, 169-189).

The present invention provides a primary hepatocyte cell model that demonstrates in vitro antisense oligonucleotide uptake and intracellular trafficking similar to postulated in vivo antisense oligonucleotide uptake and trafficking. In particular, the present invention demonstrates antisense oligonucleotide mediated target mRNA reduction in primary hepatocytes without cationic lipid carriers, analogous to that postulated to occur in vivo. The results described herein suggest that the mechanism of cellular uptake of single strand MOE gapmers and double strand siRNA are different. Single strand MOE gapmers, but likely not double strand siRNA, are taken up in hepatocytes in vivo and in vitro without aid of cationic lipids. When siRNA molecules are transfected into cells, they produce a dose dependent reduction of target gene expression.

SUMMARY OF THE INVENTION

The present invention provides methods of identifying oligomeric compounds having bioactivity in vivo. A bioindicative cell is contacted with one or more pairs of candidate oligomeric compounds in vitro. The bioindicative cell is contacted with a first oligomeric compound having a sense strand orientation. The bioindicative cell is contacted with a second oligomeric compound having an antisense strand orientation.

The bioindicative cell is contacted with the second oligomeric compound at least one hour after the bioindicative cell is contacted with the first oligomeric compound. At least a portion of the second oligomeric compound is capable of hybridizing with at least a portion of the first oligomeric compound. It is determined whether the bioindicative cell has an altered phenotype. If the bioindicative cell has an altered phenotype, one or more of the pairs of candidate oligomeric compounds comprises in vivo bioactivity.

In some embodiments, the first and second oligomeric compounds are small interfering RNA. In some embodiments, the contacting occurs in the absence of a transfection reagent. In some embodiments, the bioindicative cell is a mammalian tissue-derived cell, such as a primary hepatocyte, primary keratinocyte, primary macrophage, primary fibroblast, primary pancreatic cell, or a stem cell. In some embodiments, the mammalian tissue-derived cell is a rodent or primary primate hepatocyte such as a Cynomolgus monkey or human.

In some embodiments, the altered phenotype is an increase in uptake of the candidate oligomeric compounds, decrease in expression of the mRNA produced from the gene to which the candidate oligomeric compounds are targeted, or decrease in expression of the protein encoded by the gene or mRNA to which the candidate oligomeric compounds are targeted.

In some embodiments, the bioindicative cell is contacted with the second oligomeric compound at least two hours after the bioindicative cell is contacted with the first oligomeric compound. In some embodiments, the bioindicative cell is contacted with the second oligomeric compound between two hours and four hours after the bioindicative cell is contacted with the first oligomeric compound. In some embodiments, each of the first and second oligomeric compounds comprises 10 to 40 nucleotides, 18 to 30 nucleotides, or 21 to 24 nucleotides.

In some embodiments, at least a portion of the second oligomeric compound is complementary to and capable of hybridizing to a selected target nucleic acid, the second oligomeric compound comprises a plurality of linked nucleosides linked by internucleoside linking groups, the first oligomeric compound comprises a plurality of linked nucleosides linked by internucleoside linking groups and wherein essentially each of the nucleosides is other than 2'-OH and have 3'-endo conformational geometry, and the first and second oligomeric compounds optionally comprise a phosphate group, a 3'-overhang, or a conjugate group.

The present invention also provides kits comprising an assay platform, a bioindicative cell, and one or more bioactive pairs of oligomeric compounds which comprise a first oligomeric compound having a sense strand orientation and a second oligomeric compound having an antisense strand orientation, wherein at least a portion of the second oligomeric compound is capable of hybridizing with at least a portion of the first oligomeric compound.

DESCRIPTION OF EMBODIMENTS

Figure 1:
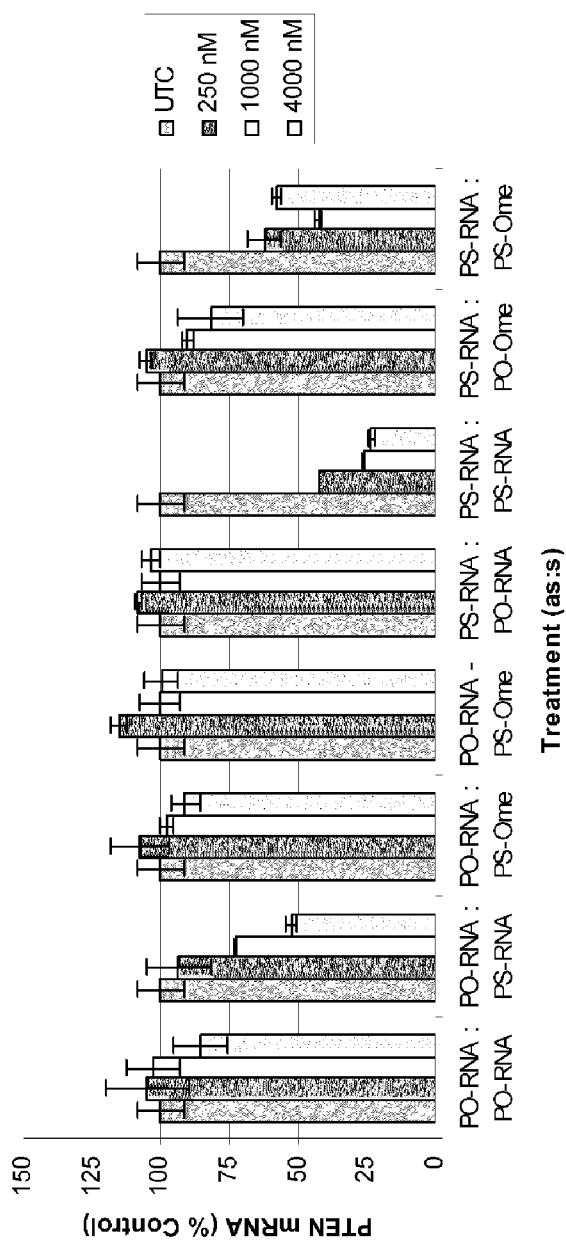
FIG. 1 shows the results of a dose-response for PTEN siRNA oligomeric compounds in primary hepatocytes.

The present invention provides methods of identifying oligomeric compounds having bioactivity in vivo, and kits. In particular, the present invention provides methods of identifying oligomeric compounds, such as double-stranded RNA, having bioactivity in vivo. A bioindicative cell is contacted with one or more pairs of candidate oligomeric compounds in vitro. Contacting can occur by any means known to those skilled in the art. The bioindicative cell is examined to determine whether it has an altered phenotype. Such examination can be carried out via morphological analysis, biochemical analysis, or the like. If the bioindicative cell has an altered phenotype, one or more of the pairs of candidate oligomeric compounds comprises in vivo bioactivity.

In some embodiments, the oligomeric compound can be double stranded. In some embodiments, the oligomeric compound is a small interfering RNA. In some embodiments, the bioindicative cell is a mammalian tissue-derived cell including, but not limited to, a primary hepatocyte, primary keratinocyte, primary macrophage, primary fibroblast, primary pancreatic cell, or a stem cell. In some embodiments, the mammalian tissue-derived cell is a rodent (i.e., mouse or rat) primary hepatocyte. In other embodiments, the mammalian tissue-derived cell is a primate primary hepatocyte. Primates include, but are not limited to, monkeys (i.e., Cynomolgus) and humans.

Altered phenotypes include, but are not limited to, an increase in uptake of the candidate oligomeric compound, decrease in expression of the mRNA produced from the gene to which the candidate oligomeric compound is targeted, or decrease in expression of the protein encoded by the gene or mRNA to which the candidate oligomeric compound is targeted.

As used herein, "bioactivity in vivo" is any activity within a cell in vivo including, but not limited to, alteration of the level of an RNA molecule to which the oligomeric compound(s) is targeted, or alteration of a protein encoded by an RNA molecule to which the oligomeric compound(s) is targeted.

As used herein, "a bioindicative cell" is any cell in which an in vitro activity of an oligomeric compound(s) is observed and is correlated to an in vivo activity of the same oligomeric compound(s). Bioindicative cells include, but are not limited to, mammalian tissue-derived cells such as, for example, primary hepatocytes, primary keratinocytes, primary macrophages, primary fibroblasts, primary pancreatic cells, or stem cells.

As used herein, "altered phenotype" is any phenotypic trait for which an alteration can be observed. Altered phenotypes include, but are not limited to, an increase in uptake of the candidate oligomeric compound(s), decrease in expression of the RNA produced from the gene to which the candidate oligomeric compound(s) is targeted, or decrease in expression of the protein encoded by the gene to which the candidate oligomeric compound(s) is targeted.

As used herein, "transfection reagent" is any reagent that enhances transfection of an oligomeric compound(s) into a cell. Transfection reagents are well known to the skilled artisan.

As used herein, "assay platform" is any platform in which a cell-based assay can be carried out including, but not limited to, a 96-well microtiter plate, a 48-well microtiter plate, a 6-well microtiter plate, and the like.

In particular, the present invention provides methods of sequentially delivering a first oligomeric compound, such as an siRNA, comprising a sense strand orientation followed by delivery of a second oligomeric compound, such as another siRNA, comprising an antisense orientation. In some embodiments, the second oligomeric compound is delivered to the bioindicative cell at least one hour, at least two hours, or between two and four hours after delivery of the first oligomeric compound.

In some embodiments, at least the nucleic acid target region of the second oligomeric compound has 3'-endo sugar conformational geometry and comprises uniform ribofuranose nucleosides. Another suitable modification of the second oligomeric compound is a 5'-phosphate group. In some embodiments, at least one of the monomeric subunits of the hybridizing region of the first oligomeric compound are modified to give each monomeric subunit 3'-endo sugar conformational geometry. Another modification of the first oligomeric compound is a 5'-phosphate group. In some embodiments, the compositions have a double stranded region that at least in part hybridizes to and is complementary to a nucleic acid target.

In one aspect of the present invention, the second oligomeric compound is a full phosphodiester or phosphorothioate RNA that can include a 5'-phosphate group and the first oligomeric compound is a fully modified phosphodiester or phosphorothioate such that each monomeric subunit has 3'-endo sugar conformational geometry. Suitable 3'-endo modifications include, without limitation, —F, —O—CH$_2$CH$_2$—O—CH$_3$, —O—CH$_3$, —O—CH$_2$—CH=CH$_2$ or —O—CH$_2$—CH—CH$_2$—NH(R$_j$) where R$_j$ is H or C$_1$-C$_{10}$ alkyl with 2'-O-methy as a more suitable group. The presence of modifications in both the sense and the antisense strand of compositions of the present invention greatly enhance the stability of the corresponding compositions.

In the context of this invention, the term "oligomeric compound" refers to a plurality of naturally-occurring and/or non-naturally-occurring monomeric units joined together in a specific sequence. This term includes oligonucleotides, oligonucleosides, oligonucleotide analogs, oligonucleotide mimetics, and combinations of these. Oligomeric compounds are typically structurally distinguishable from, yet functionally inter-change-able with, naturally-occurring or synthetic wild-type oligonucleotides. Thus, oligomeric compounds include all such structures that function effectively to mimic the structure and/or function of a desired RNA or DNA strand, for example, by hybridizing to a target.

Oligomeric compounds are routinely prepared linearly but can be joined or otherwise prepared to be circular and may also include branching. Oligomeric compounds can included double stranded constructs such as for example two strands hybridized to form double stranded compounds. The double stranded compounds can be linked or separate and can include overhangs on the ends. In general an oligomeric compound comprises a backbone of linked monomeric subunits where each linked monomeric subunit is directly or indirectly attached to a heterocyclic base moiety. Oligomeric compounds may also include monomeric subunits that are not linked to a heterocyclic base moiety thereby providing abasic sites. The linkages joining the monomeric subunits, the sugar moieties or surrogates and the heterocyclic base moieties can be independently modified giving rise to a plurality of motifs for the resulting oligomeric compounds including hemimers, gapmers and chimeras.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions that function similarly. Such modified or substituted oligonucleotides are often suitable over native forms because of desirable properties such as, for example, enhanced cellular uptake, enhanced affinity for nucleic acid target, and increased stability in the presence of nucleases.

Included in suitable oligomeric compounds are oligonucleotides such as antisense oligonucleotides, ribozymes, external guide sequence (EGS) oligonucleotides, alternate splicers, primers, probes, and other oligonucleotides that hybridize to at least a portion of the target nucleic acid. As such, these oligonucleotides may be introduced in the form of single-stranded, double-stranded, circular or hairpin oligonucleotides and may contain structural elements such as internal or terminal bulges or loops. Once introduced to a system, the compositions of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. Single-stranded antisense oligonucleotides that are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While a suitable form of antisense oligonucleotide is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

In the context of this invention, the term "oligonucleoside" refers to a sequence of nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include but are not limited to siloxane, sulfide, sulfoxide, sulfone, acetyl, formacetyl, thioformacetyl, methylene formacetyl, thioformacetyl, alkeneyl, sulfamate; methyleneimino, methylenehydrazino, sulfonate, sulfonamide, amide and others having mixed N, O, S, and CH$_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240;

5,608,046; 5,610,289; 5,618,704; 5,623,070; 5,663,312; 5,633,360; 5,677,437; 5,792,608; 5,646,269 and 5,677,439.

In addition to the modifications described above, the nucleosides of the compositions of the invention can have a variety of other modifications so long as these other modifications either alone or in combination with other nucleosides enhance one or more of the desired properties described above. Thus, for nucleotides that are incorporated into compositions of the invention, these nucleotides can have sugar portions that correspond to naturally-occurring sugars or modified sugars. Representative modified sugars include carbocyclic or acyclic sugars, sugars having substituent groups at one or more of their 2', 3' or 4' positions and sugars having substituents in place of one or more hydrogen atoms of the sugar. Additional nucleosides amenable to the present invention having altered base moieties and or altered sugar moieties are disclosed in U.S. Pat. No. 3,687,808 and PCT application PCT/US89/02323.

Oligomeric compounds having altered base moieties or altered sugar moieties are also included in the present invention. All such modified oligomeric compounds are comprehended by this invention so long as they function effectively to mimic the structure of a desired RNA or DNA strand. A class of representative base modifications include tricyclic cytosine analog, termed "G clamp" (Lin et al., J. Am. Chem. Soc., 1998, 120, 8531). This analog makes four hydrogen bonds to a complementary guanine (G) within a helix by simultaneously recognizing the Watson-Crick and Hoogsteen faces of the targeted G. This G clamp modification when incorporated into phosphorothioate oligonucleotides, dramatically enhances antisense potencies in cell culture. The compositions of the invention also can include phenoxazine-substituted bases of the type disclosed by Flanagan et al., Nat. Biotechnol., 1999, 17, 48-52.

The oligomeric compounds in accordance with this invention can comprise from about 8 to about 80 monomeric subunits (i.e. from about 8 to about 80 linked nucleosides). One of ordinary skill in the art will appreciate that the invention embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 monomeric subunits in length, or any range therewithin.

In some embodiments, the oligomeric compounds of the invention are 12 to 50 monomeric subunits in length. One having ordinary skill in the art will appreciate that this embodies oligomeric compounds of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 monomeric subunits in length, or any range therewithin.

In other embodiments, the oligomeric compounds of the invention are 15 to 30 monomeric subunits in length. One having ordinary skill in the art will appreciate that this embodies oligomeric compounds of 15, 16, 17, 18, 19, 20, 21, 22, 23, 24, 25, 26, 27, 28, 29, or 30 monomeric subunits in length, or any range therewithin.

Oligomeric compounds used in the compositions of the present invention can also be modified to have one or more stabilizing groups that are generally attached to one or both termini of oligomeric compounds to enhance properties such as for example nuclease stability. Included in stabilizing groups are cap structures. By "cap structure" or "terminal cap moiety" is meant chemical modifications, which have been incorporated at either terminus of oligonucleotides (see for example Wincott et al., WO 97/26270). These terminal modifications protect the oligomeric compounds having terminal nucleic acid molecules from exonuclease degradation, and can help in delivery and/or localization within a cell. The cap can be present at the 5'-terminus (5'-cap) or at the 3'-terminus (3'-cap) or can be present on both termini. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl riucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT publication No. WO 97/26270).

Particularly suitable 3'-cap structures of the present invention include, for example, 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Tyer, 1993, Tetrahedron 49, 1925).

A further embodiment of the present invention is "structured" antisense constructs, e.g. siRNA, which contain suitable and/or enabling attributes and compositions for regulation of gene expression in vivo through usage of conventional administration procedures. One primary feature of the structured constructs is that they exist in both a structured and unstructured form under physiological conditions, e.g. unhybridized single-strand and hybridized double-strand forms. The antisense construct may be modified to impart resistance to degradation by nucleases in either or both forms.

Modifications to the base, sugar, and phosphate linkage may also be used to affect changes in the equilibrium between the structured and unstructured form, in particular for sequences or compositions that yield duplex stabilities below or above the optimal range for in vivo delivery applications, e.g. Tm=37±8° C. These modifications may include bases that form mismatches, with preference for mismatched bases in the sense portion of the antisense construct. See FIG. 1.

It is not necessary for all positions in an oligomeric compound to be uniformly modified, and in fact more than one of the aforementioned modifications may be incorporated in a single oligomeric compound or even at a single monomeric subunit such as a nucleoside within an oligonucleotide. The present invention also includes chimeric oligomeric compounds such as chimeric oligonucleotides. "Chimeric" oligomeric compounds or "chimeras," in the context of this invention, are oligomeric compounds such as oligonucleotides containing two or more chemically distinct regions, each made up of at least one monomer unit, i.e., a nucleotide in the case of a nucleic acid based oligomer.

Chimeric oligomeric compounds typically contain at least one region modified so as to confer increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of inhibition of gene expression. Consequently, comparable results can often be obtained with shorter oligonucleotides when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art.

Chimeric compositions of the invention may be formed as composite structures of two or more oligomeric compounds such as oligonucleotides, oligonucleotide analogs, oligonucleosides and/or oligonucleotide mimetics as described above. Such oligomeric compounds have also been referred to in the art as hybrids hemimers, gapmers or inverted gapmers. Representative U.S. patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922.

Specific examples of suitable oligomeric compounds useful in this invention include oligonucleotides containing modified e.g. non-naturally occurring internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

In the *C. elegans* system, modification of the internucleotide linkage (phosphorothioate) did not significantly interfere with RNAi activity. Based on this observation, it is suggested that certain compositions of the invention can also have one or more modified internucleoside linkages. A suitable phosphorus containing modified internucleoside linkage is the phosphorothioate internucleoside linkage.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and borano-phosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage, i.e. a single inverted nucleoside residue that may be abasic (the nucleobase is missing or has a hydroxyl group in place thereof). Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050.

In some embodiments, oligonucleotides have one or more phosphorothioate and/or heteroatom internucleoside linkages, in particular —$CH_2$—NH—O—$CH_2$—, —$CH_2$—N($CH_3$)—O—$CH_2$—(known as a methylene (methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester internucleotide linkage is represented as —O—P(=O)(OH)—O—$CH_2$—). The MMI type internucleoside linkages are disclosed in the above referenced U.S. Pat. No. 5,489,677. Suitable amide internucleoside linkages are disclosed in the above referenced U.S. Pat. No. 5,602,240.

Suitable modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439.

In addition to having a 2'-O-methyl modified nucleiside the compositions of the present invention may also contain additional modified sugar moieties. Suitable modified sugar moieties comprise a sugar substituent group selected from, but not limited to: OH; F; O—, S—, or N-alkyl; O—, S—, or N-alkenyl; O—, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are $O((CH_2)_nO)_m$—$CH_3$, $O(CH_2)_n$$OCH_3$, $O(CH_2)_n NH_2$, $O(CH_2)_n CH_3$, $O(CH_2)_n ONH_2$, and $O(CH_2)_n ON$—$((CH_2)_n CH_3)_2$, where n and m are from 1 to about 10, or any subset thereof. Other suitable sugar substituent groups include, but are not limited to: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocyclo-alkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties, or any subset thereof. A suitable modification includes 2'-methoxyethoxy (2'—O—$CH_2CH_2OCH_3$, also known as 2'-O-(2-methoxyethyl) or 2'-MOE) (Martin et al., Helv. Chim. Acta, 1995, 78, 486-504) i.e., an alkoxyalkoxy group. A further modification includes 2'-dimethylamino-oxyethoxy, i.e., a O(CH$_2$)$_2$ON(CH$_3$)$_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'—O—CH$_2$—O—CH$_2$—N(CH$_3$)$_2$.

Other suitable sugar substituent groups include, but are not limited to, methoxy (—O—CH$_3$), aminopropoxy (—OCH$_2$CH$_2$CH$_2$NH$_2$), allyl (—CH$_2$—CH=CH$_2$), —O-allyl (—O—CH$_2$—CH=CH$_2$) and fluoro (F). 2'-Sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligonucleotides may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920.

Particularly suitable sugar substituent groups include O((CH$_2$)$_n$O)$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON((CH$_2$)$_n$CH$_3$))$_2$, where n and m are from 1 to about 10.

Further representative sugar substituent groups include groups of formula I$_a$ or II$_a$:

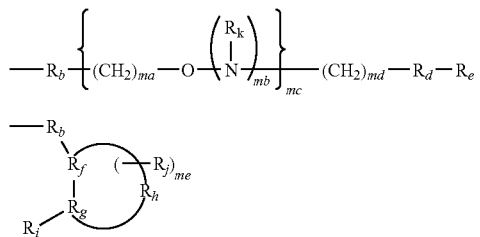

wherein:
R$_b$ is O, S or NH;
R$_d$ is a single bond, O, S or C(=O);
R$_e$ is C$_1$-C$_{10}$ alkyl, N(R$_k$)(R$_m$), N(R$_k$)(R$_n$), N=C(R$_p$)(R$_q$), N=C(R$_p$)(R$_r$) or has formula III$_a$;

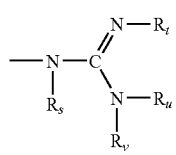

R$_p$ and R$_q$ are each independently hydrogen or C$_1$-C$_{10}$ alkyl;
R$_r$ is —R$_x$—R$_y$;
each R$_s$, R$_t$, R$_u$ and R$_v$ is, independently, hydrogen, C(O)R$_w$, substituted or unsubstituted C$_1$-C$_{10}$ alkyl, substituted or unsubstituted C$_2$-C$_{10}$ alkenyl, substituted or unsubstituted C$_2$-C$_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, R$_u$ and R$_v$, together form a phthalimido moiety with the nitrogen atom to which they are attached;

each R$_w$ is, independently, substituted or unsubstituted C$_1$-C$_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl;

R$_k$ is hydrogen, a nitrogen protecting group or —R$_x$—R$_y$;
R$_p$ is hydrogen, a nitrogen protecting group or —R$_x$—R$_y$;
R$_x$ is a bond or a linking moiety;
R$_y$ is a chemical functional group, a conjugate group or a solid support medium;

each R$_m$ and R$_n$ is, independently, H, a nitrogen protecting group, substituted or unsubstituted C$_1$-C$_{10}$ alkyl, substituted or unsubstituted C$_2$-C$_{10}$ alkenyl, substituted or unsubstituted C$_2$-C$_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl, alkynyl; NH$_3$$^+$, N(R$_u$)(R$_v$), guanidino and acyl where the acyl is an acid amide or an ester;

or R$_m$ and R$_n$, together, are a nitrogen protecting group, are joined in a ring structure that optionally includes an additional heteroatom selected from N and O or are a chemical functional group;

R$_i$ is OR$_z$, SR$_z$, or N(R$_z$)$_2$;
each R$_z$ is, independently, H, C$_1$-C$_8$ alkyl, C$_1$-C$_8$ haloalkyl, C(=NH)N(H)R$_u$, C(=O)N(H)R$_u$ or OC(=O)N(H)R$_u$;

R$_f$, R$_g$ and R$_h$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;

R$_j$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, N(R$_k$)(R$_m$) OR$_k$, halo, SR$_k$ or CN;

m$_a$ is 1 to about 10;
each mb is, independently, 0 or 1;
mc is 0 or an integer from 1 to 10;
md is an integer from 1 to 10;
me is from 0, 1 or 2; and
provided that when mc is 0, md is greater than 1.

Representative substituents groups of Formula I are disclosed in U.S. patent application Ser. No. 09/130,973, filed Aug. 7, 1998, entitled "Capped 2'-Oxyethoxy Oligonucleotides."

Representative cyclic substituent groups of Formula II are disclosed in U.S. patent application Ser. No. 09/123,108, filed Jul. 27, 1998, entitled "RNA Targeted 2'-Oligomeric compounds that are Conformationally Preorganized."

Representative guanidino substituent groups that are shown in formula III and IV are disclosed in co-owned U.S. patent application Ser. No. 09/349,040, entitled "Functionalized Oligomers", filed Jul. 7, 1999.

Representative acetamido substituent groups are disclosed in U.S. Pat. No. 6,147,200.

Representative dimethylaminoethyloxyethyl substituent groups are disclosed in International Patent Application PCT/US99/17895, entitled "2'-O-Dimethylaminoethyloxy-ethyl-Oligomeric compounds", filed Aug. 6, 1999.

Oligomeric compounds including oligonucleotides may also include nucleobase (often referred to in the art simply as "base" or "heterocyclic base moiety") modifications or substitutions. As used herein, "unmodified" or "natural" nucleobases include the purine bases adenine (A) and guanine (G), and the pyrimidine bases thymine (T), cytosine (C) and uracil (U). Modified nucleobases also referred herein as heterocyclic base moieties include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of the compositions of the invention. These include 5-substituted pyrimidines, 6-azapyrimidines and N-2, N-6 and O-6 substituted purines, including 2 aminopropyladenine, 5-propynyluracil and 5-propynylcytosine. 5 methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278) and are presently suitable base substitutions, even more particularly when combined with 2'-O-methoxyethyl sugar modifications.

Oligomeric compounds of the present invention can also include polycyclic heterocyclic compounds in place of one or more heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Many of these polycyclic heterocyclic compounds have the general formula:

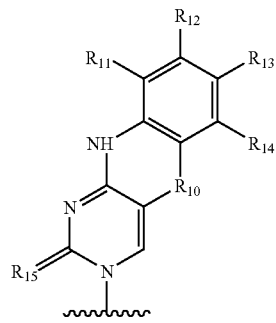

Representative cytosine analogs that make 3 hydrogen bonds with a guanosine in a second strand include 1,3-diazaphenoxazine-2-one ($R_{10}$=O, $R_{11}$-$R_{14}$=H) (Kurchavov et al., Nucleosides and Nucleotides, 1997, 16, 1837-1846), 1,3-diazaphenothiazine-2-one ($R_{10}$=S, $R_{11}$-$R_{14}$=H), (Lin et al., J. Am. Chem. Soc., 1995, 117, 3873-3874) and 6,7,8,9-tetrafluoro-1,3-diazaphenoxazine-2-one ($R_{10}$=O, $R_{11}$-$R_{14}$=F) (Wang et al., Tetrahedron Lett., 1998, 39, 8385-8388). Incorporated into oligonucleotides these base modifications were shown to hybridize with complementary guanine and the latter was also shown to hybridize with adenine and to enhance helical thermal stability by extended stacking interactions (also see U.S. Patent Application entitled "Modified Peptide Nucleic Acids" filed May 24, 2002, Ser. No. 10/155, 920; and U.S. Patent Application entitled "Nuclease Resistant Chimeric Oligonucleotides" filed May 24, 2002, Ser. No. 10/013,295).

Further helix-stabilizing properties have been observed when a cytosine analog/substitute has an aminoethoxy moiety attached to the rigid 1,3-diazaphenoxazine-2-one scaffold ($R_{10}$=O, $R_{11}$=—O—(CH$_2$)$_2$—NH$_2$, $R_{12\text{-}14}$=H) (Lin et al., J. Am. Chem. Soc., 1998, 120, 8531-8532). Binding studies demonstrated that a single incorporation could enhance the binding affinity of a model oligonucleotide to its complementary target DNA or RNA with a $\Delta T_m$ of up to 18° relative to 5-methyl cytosine (dC5$^{me}$), which is the highest known affinity enhancement for a single modification, yet. On the other hand, the gain in helical stability does not compromise the specificity of the oligonucleotides. The $T_m$ data indicate an even greater discrimination between the perfect match and mismatched sequences compared to dC5$^{me}$. It was suggested that the tethered amino group serves as an additional hydrogen bond donor to interact with the Hoogsteen face, namely the O6, of a complementary guanine thereby forming 4 hydrogen bonds. This means that the increased affinity of G-clamp is mediated by the combination of extended base stacking and additional specific hydrogen bonding.

Further tricyclic heterocyclic compounds and methods of using them that are amenable to the present invention are disclosed in U.S. Pat. No. 6,028,183, which issued on May 22, 2000, and U.S. Pat. No. 6,007,992, which issued on Dec. 28, 1999.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNaseH, enhance cellular uptake and exhibit an increased antisense activity (Lin et al., J. Am. Chem. Soc., 1998, 120, 8531-8532). The activity enhancement was even more pronounced in case of G-clamp, as a single substitution was shown to significantly improve the in vitro potency of a 20mer 2'-deoxyphosphorothioate oligonucleotides (Flanagan et al., Proc. Natl. Acad. Sci. USA, 1999, 96, 3513-3518). Nevertheless, to optimize oligonucleotide design and to better understand the impact of these heterocyclic modifications on the biological activity, it is important to evaluate their effect on the nuclease stability of the oligomers.

Further modified polycyclic heterocyclic compounds useful as heterocyclic bases are disclosed in but not limited to, the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121; 5,596,091; 5,614,617; 5,645,985; 5,646,269; 5,750,692; 5,830,653; 5,763,588; 6,005,096; and 5,681,941, and U.S. patent application Ser. No. 09/996,292 filed Nov. 28, 2001.

Oligomeric compounds used in the compositions of the present invention can also be modified to have one or more moieties or conjugates which enhance the activity, cellular distribution or cellular uptake of the resulting oligomeric compounds. In one embodiment such modified oligomeric compounds are prepared by covalently attaching conjugate groups to functional groups such as hydroxyl or amino groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmaco-dynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992.

Conjugate moieties include but are not limited to lipid moieties such as a cholesterol moiety. (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., dihexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylaminocarbonyl-oxycholesterol moiety (Crooke et al., J. Pharmacol. Exp. Ther., 1996, 277, 923-937).

The oligomeric compounds of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999).

Representative U.S. patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

In one aspect of the present invention oligomeric compounds include nucleosides synthetically modified to induce a 3'-endo sugar conformation. A nucleoside can incorporate synthetic modifications of the heterocyclic base moiety, the sugar moiety or both to induce a desired 3'-endo sugar conformation. These modified nucleosides are used to mimic RNA like nucleosides so that particular properties of an oligomeric compound can be enhanced while maintaining the desirable 3'-endo conformational geometry. There is an apparent preference for an RNA type duplex (A form helix, predominantly 3'-endo) as a requirement of RNA interference which is supported in part by the fact that duplexes composed of 2'-deoxy-2'-F-nucleosides appear efficient in triggering RNAi response in the C. elegans system. Properties that are enhanced by using more stable 3'-endo nucleosides include but aren't limited to modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. The present invention provides oligomeric compounds having one or more nucleosides modified in such a way as to favor a C3'-endo type conformation.

Scheme 1

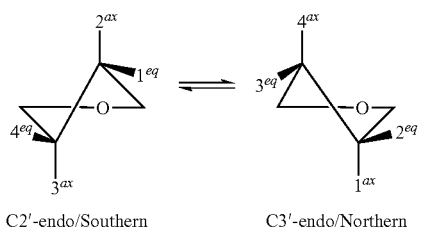

C2'-endo/Southern      C3'-endo/Northern

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer- Verlag.) Modification of the 2' position to favor the 3'-endo conformation can be achieved while maintaining the 2'-OH as a recognition element (Gallo et al., Tetrahedron, 2001, 57, 5707-5713; Harry-O'kuru et al., J. Org. Chem., 1997, 62, 1754-1759; and Tang et al., J. Org. Chem., 1999, 64, 747-754). Alternatively, preference for the 3'-endo conformation can be achieved by deletion of the 2'-OH as exemplified by 2'deoxy-2'F-nucleosides (Kawasaki et al., J. Med. Chem., 1993, 36, 831-841), which adopts the 3'-endo conformation positioning the electronegative fluorine atom in the axial position. Other modifications of the ribose ring, for example substitution at the 4'-position to give 4'-F modified nucleosides (Guillerm et al., Bioorganic and Medicinal Chemistry Letters, 1995, 5, 1455-1460; and Owen et al., J. Org. Chem., 1976, 41, 3010-3017), or for example modification to yield methanocarba nucleoside analogs (Jacobson et al., J. Med. Chem. Lett., 2000, 43, 2196-2203; and Lee et al., Bioorganic and Medicinal Chemistry Letters, 2001, 11, 1333-1337) also induce preference for the 3'-endo conformation. Some modifications actually lock the conformational geometry by formation of a bicyclic sugar moiety e.g. locked nucleic acid (LNA) (Singh et al, Chem. Commun., 1998, 4, 455-456), and ethylene bridged nucleic acids (ENA) (Morita et al, Bioorganic & Medicinal Chemistry Letters, 2002, 12, 73-76).

Examples of modified nucleosides amenable to the present invention are shown below in Table 1. These examples are meant to be representative and not exhaustive.

Suitable conformations of modified nucleosides and their oligomers can be estimated by various methods such as molecular dynamics calculations, nuclear magnetic resonance spectroscopy and CD measurements. Hence, modifications predicted to induce RNA like conformations, A-form duplex geometry in an oligomeric context, are selected for use in one or more of the oligomeric compounds of the present invention. The synthesis of numerous of the modified nucleosides amenable to the present invention are known in the art (see for example, Chemistry of Nucleosides and Nucleotides Vol 1-3, ed. Leroy B. Townsend, 1988, Plenum press., and the examples section below.) Nucleosides known to be inhibitors/substrates for RNA dependent RNA polymerases (for example HCV NS5B).

In one aspect, the present invention is directed to oligomeric compounds that are prepared having enhanced properties compared to native RNA against nucleic acid targets. A target is identified and an oligomeric compound is selected having an effective length and sequence that is complementary to a portion of the target sequence. Each nucleoside of the selected sequence is scrutinized for possible enhancing modifications. A suitable modification would be the replacement of one or more RNA nucleosides with nucleosides that have the same 3'-endo conformational geometry. Such modifications can enhance chemical and nuclease stability relative to native RNA while at the same time being much cheaper and easier to synthesize and/or incorporate into an oligomeric compound. The selected sequence can be further divided into regions and the nucleosides of each region evaluated for enhancing modifications that can be the result of a chimeric configuration. Consideration is also given to the termini (e.g. 5' and 3'-termini) as there are often advantageous modifications that can be made to one or more of the terminal monomeric subunits. In one aspect of the invention, desired properties and or activity of oligomeric compounds are enhanced by the inclusion of a 5'-phosphate or modified phosphate moiety.

The terms used to describe the conformational geometry of homoduplex nucleic acids are "A Form" for RNA and "B Form" for DNA. The respective conformational geometry for RNA and DNA duplexes was determined from X-ray diffraction analysis of nucleic acid fibers (Arnott et al., Biochem. Biophys. Res. Comm., 1970, 47, 1504). In general, RNA:RNA duplexes are more stable and have higher melting temperatures (Tm's) than DNA:DNA duplexes (Sanger et al., Principles of Nucleic Acid Structure, 1984, Springer-Verlag; New York, N.Y.; Lesnik et al., Biochemistry, 1995, 34, 10807-10815; Conte et al., Nucleic Acids Res., 1997, 25, 2627-2634). The increased stability of RNA has been attributed to several structural features, most notably the improved base stacking interactions that result from an A-form geometry (Searle et al., Nucleic Acids Res., 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., Biochemistry, 1996, 35, 8489-8494). On the other hand, deoxy nucleic acids prefer a C2' endo sugar pucker, i.e., also known as Southern pucker, which is thought to impart a less stable B-form geometry (Sanger, W. (1984) Principles of Nucleic Acid Structure, Springer-Verlag, New York, N.Y.). As used herein, B-form geometry is inclusive of both C2'-endo pucker and O4'-endo pucker. This is consistent with Berger et. al., Nucleic Acids Research, 1998, 26, 2473-2480, who pointed out that in considering the furanose conformations which give rise to B-form duplexes consideration should also be given to a O4'-endo pucker contribution.

DNA:RNA hybrid duplexes, however, are usually less stable than pure RNA:RNA duplexes, and depending on their sequence may be either more or less stable than DNA:DNA duplexes (Searle et al., Nucleic Acids Res., 1993, 21, 2051-2056). The structure of a hybrid duplex is intermediate between A- and B-form geometries, which may result in poor stacking interactions (Lane et al., Eur. J. Biochem., 1993, 215, 297-306; Fedoroff et al., J. Mol. Biol., 1993, 233, 509-523; Gonzalez et al., Biochemistry, 1995, 34, 4969-4982; Horton et al., J. Mol. Biol., 1996, 264, 521-533). The stability of the duplex formed between a target RNA and a synthetic sequence is central to therapies such as but not limited to antisense and RNA interference as these mechanisms require the binding of a synthetic strand of oligomeric compound to an RNA target strand. In the case of antisense, effective inhibition of the mRNA requires that the antisense DNA have a very high binding affinity with the mRNA. Otherwise the desired interaction between the synthetic strand and target mRNA strand will occur infrequently, resulting in decreased efficacy.

One routinely used method of modifying the sugar puckering is the substitution of the sugar at the 2'-position with a substituent group that influences the sugar geometry. The influence on ring conformation is dependant on the nature of the substituent at the 2'-position. A number of different substituents have been studied to determine their sugar puckering effect. For example, 2'-halogens have been studied showing that the 2'-fluoro derivative exhibits the largest population (65%) of the C3'-endo form, and the 2'-iodo exhibits the lowest population (7%). The populations of adenosine (2'-OH) versus deoxyadenosine (2'-H) are 36% and 19%, respectively. Furthermore, the effect of the 2'-fluoro group of adenosine dimers (2'-deoxy-2'-fluoroadenosine-2'-deoxy-2'-fluoro-adenosine) is further correlated to the stabilization of the stacked conformation.

As expected, the relative duplex stability can be enhanced by replacement of 2'-OH groups with 2'-F groups thereby increasing the C3'-endo population. It is assumed that the highly polar nature of the 2'-F bond and the extreme preference for C3'-endo puckering may stabilize the stacked conformation in an A-form duplex. Data from UV hypochromicity, circular dichroism, and $^1$H NMR also indicate that the degree of stacking decreases as the electronegativity of the halo substituent decreases. Furthermore, steric bulk at the 2'-position of the sugar moiety is better accommodated in an A-form duplex than a B-form duplex. Thus, a 2'-substituent on the 3'-terminus of a dinucleoside monophosphate is thought to exert a number of effects on the stacking conformation: steric repulsion, furanose puckering preference, electrostatic repulsion, hydrophobic attraction, and hydrogen bonding capabilities. These substituent effects are thought to be determined by the molecular size, electronegativity, and hydrophobicity of the substituent. Melting temperatures of complementary strands is also increased with the 2'-substituted adenosine diphosphates. It is not clear whether the 3'-endo preference of the conformation or the presence of the substituent is responsible for the increased binding. However, greater overlap of adjacent bases (stacking) can be achieved with the 3'-endo conformation.

One synthetic 2'-modification that imparts increased nuclease resistance and a very high binding affinity to nucleotides is the 2-methoxyethoxy (2'-MOE, 2'-OCH$_2$CH$_2$OCH$_3$) side chain (Baker et al., J. Biol. Chem., 1997, 272, 11944-12000). One of the immediate advantages of the 2'-MOE substitution is the improvement in binding affinity, which is greater than many similar 2' modifications such as O-methyl, O-propyl, and O-aminopropyl. Oligonucleotides having the 2'-O-methoxyethyl substituent also have been shown to be antisense inhibitors of gene expression with promising features for in vivo use (Martin, P., Helv. Chim. Acta, 1995, 78, 486-504; Altmann et al., Chimia, 1996, 50, 168-176; Altmann et al., Biochem. Soc. Trans., 1996, 24, 630-637; and Altmann et al., Nucleosides Nucleotides, 1997, 16, 917-926). Relative to DNA, the oligonucleotides having the 2'-MOE modification displayed improved RNA affinity and higher nuclease resistance. Chimeric oligonucleotides having 2'-MOE substituents in the wing nucleosides and an internal region of deoxyphosphorothioate nucleotides (also termed a gapped oligonucleotide or gapmer) have shown effective reduction in the growth of tumors in animal models at low doses. 2'-MOE substituted oligonucleotides have also shown outstanding promise as antisense agents in several disease states. One such MOE substituted oligonucleotide is presently being investigated in clinical trials for the treatment of CMV retinitis.

To better understand the higher RNA affinity of 2'-O-methoxyethyl substituted RNA and to examine the conformational properties of the 2'-O-methoxyethyl substituent, two dodecamer oligonucleotides were synthesized having SEQ ID NO: 18 (CGC GAA UUC GCG) and SEQ ID NO: 19 (GCG CUU AAG CGC). These self-complementary strands have every 2'-position modified with a 2'-O-methoxyethyl. The duplex was crystallized at a resolution of 1.7 Ångstrom and the crystal structure was determined. The conditions used for the crystallization were 2 mM oligonucleotide, 50 mM Na Hepes pH 6.2-7.5, 10.50 mM MgCl$_2$, 15% PEG 400. The crystal data showed: space group C2, cell constants a=41.2 Å, b=34.4 Å, c=46.6 Å,=92.4°. The resolution was 1.7 Å at −170° C. The current R=factor was 20% (R$_{free}$ 26%).

This crystal structure is believed to be the first crystal structure of a fully modified RNA oligonucleotide analogue. The duplex adopts an overall A-form conformation and all modified sugars display C3'-endo pucker. In most of the 2'-O-substituents, the torsion angle around the A'-B' bond, as depicted in Structure II below, of the ethylene glycol linker has a gauche conformation. For 2'-O-MOE, A' and B' of Structure II below are methylene moieties of the ethyl portion of the MOE and R' is the methoxy portion.

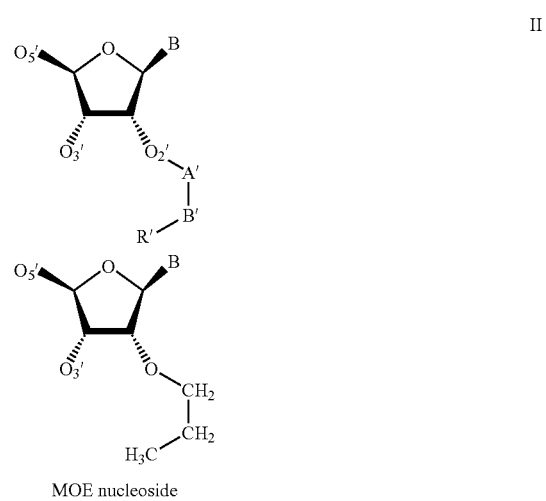

MOE nucleoside

In the crystal, the 2'-O-MOE RNA duplex adopts a general orientation such that the crystallographic 2-fold rotation axis does not coincide with the molecular 2-fold rotation axis. The duplex adopts the expected A-type geometry and all of the 24 2'-O-MOE substituents were visible in the electron density maps at full resolution. The electron density maps as well as the temperature factors of substituent atoms indicate flexibility of the 2'-O-MOE substituent in some cases.

Most of the 2'-O-MOE substituents display a gauche conformation around the C—C bond of the ethyl linker. However, in two cases, a trans conformation around the C—C bond is observed. The lattice interactions in the crystal include packing of duplexes against each other via their minor grooves. Therefore, for some residues, the conformation of the 2'-O-substituent is affected by contacts to an adjacent duplex. In general, variations in the conformation of the substituents (e.g. g$^+$ or g$^-$ around the C—C bonds) create a range of interactions between substituents, both inter-strand, across the minor groove, and intra-strand. At one location, atoms of substituents from two residues are in van der Waals contact across the minor groove. Similarly, a close contact occurs between atoms of substituents from two adjacent intra-strand residues.

Previously determined crystal structures of A-DNA duplexes were for those that incorporated isolated 2'-O-methyl T residues. In the crystal structure noted above for the 2'-O-MOE substituents, a conserved hydration pattern has been observed for the 2'-O-MOE residues. A single water molecule is seen located between O2', O3' and the methoxy oxygen atom of the substituent, forming contacts to all three of between 2.9 and 3.4 Å. In addition, oxygen atoms of substituents are involved in several other hydrogen bonding contacts. For example, the methoxy oxygen atom of a particular 2'-O-substituent forms a hydrogen bond to N3 of an adenosine from the opposite strand via a bridging water molecule.

In several cases a water molecule is trapped between the oxygen atoms O2', O3' and OC' of modified nucleosides. 2'-O-MOE substituents with trans conformation around the C—C bond of the ethylene glycol linker are associated with close contacts between OC' and N2 of a guanosine from the opposite strand, and, water-mediated, between OC' and N3(G). When combined with the available thermodynamic data for duplexes containing 2'-O-MOE modified strands, this crystal structure allows for further detailed structure-stability analysis of other modifications.

In extending the crystallographic structure studies, molecular modeling experiments were performed to study further enhanced binding affinity of oligonucleotides having 2'-O-modifications. The computer simulations were conducted on compounds of SEQ ID NO: 18, above, having 2'-O-modifications located at each of the nucleosides of the oligonucleotide. The simulations were performed with the oligonucleotide in aqueous solution using the AMBER force field method (Cornell et al., J. Am. Chem. Soc., 1995, 117, 5179-5197) (modeling software package from UCSF, San Francisco, Calif.). The calculations were performed on an Indigo2 SGI machine (Silicon Graphics, Mountain View, Calif.).

Further 2'-O-modifications that will have a 3'-endo sugar influence include those having a ring structure that incorporates a two atom portion corresponding to the A' and B' atoms of Structure II. The ring structure is attached at the 2' position of a sugar moiety of one or more nucleosides that are incorporated into an oligonucleotide. The 2'-oxygen of the nucleoside links to a carbon atom corresponding to the A' atom of Structure II. These ring structures can be aliphatic, unsaturated aliphatic, aromatic or heterocyclic. A further atom of the ring (corresponding to the B' atom of Structure II), bears a further oxygen atom, or a sulfur or nitrogen atom. This oxygen, sulfur or nitrogen atom is bonded to one or more hydrogen atoms, alkyl moieties, or haloalkyl moieties, or is part of a further chemical moiety such as a ureido, carbamate, amide or amidine moiety. The remainder of the ring structure restricts rotation about the bond joining these two ring atoms. This assists in positioning the "further oxygen, sulfur or nitrogen atom" (part of the R position as described above) such that the further atom can be located in close proximity to the 3'-oxygen atom (O3') of the nucleoside.

Another suitable 2'-sugar substituent group that gives a 3'-endo sugar conformational geometry is the 2'-OMe group. 2'-Substitution of guanosine, cytidine, and uridine dinucleoside phosphates with the 2'-OMe group showed enhanced stacking effects with respect to the corresponding native (2'-OH) species leading to the conclusion that the sugar is adopting a C3'-endo conformation. In this case, it is believed that the hydrophobic attractive forces of the methyl group tend to overcome the destabilizing effects of its steric bulk.

The ability of oligonucleotides to bind to their complementary target strands is compared by determining the melting temperature ($T_m$) of the hybridization complex of the oligonucleotide and its complementary strand. The melting temperature ($T_m$), a characteristic physical property of double helices, denotes the temperature (in degrees centigrade) at which 50% helical (hybridized) versus coil (unhybridized) forms are present. $T_m$ is measured by using the UV spectrum to determine the formation and breakdown (melting) of the hybridization complex. Base stacking, which occurs during hybridization, is accompanied by a reduction in UV absorption (hypochromicity). Consequently, a reduction in UV absorption indicates a higher $T_m$. The higher the $T_m$, the greater the strength of the bonds between the strands.

Freier and Altmann, Nucleic Acids Research, 1997, 25, 4429-4443, have previously published a study on the influence of structural modifications of oligonucleotides on the stability of their duplexes with target RNA. In this study, the authors reviewed a series of oligonucleotides containing more than 200 different modifications that had been synthesized and assessed for their hybridization affinity and Tm. Sugar modifications studied included substitutions on the 2'-position of the sugar, 3'-substitution, replacement of the 4'-oxygen, the use of bicyclic sugars, and four member ring replacements. Several nucleobase modifications were also studied including substitutions at the 5, or 6 position of thymine, modifications of pyrimidine heterocycle and modifications of the purine heterocycle. Modified internucleoside linkages were also studied including neutral, phosphorus and non-phosphorus containing internucleoside linkages.

Increasing the percentage of C3'-endo sugars in a modified oligonucleotide targeted to an RNA target strand should preorganize this strand for binding to RNA. Of the several sugar modifications that have been reported and studied in the literature, the incorporation of electronegative substituents such as 2'-fluoro or 2'-alkoxy shift the sugar conformation towards the 3' endo (northern) pucker conformation. This preorganizes an oligonucleotide that incorporates such modifications to have an A-form conformational geometry. This A-form conformation results in increased binding affinity of the oligonucleotide to a target RNA strand.

Molecular modeling experiments were performed to study further enhanced binding affinity of oligonucleotides having 2'-O-modifications. Computer simulations were conducted on compounds having r(CGC GAA UUC GCG) (SEQ ID NO: 18), having 2'-O-modifications of the invention located at each of the nucleoside of the oligonucleotide. The simulations were performed with the oligonucleotide in aqueous solution using the AMBER force field method (Cornell et al., J. Am. Chem. Soc., 1995, 117, 5179-5197) (modeling software package from UCSF, San Francisco, Calif.). The calculations were performed on an Indigo2 SGI machine (Silicon Graphics, Mountain View, Calif.).

In addition, for 2'-substituents containing an ethylene glycol motif, a gauche interaction between the oxygen atoms around the O—C—C—O torsion of the side chain may have a stabilizing effect on the duplex (Freier ibid.). Such gauche interactions have been observed experimentally for a number of years (Wolfe et al., Acc. Chem. Res., 1972, 5, 102; Abe et al., J. Am. Chem. Soc., 1976, 98, 468). This gauche effect may result in a configuration of the side chain that is favorable for duplex formation. The exact nature of this stabilizing configuration has not yet been explained. While we do not want to be bound by theory, it may be that holding the O—C—C—O torsion in a single gauche configuration, rather than a more random distribution seen in an alkyl side chain, provides an entropic advantage for duplex formation.

Representative 2'-substituent groups amenable to the present invention that give A-form conformational properties (3'-endo) to the resultant duplexes include 2'-O-alkyl, 2'-O-substituted alkyl and 2'-fluoro substituent groups. Suitable substituent groups are various alkyl and aryl ethers and thioethers, amines and monoalkyl and dialkyl substituted amines. It is further intended that multiple modifications can be made to one or more of the oligomeric compounds of the invention at multiple sites of one or more monomeric subunits (nucleosides are suitable) and or internucleoside linkages to enhance properties such as but not limited to activity in a selected application. Tables 2 through 8 list nucleoside and internucleotide linkage modifications/replacements that have been shown to give a positive εTm per modification when the modification/replacement was made to a DNA strand that was hybridized to an RNA complement.

Substitution at $R_1$ can be stabilizing, substitution at $R_2$ is generally greatly destabilizing (unable to form anti conformation), motiffs with stabilizing 5 and 2'-substituent groups are generally additive e.g. increase stability.

Substitution of the O4 and O2 positions of 2'-O-methyl uridine was greatly duplex destabilizing as these modifications remove hydrogen binding sites that would be an expected result. 6-Aza T also showed extreme destabilization as this substitution reduces the $pK_a$ and shifts the nucleoside toward the enol tautomer resulting in reduced hydrogen bonding.

Suitable ring structures of the invention for inclusion as a 2'-O modification include cyclohexyl, cyclopentyl and phenyl rings as well as heterocyclic rings having spacial footprints similar to cyclohexyl, cyclopentyl and phenyl rings. Particularly suitable 2'-O-substituent groups of the invention are listed below including an abbreviation for each:
2'-O-(trans 2-methoxy cyclohexyl)—2'-O-(TMCHL)
2'-O-(trans 2-methoxy cyclopentyl)—2'-O-(TMCPL)
2'-O-(trans 2-ureido cyclohexyl)—2'-O-(TUCHL)
2'-O-(trans 2-methoxyphenyl)—2'-O-(2MP)

Structural details for duplexes incorporating such 2-O-substituents were analyzed using the described AMBER force field program on the Indigo2 SGI machine. The simulated structure maintained a stable A-form geometry throughout the duration of the simulation. The presence of the 2' substitutions locked the sugars in the C3'-endo conformation.

The simulation for the TMCHL modification revealed that the 2'-0-(TMCHL) side chains have a direct interaction with water molecules solvating the duplex. The oxygen atoms in the 2'-O-(TMCHL) side chain are capable of forming a water-mediated interaction with the 3' oxygen of the phosphate backbone. The presence of the two oxygen atoms in the 2'-O-(TMCHL) side chain gives rise to favorable gauche interactions. The barrier for rotation around the O—C—C—O torsion is made even larger by this novel modification. The preferential preorganization in an A-type geometry increases the binding affinity of the 2'-O-(TMCHL) to the target RNA. The locked side chain conformation in the 2'-O-(TMCHL) group created a more favorable pocket for binding water molecules. The presence of these water molecules played a key role in holding the side chains in the preferable gauche conformation. While not wishing to be bound by theory, the bulk of the substituent, the diequatorial orientation of the substituents in the cyclohexane ring, the water of hydration and the potential for trapping of metal ions in the conformation generated will additionally contribute to improved binding affinity and nuclease resistance of oligonucleotides incorporating nucleosides having this 2'-O-modification.

As described for the TMCHL modification above, identical computer simulations of the 2'-O-(TMCPL), the 2'-O-(2MP) and 2'-O-(TUCHL) modified oligonucleotides in aqueous solution also illustrate that stable A-form geometry will be maintained throughout the duration of the simulation. The presence of the 2' substitution will lock the sugars in the C3'-endo conformation and the side chains will have direct interaction with water molecules solvating the duplex. The oxygen atoms in the respective side chains are capable of forming a water-mediated interaction with the 3' oxygen of the phosphate backbone. The presence of the two oxygen atoms in the respective side chains give rise to the favorable gauche interactions. The barrier for rotation around the respective O—C—C—O torsions will be made even larger by respective modification. The preferential preorganization in A-type geometry will increase the binding affinity of the respective 2'-O-modified oligonucleotides to the target RNA. The locked side chain conformation in the respective modifications will create a more favorable pocket for binding water molecules. The presence of these water molecules plays a key role in holding the side chains in the preferable gauche conformation. The bulk of the substituent, the diequatorial orientation of the substituents in their respective rings, the water of hydration and the potential trapping of metal ions in the conformation generated will all contribute to improved binding affinity and nuclease resistance of oligonucleotides incorporating nucleosides having these respective 2'-O-modification.

Ribose conformations in C2'-modified nucleosides containing S-methyl groups were examined. To understand the influence of 2'-O-methyl and 2'-S-methyl groups on the conformation of nucleosides, we evaluated the relative energies of the 2'-O- and 2'-S-methylguanosine, along with normal deoxyguanosine and riboguanosine, starting from both C2'-endo and C3'-endo conformations using ab initio quantum mechanical calculations. All the structures were fully optimized at HF/6-31G* level and single point energies with electron-correlation were obtained at the MP2/6-31G*//HF/6-31G* level. As shown in Table 9, the C2'-endo conformation of deoxyguanosine is estimated to be 0.6 kcal/mol more stable than the C3'-endo conformation in the gas-phase. The conformational preference of the C2'-endo over the C3'-endo conformation appears to be less dependent upon electron correlation as revealed by the MP2/6-31G*//HF/6-31G* values which also predict the same difference in energy. The opposite trend is noted for riboguanosine. At the HF/6-31G* and MP2/6-31 G*//HF/6-31G* levels, the C3'-endo form of riboguanosine is shown to be about 0.65 and 1.41 kcal/mol more stable than the C2'endo form, respectively.

Table 9 also includes the relative energies of 2'-O-methylguanosine and 2'-S-methylguanosine in C2'-endo and C3'-endo conformation. This data indicates the electronic nature of C2'-substitution has a significant impact on the relative stability of these conformations. Substitution of the 2'-O-methyl group increases the preference for the C3'-endo conformation (when compared to riboguanosine) by about 0.4 kcal/mol at both the HF/6-31G* and MP2/6-31G*//HF/6-31G* levels. In contrast, the 2'-S-methyl group reverses the trend. The C2'-endo conformation is favored by about 2.6 kcal/mol at the HF/6-31G* level, while the same difference is reduced to 1.41 kcal/mol at the MP2/6-31G*//HF/6-31G* level. For comparison, and also to evaluate the accuracy of the molecular mechanical force-field parameters used for the 2'-O-methyl and 2'-S-methyl substituted nucleosides, we have calculated the gas phase energies of the nucleosides. The results reported in Table 9 indicate that the calculated relative energies of these nucleosides compare qualitatively well with the ab initio calculations.

Additional calculations were also performed to gauge the effect of solvation on the relative stability of nucleoside conformations. The estimated solvation effect using HF/6-31G* geometries confirms that the relative energetic preference of the four nucleosides in the gas-phase is maintained in the aqueous phase as well (Table 9). Solvation effects were also examined using molecular dynamics simulations of the nucleosides in explicit water. From these trajectories, one can observe the predominance of C2'-endo conformation for deoxyriboguanosine and 2'-S-methylriboguanosine while riboguanosine and 2'-O-methylriboguanosine prefer the C3'-endo conformation. These results are in much accord with the available NMR results on 2'-S-methylribonucleosides. NMR studies of sugar puckering equilibrium using vicinal spin-coupling constants have indicated that the conformation of the sugar ring in 2'-S-methylpyrimidine nucleosides show an average of >75% S-character, whereas the corresponding purine analogs exhibit an average of >90% S-pucker (Fraser et al., J. Heterocycl. Chem., 1993, 30, 1277-1287). It was observed that the 2'-S-methyl substitution in deoxynucleoside confers more conformational rigidity to the sugar conformation when compared with deoxyribonucleosides.

Structural features of DNA:RNA, OMe-DNA:RNA and SMe-DNA:RNA hybrids were also observed. The average RMS deviation of the DNA:RNA structure from the starting hybrid coordinates indicate the structure is stabilized over the length of the simulation with an approximate average RMS deviation of 1.0 Å. This deviation is due, in part, to inherent differences in averaged structures (i.e. the starting conformation) and structures at thermal equilibrium. The changes in sugar pucker conformation for three of the central base pairs of this hybrid are in good agreement with the observations made in previous NMR studies. The sugars in the RNA strand maintain very stable geometries in the C3'-endo conformation with ring pucker values near 0°. In contrast, the sugars of the DNA strand show significant variability.

The average RMS deviation of the OMe-DNA:RNA is approximately 1.2 Å from the starting A-form conformation; while the SMe-DNA:RNA shows a slightly higher deviation (approximately 1.8 Å) from the starting hybrid conformation. The SMe-DNA strand also shows a greater variance in RMS deviation, suggesting the S-methyl group may induce some structural fluctuations. The sugar puckers of the RNA complements maintain C3'-endo puckering throughout the simulation. As expected from the nucleoside calculations, however, significant differences are noted in the puckering of the OMe-DNA and SMe-DNA strands, with the former adopting C3'-endo, and the latter, C1'-exo/C2'-endo conformations.

An analysis of the helicoidal parameters for all three hybrid structures has also been performed to further characterize the duplex conformation. Three of the more important axis-base-pair parameters that distinguish the different forms of the duplexes, X-displacement, propeller twist, and inclination, are reported in Table 10. Usually, an X-displacement near zero represents a B-form duplex; while a negative displacement, which is a direct measure of deviation of the helix from the helical axis, makes the structure appear more A-like in conformation. In A-form duplexes, these values typically vary from −4 Å to −5 Å. In comparing these values for all three hybrids, the SMe_DNA:RNA hybrid shows the most deviation from the A-form value, the OMe_DNA:RNA shows the least, and the DNA:RNA is intermediate. A similar trend is also evident when comparing the inclination and propeller twist values with ideal A-form parameters. These results are further supported by an analysis of the backbone and glycosidic torsion angles of the hybrid structures. Glycosidic angles (X) of A-form geometries, for example, are typically near −159° while B form values are near −102°. These angles are found to be −162°, −133°, and −108° for the OMe-DNA, DNA, and SMe-DNA strands, respectively. All RNA complements adopt an X angle close to −160°. In addition, "crankshaft" transitions were also noted in the backbone torsions of the central UpU steps of the RNA strand in the SMe-DNA:RNA and DNA;RNA hybrids. Such transitions suggest some local conformational changes may occur to relieve a less favorable global conformation. Taken overall, the results indicate the amount of A-character decreases as OMe-DNA:RNA>DNA:RNA>SMe-DNA:RNA, with the latter two adopting more intermediate conformations when compared to A- and B-form geometries.

Stability of C2'-modified DNA:RNA hybrids was determined. Although the overall stability of the DNA:RNA hybrids depends on several factors including sequence-dependencies and the purine content in the DNA or RNA strands DNA:RNA hybrids are usually less stable than RNA:RNA duplexes and, in some cases, even less stable than DNA:DNA duplexes. Available experimental data attributes the relatively lowered stability of DNA:RNA hybrids largely to its intermediate conformational nature between DNA:DNA (B-family) and RNA:RNA (A-family) duplexes. The overall thermodynamic stability of nucleic acid duplexes may originate from several factors including the conformation of backbone, base-pairing and stacking interactions. While it is difficult to ascertain the individual thermodynamic contributions to the overall stabilization of the duplex, it is reasonable to argue that the major factors that promote increased stability of hybrid duplexes are better stacking interactions (electrostatic π-π interactions) and more favorable groove dimensions for hydration. The C2'-S-methyl substitution has been shown to destabilize the hybrid duplex. The notable differences in the rise values among the three hybrids may offer some explanation. While the 2'-S-methyl group has a strong influence on decreasing the base-stacking through high rise values (~3.2 Å), the 2'-O-methyl group makes the overall structure more compact with a rise value that is equal to that of A-form duplexes (~2.6 Å). Despite its overall A-like structural features, the SMe_DNA:RNA hybrid structure possesses an average rise value of 3.2 Å which is quite close to that of B-family duplexes. In fact, some local base-steps (CG steps) may be observed to have unusually high rise values (as high as 4.5 Å). Thus, the greater destabilization of 2'-S-methyl substituted DNA:RNA hybrids may be partly attributed to poor stacking interactions.

It has been postulated that RNase H binds to the minor groove of RNA:DNA hybrid complexes, requiring an intermediate minor groove width between ideal A- and B-form geometries to optimize interactions between the sugar phosphate backbone atoms and RNase H. A close inspection of the averaged structures for the hybrid duplexes using computer simulations reveals significant variation in the minor groove width dimensions as shown in Table 3. Whereas the O-methyl substitution leads to a slight expansion of the minor groove width when compared to the standard DNA:RNA complex, the S-methyl substitution leads to a general contraction (approximately 0.9 Å). These changes are most likely due to the preferred sugar puckering noted for the antisense strands which induce either A- or B-like single strand conformations. In addition to minor groove variations, the results also point to potential differences in the steric makeup of the minor groove. The O-methyl group points into the minor groove while the S-methyl is directed away towards the major groove. Essentially, the S-methyl group has flipped through the bases into the major groove as a consequence of C2'-endo puckering.

Unless otherwise defined herein, alkyl means $C_1$-$C_{12}$, $C_1$-$C_8$, or $C_1$-$C_6$, straight or (where possible) branched chain aliphatic hydrocarbyl.

Unless otherwise defined herein, heteroalkyl means $C_1$-$C_{12}$, $C_1$-$C_8$, or $C_1$-$C_6$, straight or (where possible) branched chain aliphatic hydrocarbyl containing at least one or about 1 to about 3, hetero atoms in the chain, including the terminal portion of the chain. Suitable heteroatoms include N, O and S.

Unless otherwise defined herein, cycloalkyl means $C_3$-$C_{12}$, $C_3$-$C_8$, or $C_3$-$C_6$, aliphatic hydrocarbyl ring.

Unless otherwise defined herein, alkenyl means $C_2$-$C_{12}$, $C_2$-$C_8$, or $C_2$-$C_6$ alkenyl, which may be straight or (where possible) branched hydrocarbyl moiety, which contains at least one carbon-carbon double bond.

Unless otherwise defined herein, alkynyl means $C_2$-$C_{12}$, $C_2$-$C_8$, or $C_2$-$C_6$ alkynyl, which may be straight or (where possible) branched hydrocarbyl moiety, which contains at least one carbon-carbon triple bond.

Unless otherwise defined herein, heterocycloalkyl means a ring moiety containing at least three ring members, at least one of which is carbon, and of which 1, 2 or three ring members are other than carbon. The number of carbon atoms can vary from 1 to about 12, from 1 to about 6, and the total number of ring members varies from three to about 15, or from about 3 to about 8. Suitable ring heteroatoms are N, O and S. Suitable heterocycloalkyl groups include, but are not limited to, morpholino, thiomorpholino, piperidinyl, piperazinyl, homopiperidinyl, homopiperazinyl, homomorpholino, homothiomorpholino, pyrrolodinyl, tetrahydrooxazolyl, tetrahydroimidazolyl, tetrahydrothiazolyl, tetrahydroisoxazolyl, tetrahydropyrrazolyl, furanyl, pyranyl, and tetrahydroisothiazolyl.

Unless otherwise defined herein, aryl means any hydrocarbon ring structure containing at least one aryl ring. Suitable aryl rings have about 6 to about 20 ring carbons. In addition, suitable aryl rings include phenyl, napthyl, anthracenyl, and phenanthrenyl.

Unless otherwise defined herein, hetaryl means a ring moiety containing at least one fully unsaturated ring, the ring consisting of carbon and non-carbon atoms. The ring system can contain about 1 to about 4 rings. The number of carbon atoms can vary from 1 to about 12, from 1 to about 6, and the total number of ring members varies from three to about 15, or from about 3 to about 8. Suitable ring heteroatoms are N, O and S. Suitable hetaryl moieties include, but are not limited to, pyrazolyl, thiophenyl, pyridyl, imidazolyl, tetrazolyl, pyridyl, pyrimidinyl, purinyl, quinazolinyl, quinoxalinyl, benzimidazolyl, benzothiophenyl, etc.

Unless otherwise defined herein, where a moiety is defined as a compound moiety, such as hetarylalkyl (hetaryl and alkyl), aralkyl (aryl and alkyl), etc., each of the sub-moieties is as defined herein.

Unless otherwise defined herein, an electron withdrawing group is a group, such as the cyano or isocyanato group that draws electronic charge away from the carbon to which it is attached. Other electron withdrawing groups of note include those whose electronegativities exceed that of carbon, for example halogen, nitro, or phenyl substituted in the ortho- or para-position with one or more cyano, isothiocyanato, nitro or halo groups.

Unless otherwise defined herein, the terms halogen and halo have their ordinary meanings. Suitable halo (halogen) substituents are Cl, Br, and I.

The aforementioned optional substituents are, unless otherwise herein defined, suitable substituents depending upon desired properties. Included are halogens (Cl, Br, I), alkyl, alkenyl, and alkynyl moieties, $NO_2$, $NH_3$ (substituted and unsubstituted), acid moieties (e.g. $-CO_2H$, $-OSO_3H_2$, etc.), heterocycloalkyl moieties, hetaryl moieties, aryl moieties, etc.

In all the preceding formulae, the squiggle (~) indicates a bond to an oxygen or sulfur of the 5'-phosphate. Phosphate protecting groups include those described in U.S. Pat. Nos. 5,760,209, 5,614,621, 6,051,699, 6,020,475, 6,326,478, 6,169,177, 6,121,437, 6,465,628.

Oligomerization of modified and unmodified nucleosides is performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al., Tetrahedron, 2001, 57, 5707-5713) synthesis as appropriate. In addition, specific protocols for the synthesis of oligomeric compounds of the invention are illustrated in the examples below.

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The present invention is also useful for the preparation of oligomeric compounds incorporating at least one 2'-O-protected nucleoside. After incorporation and appropriate deprotection the 2'-O-protected nucleoside will be converted to a ribonucleoside at the position of incorporation. The number and position of the 2-ribonucleoside units in the final oligomeric compound can vary from one at any site or the strategy can be used to prepare up to a full 2'-OH modified oligomeric compound. All 2'-O-protecting groups amenable to the synthesis of oligomeric compounds are included in the present invention. In general a protected nucleoside is attached to a solid support by for example a succinate linker. Then the oligonucleotide is elongated by repeated cycles of deprotecting the 5'-terminal hydroxyl group, coupling of a further nucleoside unit, capping and oxidation (alternatively sulfurization). In a more frequently used method of synthesis the completed oligonucleotide is cleaved from the solid support with the removal of phosphate protecting groups and exocyclic amino protecting groups by treatment with an ammonia solution. Then a further deprotection step is normally required for removal of the more specialized protecting groups used for the protection of 2'-hydroxyl groups thereby affording the fully deprotected oligonucleotide.

A large number of 2'-O-protecting groups have been used for the synthesis of oligoribonucleotides but over the years more effective groups have been discovered. The key to an effective 2'-O-protecting group is that it is capable of selectively being introduced at the 2'-O-position and that it can be removed easily after synthesis without the formation of unwanted side products. The protecting group also needs to be inert to the normal deprotecting, coupling, and capping steps required for oligoribonucleotide synthesis. Some of the protecting groups used initially for oligoribonucleotide synthesis included tetrahydropyran-1-yl and 4-methoxytetrahydropyran-4-yl. These two groups are not compatible with all 5'-O-protecting groups so modified versions were used with 5'-DMT groups such as 1-(2-fluorophenyl)-4-methoxypiperidin-4-yl (Fpmp). Reese has identified a number of piperidine derivatives (like Fpmp) that are useful in the synthesis of oligoribonucleotides including 1-((chloro-4-methyl)phenyl)-4'-methoxypiperidin-4-yl (Reese et al., Tetrahedron Lett., 1986, (27), 2291). Another approach was to replace the standard 5'-DMT (dimethoxytrityl) group with protecting groups that were removed under non-acidic conditions such as levulinyl and 9-fluorenylmethoxycarbonyl. Such groups enable the use of acid labile 2'-protecting groups for oligoribonucleotide synthesis. Another more widely used protecting group initially used for the synthesis of oligoribonucleotides was the t-butyldimethylsilyl group (Ogilvie et al., Tetrahedron Lett., 1974, 2861; Hakimelahi et al., Tetrahedron Lett., 1981, (22), 2543; and Jones et al., J. Chem. Soc. Perkin I., 2762). The 2'-O-protecting groups can require special reagents for their removal such as for example the t-butyldimethylsilyl group is normally removed after all other cleaving/deprotecting steps by treatment of the oligomeric compound with tetrabutylammonium fluoride (TBAF).

One group of researchers examined a number of 2'-O-protecting groups (Pitsch, S., Chimia, 2001, 55, 320-324).

The group examined fluoride labile and photolabile protecting groups that are removed using moderate conditions. One photolabile group that was examined was the (2-(nitrobenzyl)oxy)methyl (nbm) protecting group (Schwartz et al., Bioorg. Med. Chem. Lett., 1992, 2, 1019). Other groups examined included a number structurally related formaldehyde acetal-derived, 2'-O-protecting groups. Also prepared were a number of related protecting groups for preparing 2'-O-alkylated nucleoside phosphoramidites including 2'-O-((triisopropylsilyl)oxy)methyl (2'-O—$CH_2$—O—$Si(iPr)_3$; TOM). One 2'-O-protecting group that was prepared to be used orthogonally to the TOM group was 2'-O—((R)—1-(2-nitrophenyl)ethyloxy)methyl) ((R)-mnbm).

Another strategy using a fluoride labile 5'-O-protecting group (non-acid labile) and an acid labile 2'-O-protecting group has been reported (Scaringe, Stephen A., Methods, 2001, (23) 206-217). A number of possible silyl ethers were examined for 5'-O-protection and a number of acetals and orthoesters were examined for 2'-O-protection. The protection scheme that gave the best results was 5'-O-silyl ether-2'-ACE (5'-O-bis(trimethylsiloxy)cyclododecyloxysilyl ether (DOD)-2'-O-bis(2-acetoxyethoxy)methyl (ACE). This approach uses a modified phosphoramidite synthesis approach in that some different reagents are required that are not routinely used for RNA/DNA synthesis.

Although a lot of research has focused on the synthesis of oligoribonucleotides the main RNA synthesis strategies that are presently being used commercially include 5'-O-DMT-2'-O-t-butyldimethylsilyl (TBDMS), 5'-O-DMT-2'-O-(1(2-fluorophenyl)-4-methoxypiperidin-4-yl) (FPMP), 2'-O-((triisopropylsilyl)oxy)methyl (2'-O—$CH_2$—O—$Si(iPr)_3$ (TOM), and the 5'-O-silyl ether-2'-ACE (5'-O-bis(trimethylsiloxy)cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries. Such an activator would also be amenable to the present invention.

The primary groups being used for commercial RNA synthesis are:
TBDMS=5'-O-DMT-2'-O-t-butyldimethylsilyl;
TOM=2'-O-((triisopropylsilyl)oxy)methyl;
DOD/ACE=(5'-O-bis(trimethylsiloxy)cyclododecyloxysilyl ether-2'-O-bis(2-acetoxyethoxy)methyl
FPMP=5'-O-DMT-2'-O-(1(2-fluorophenyl)-4-methoxypiperidin-4-yl).

All of the aforementioned RNA synthesis strategies are amenable to the present invention. Strategies that would be a hybrid of the above e.g. using a 5'-protecting group from one strategy with a 2'-O-protecting from another strategy is also amenable to the present invention.

The preparation of ribonucleotides and oligomeric compounds having at least one ribonucleoside incorporated and all the possible configurations falling in between these two extremes are encompassed by the present invention. The corresponding oligomeric compounds can be hybridized to further oligomeric compounds including oligoribonucleotides having regions of complementarity to form double-stranded (duplexed) oligomeric compounds. Such double stranded oligonucleotide moieties have been shown in the art to modulate target expression and regulate translation as well as RNA processsing via an antisense mechanism. Moreover, the double-stranded moieties may be subject to chemical modifications (Fire et al., Nature, 1998, 391, 806-811; Timmons and Fire, Nature 1998, 395, 854; Timmons et al., Gene, 2001, 263, 103-112; Tabara et al., Science, 1998, 282, 430-431; Montgomery et al., Proc. Natl. Acad. Sci. USA, 1998, 95, 15502-15507; Tuschl et al., Genes Dev., 1999, 13, 3191-3197; Elbashir et al., Nature, 2001, 411, 494-498; Elbashir et al., Genes Dev. 2001, 15, 188-200). For example, such double-stranded moieties have been shown to inhibit the target by the classical hybridization of antisense strand of the duplex to the target, thereby triggering enzymatic degradation of the target (Tijsterman et al., Science, 2002, 295, 694-697).

The methods of preparing oligomeric compounds of the present invention can also be applied in the areas of drug discovery and target validation. The present invention comprehends the use of the oligomeric compounds and suitable targets identified herein in drug discovery efforts to elucidate relationships that exist between proteins and a disease state, phenotype, or condition. These methods include detecting or modulating a target peptide comprising contacting a sample, tissue, cell, or organism with the oligomeric compounds of the present invention, measuring the nucleic acid or protein level of the target and/or a related phenotypic or chemical endpoint at some time after treatment, and optionally comparing the measured value to a non-treated sample or sample treated with a further oligomeric compound of the invention. These methods can also be performed in parallel or in combination with other experiments to determine the function of unknown genes for the process of target validation or to determine the validity of a particular gene product as a target for treatment or prevention of a particular disease, condition, or phenotype.

Effect of nucleoside modifications on RNAi activity is evaluated according to existing literature (Elbashir et al., Nature, 2001, 411, 494-498; Nishikura et al., Cell, 2001, 107, 415-416; and Bass et al., Cell, 2000, 101, 235-238.)

In order that the invention disclosed herein may be more efficiently understood, examples are provided below. It should be understood that these examples are for illustrative purposes only and are not to be construed as limiting the invention in any manner. Throughout these examples, molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted.

EXAMPLES

Example 1

Animals

Balb/c mice, 18-24 g (5-7 weeks old), were obtained from Charles River (Wilmington Mass.) and used for subsequent in vitro and in vivo experiments. Animals were housed in polycarbonate cages and given access to chow and water ad libitum, in accordance with protocols approved by the Institutional Animal Care and Use Committee.

Example 2

Oligonucleotides

All chimeric MOE Gapmers are 20-mer phosphorothioate oligodeoxynucleotides containing 2'-O-methoxyethyl (2'-MOE) modifications at positions 1-5 and 16-20. MOE Gapmers and the 2'-deoxy unmodified phosphorothioate oligodeoxynucleotides ODN-PTEN and ODN-PTEN(6MM) were synthesized on a Milligen model 8800 DNA synthesizer (Millipore Inc., Bedford Mass.) using conventional solid-phase triester chemistry (Sanghvi, 1999) at Isis Pharmaceuticals Inc. Deprotected and desalted siRNA analogs were obtained from Dharmacon Research, Inc. (LaFayette, Colo.). Sequences of siRNA compounds, and the oligonucleotides and placement of their 2'-O-methoxyethyl modifications, are detailed in Table 12. 2'-MOE Gapmers (MG) are first generation 20-mer phosphorothioate oligodeoxynucleotides which contain 2'-O-methoxyethyl (2'-MOE) modifications at positions 1-5 and 16-20 (boldface type). ISIS 160847 and 160848 are first generation phosphorothioate oligodeoxynucleotides (ODN). Both antisense and sense strands are shown for each siRNA construct (si). Six-base mismatch (6MM) control oligonucleotides are of similar nucleoside composition as the respective antisense oligonucleotides.

Example 3

In Vitro Analysis

Primary hepatocyte isolation/culture. Mouse hepatocytes were isolated from mice using a two step in situ liver perfusion as previously described (McQueen et al., Cell. Biol. Toxicol., 1989, 5, 201-206). Briefly, animals were anesthetized with Avertin (50 mg/kg, intraperitoneal) and the portal vein was exposed. Hank's Balanced Salt Solution (Life Technologies, Grand Island, N.Y.) was perfused through the portal vein for 3.5 min at 2 ml/min followed by Williams Medium E (WME: Life Technologies, Grand Island, N.Y.) containing 0.3 mg/ml collagenase B (Roche Molecular Biochemicals, Indianapolis, Ind.) for 5.5 minutes. The liver was removed from the animal and gently massaged through Nitex nylon mesh (Tetko, Depew, N.Y.) to obtain a suspension of cells. The suspension was centrifuged (4 minutes at 500 rpm) and the supernatant discarded. The remaining pellet was gently resuspended in WME and centrifuged (4 minutes at 500 rpm) two more times to remove nonparenchymal cells. The pelleted hepatocytes were resuspended in WME supplemented with 10% fetal bovine serum (FBS)(v:v) and the concentration of cells was determined. For plating, cells were resuspended to the desired working concentration in WME supplemented with 10% FBS, 1% L-glutamine (v:v), 1% HEPES (v:v), and 1% gentamycin (antimitotic-antibiotic). Cells were plated on Primaria™ coated 6-well plates at a density of 100,000 per ml or Primaria™ 96-well coated plates at a density of 10,000 per ml. Cells were allowed to adhere to plates for one hour and then gently washed with PBS to remove dead cells and the media replaced with fresh HepatoZYME™ media (Invitrogen, Carlsbad, Calif.) supplemented with 1% L-glutamine (v:v), 1% HEPES (v:v), 1% non-essential amino acids (NEAA) and 1% gentamycin (antimitotic-antibiotic).

In vitro hepatocyte oligodeoxynucleotide transfections. For experiments transfecting primary hepatocytes with cationic lipids, transfections were performed either four hours after plating or after an additional 8-12 hours (overnight). No difference in transfection results were observed comparing the two plating intervals (data not shown). The oligonucleotide or siRNA (oligo/siRNA) was mixed with Lipofectin (Invitrogen, Carlsbad, Calif.) at a working concentration of 3 μg per 100 nM of single strand DNA or RNA per 1 ml of media. Prior to addition to cells, the mix was incubated 5-10 minutes as per vendor recommendations. Plating media was then removed and the cells were treated for 4-6 hours, the media changed to fresh HepatoZYME™ (supplemented as above) and cells incubated overnight for an additional 16-20 hours. Cells were then lysed and the RNA isolated and purified as described below. For free uptake studies, cells were allowed to adhere to the plastic for 4 hours then treated with the oligos/siRNA in the HepatoZYME™ media for 12-16 hours (overnight). Cells were then lysed and the RNA isolated and purified as described below.

RNA isolation and expression analysis. In vitro total RNA was harvested at the indicated times post-transfection using the RNeasy Mini kit (Qiagen, Valencia, Calif.) for the 6-well treatments and using the Qiagen BioRobot 3000 for the 96-well plates, according to the manufacturers protocol. Gene expression was determined via real time quantitative RT-PCR on the ABI Prism 7700 system (Applied Biosystems, Foster City Calif.) as suggested by the manufacturer and described in the literature (Gibson et al., Genome Res., 1996, 6, 995-1001; Winer et al., Anal. Biochem., 1999, 270, 41-49; and Vickers et al., J. Biol. Chem., 2003, 278, 7108-7118). Primers and probes were obtained from IDT, Inc. (Coralville, Iowa) and the following primer/probe sets were used: PTEN (accession number U92437.1), forward primer (ATGACAATCATGTTGCAGCAATTC; SEQ ID NO:1), reverse primer (CGATGCAATAAATATGCACAAATCA; SEQ ID NO:2), and probe (GTAAAGCTGGAAAGGGACGGACTGGT; SEQ ID NO:3); Fas (accession number M83649.1), forward primer (TCCAAGACACAGCTGAGCAGA; SEQ ID NO:4), reverse primer (TGCATCACTCTTCCCATGAGAT; SEQ ID NO:5), and probe (AGTCCAGCTGCTCCTGTGCTGGTACC; SEQ ID NO:6); Apolipoprotein B (accession number M35186.1), forward primer (CGTGGGCTCCAGCATTCTA; SEQ ID NO:7), reverse primer (AGTCATTTCTGCCTTTGCGTC; SEQ ID NO:8), and probe (CCAATGGTCGGGCACTGCTCAA; SEQ ID NO:9); Microsomal triglyceride transfer protein (accession number NM_008642.1), forward primer (GAGCGGTCTGGATTTACAACG; SEQ ID NO: 10), reverse primer (AGGTAGTGACAGATGTGGCTTTTG; SEQ ID NO:11), and probe (CAAACCAGGTGCTGGGCGTCAGT; SEQ ID NO: 12); and murine cyclophilin A (accession number), forward primer (TCGCCGCTTGCTGCA; SEQ ID NO:13), reverse primer (ATCGGCCGTGATGTCGA; SEQ ID NO: 14) and probe (CCATGGTCAACCCCACCGTGTTC; SEQ ID NO:15). Cyclophilin A mRNA levels were used with 96-well transfection experiments as an internal standard for sample to sample normalization. All mRNA expression levels were normalized both to RiboGreen (Molecular Probes, Eugene, Oreg.), and GAPDH mRNA, also determined by quantitative RT-PCR (data not shown), from the same total RNA samples. Dose-response trends were independent of the normalization technique, and only RiboGreen normalized data is presented here.

Statistical Analysis. Simple Student's T-Test were performed.

Primary hepatocyte monolayer model. Mouse primary hepatocytes plated in 6-well plates were dosed with ISIS 116847(MG-PTEN), a MOE gapmer specific for PTEN (Butler et al., Diabetes, 2002, 51, 1028-1034), at 25 and 100 nM in the presence of lipofectin. PTEN mRNA expression levels fell in a dose-dependent manner. Transcript expression was reduced by a maximum of 87% (0.13±0.06 of control) at 100 nM, with an IC50 of approximately 25 nM. Doses above 100 nM did not significantly decrease message knockdown (data not shown).

Example 4

In Vivo Analysis

In vivo oligonucleotide treatment. MOE gapmer or siRNA oligonucleotides were administered in saline (0.9% NaCl) via intravenous tail vein injection at the indicated doses once per day for five days. Mice were sacrificed on day five, six hours post administration. Liver RNA was isolated as described below.

RNA isolation and expression analysis. Total RNA was extracted from mouse liver by homogenizing liver in guanidinium isothiocyanate at time of sacrifice, and isolating total RNA standard cesium chloride gradient centrifugation techniques. Gene expression was determined via real time quantitative RT-PCR on the ABI Prism 7700 system (Applied Biosystems, Foster City Calif.) as described above.

Primary hepatocyte monolayer model. Mouse primary hepatocytes plated in 6-well plates were dosed with ISIS 116847(MG-PTEN), a MOE gapmer specific for PTEN (Butler et al., Diabetes, 2002, 51, 1028-1034), at 25 and 100 nM in the presence of lipofectin PTEN mRNA expression levels fell in a dose-dependent manner. Transcript expression was reduced by a maximum of 87% (0.13±0.06 of control) at 100 nM, with an IC50 of approximately 25 nM. Doses above 100 nM did not significantly decrease message knockdown (data not shown).

Example 5

Design of Single and Double-strand Antisense Constructs

MG-PTEN is a 20-base chimeric 2'-O-methoxyethyl oligonucleotide (MOE gapmer) that has previously been demonstrated to be a potent inhibitor of mouse PTEN expression (Butler et al., Diabetes, 2002, 51, 1028-1034). siRNA analogs to the same coding region targeted by MG-PTEN were synthesized to compare the in vitro dose-response characteristics of the two classes of antisense compounds. Table 12 is a representative list of oligonucleotides used, their sequences, and specific chemical modifications.

Single-strand MOE gapmers and double-strand RNA (dsRNA) show comparable activity profiles in primary mouse hepatocytes under cationic lipid transfection conditions.

Mouse primary hepatocytes plated in 96-well plates were transfected with either: the MOE gapmer MG-PTEN, the 6-base mismatch (MG-PTEN(6MM)), the blunt ended dsRNA analog to the MOE 116847 site (si-PTEN(blunt)), the 2-nt 3'-overhang dsRNA analog with mixed backbone (si-PTEN), or the 6 base-pair 2-nt 3'-overhang dsRNA mismatch to si-PTEN with mixed backbone (si-PTEN(6MM)) in the presence of Lipofectin. Both the MOE gapmer and the dsRNA designed against the target region 116847 significantly reduced PTEN mRNA in a dose-dependent manner. The mixed backbone dsRNA containing 2-nt 3'-dTdT overhangs, si-PTEN, appeared to have a slightly lower $IC_{50}$ than the corresponding blunt-end dsRNA, si-PTEN (blunt). While, the $IC_{50}$ for the 2'-MOE MG-PTEN was significantly lower (12.5 nM), maximal mRNA reduction was achieved at 200 nM (higher dosages not shown). The lower $IC_{50}$ observed for MG-PTEN could reflect mechanistic differences in target reduction or reflect that the sequence used for comparative purposes was optimized for MOE gapmer chemistry. The PTEN mismatch control to the mixed backbone dsRNA containing 2-nt 3'-dTdT overhangs, si-PTEN(6MM), did not effect PTEN mRNA levels, suggesting that target reduction was not due to non-specific dsRNA or siRNA effects.

Uptake activity is independent of sequence. Evidence suggests that the uptake of antisense oligonucleotides is independent of oligonucleotide sequence (Leeds et al., Nucleosides Nucleotides, 1997, 16, 1689-1693; and Geary et al., J. Pharmacol. Exp., 2001, 296, 890-897). To confirm that the in vitro Lipofectin mediated dose-dependent inhibition of target observed with the MOE gapmer MG-PTEN could be reproduced with other potent antisense MOE gapmers, another potent MOE gapmer, MG-Fas, was selected for Lipofectin mediated dose-response analysis. MG-Fas targets a sequence within the translated region of the murine Fas transcript. It is a 20-base chimeric MOE gapmer that has been shown to inhibit Fas expression both in vitro and in vivo in a dose-dependent and sequence-specific manner. It has been reported that both Fas mRNA and protein levels fall as much as 90% in mice dosed with MG-Fas (Zhang et al., Nat. Biotechnol., 2000, 18, 862-867). As described for PTEN, mouse primary hepatocytes were plated in 96-well plates and transfected with either: the MOE gapmer MG-Fas; MG-Fas (6MM), a 6 base mismatch control to MG-Fas; si-Fas, a dsRNA containing an antisense strand using the anti-Fas siRNA sequence 1 from a study by Song et. al. (Nat. Med., 2003, 9, 347-351), where they reported that hydrodynamic tail vein injection of this sequence into mice reduced Fas mRNA expression in liver hepatocytes by approximately 86% of control; and si-Fas(6MM), a 6 base mismatch control dsRNA. Both MG-Fas and si-Fas reduced Fas mRNA expression in a dose-dependent manner, MG-Fas reducing Fas mRNA to 0.76±0.12 and 0.04±0.03 of control at 75 and 300 nM, respectively; and si-Fas reducing expression to 0.82±0.05 and 0.29±0.08 of control at 75 and 300 nM, respectively. Thus, the PTEN and Fas data taken together suggest that both MOE gapmers and dsRNAs inhibit gene expression in a dose-dependent manner when transfected into isolated mouse hepatocytes.

To further investigate whether chemical modifications to the MOE gapmer backbone would alter dose-response characteristics, mouse primary hepatocytes were transfected with either the MOE gapmer MG-PTEN; MG-PTEN(6MM), the 6 base mismatch control to MG-PTEN; ODN-PTEN, a first generation unmodified 20-mer phosphorothioate (PS) oligonucleotide (no MOE modifications); or ODN-PTEN(6MM), ODN-PTEN's 6 base mismatch control (Table 12). These oligodeoxynucleotides contain PS backbones, but are uniformly 2'-OH unmodified. Both the MOE gapmer and the unmodified PS oligonucleotide significantly reduced PTEN mRNA in a dose-sensitive manner. The slightly greater target knockdown seen with the MG-PTEN supports previous observations that MOE modified PS oligonucleotides have slightly increased binding affinity for their complementary RNAs (Crooke et al., Biochem. J., 1995, 312(Pt 2), 599-608). MOE gapmer increased nuclease resistance may also be increasing MG-PTENs efficacy in this assay by increasing intracellular concentrations relative to ODN-PTEN over time.

Single-strand MOE gapmers and PS oligonucleotides show different activity profiles than double-strand RNA (dsRNA) in primary mouse hepatocytes in free-uptake conditions. Graham et al. (J. Pharmacol. Exp. Therap., 1998, 286, 447-458) has previously demonstrated both free uptake and activity of MOE gapmers incubated with primary hepatocytes without the use of cationic lipids similar to that seen in vivo.

To investigate the dose-response sensitivity of the MOE gapmers, experiments were conducted in mouse primary hepatocytes plated in 6-well plates with both MG-PTEN and MG-Fas at concentrations ranging from 75 to 10000 nM (see above procedures). The expression levels of both targeted PTEN and Fas mRNA subsequently fell in a dose-dependent manner. Maximal inhibition (~90%) of both PTEN and Fas mRNA levels was achieved at 3000 nM, with an IC50 of approximately 350 nM for PTEN and 750 nM for Fas. Higher concentrations of either MG-PTEN or MG-Fas did not significantly reduce transcript levels. Six base mismatches to both MG-PTEN and MG-Fas, MG-PTEN(6MM) and MG-Fas(6MM), did not reduce transcript levels; arguing against ASO dose related mRNA toxicity (data not shown). PTEN and Fas transcript levels were normalized with RiboGreen. However, the dose-response trends observed were independent of the normalization technique, as normalization using either RiboGreen or GAPDH transcript levels yielded similar results (GAPDH data not shown).

To further confirm that the in vitro dose-dependent inhibition of target observed with both MG-PTEN and MG-Fas could be reproduced with other potent antisense MOE gapmers, two additional potent MOE gapmers, MG-ApoB and MG-MTTP were selected for free uptake dose-response analysis (see Table 12). MG-ApoB is a potent inhibitor of the mouse apolipoprotein B (ApoB) (unpublished data). MG-MTTP targets mouse microsomal triglyceride transfer protein (MTTP) (unpublished data). All MOE gapmers tested displayed similar dose-response dynamics (data not shown), suggesting that the mechanism of MOE gapmer uptake and subsequent RNA inhibition is highly conserved.

To determine whether dsRNA might also demonstrate both free uptake and activity without the use of cationic lipids, mouse primary hepatocytes were dosed with either si-PTEN (blunt), si-PTEN, si-PTEN(6MM), the MG-PTEN, MG-Fas, MG-Fas(6MM), si-Fas, or si-Fas(6MM); at concentrations ranging from 375 to 1500 nM. The siRNA constructs are capable of specific target reduction in the presence of the cationic lipid Lipofectin. However, whereas the MOE modified single-strand DNAs MG-PTEN and MG-Fas show robust target reduction even at the lowest concentrations (375 nM), no target reduction was observed with dsRNA under these conditions.

Given the lack of activity observed for dsRNA in free uptake experiments under the expressed conditions, it was of interest to determine whether MOE modifications were aiding free uptake of single-strand DNA. Again, the unmodified homologs to MG-PTEN and the 6 base mismatch MG-PTEN (6MM), ODN-PTEN and ODN-PTEN(6MM) were used. These first generation, unmodified molecules demonstrate a dose responsive, specific target reduction. Again, the MOE modified gapmer MG-PTEN demonstrated much greater message knockout, suggesting that the MOE modification may assist and improve the oligonucleotide delivery in the absence of transfection reagents. Again, the half-lives of unmodified first generation oligodeoxynucleotides are much shorter, which may in part explain the reduced activity observed with these molecules.

Capillary gel electrophoresis (CGE) was used to look at the stability of the duplex siRNA constructs in the treatment media (see above for media description) at different time points. If the duplex is still intact after 16 hrs, which is the duration of our treatments, the construct is considered valid for the in vitro assay proposed herein, and tested for uptake and/or activity.

Example 6

In Vivo Target Inhibition—MOE Gapmers Versus dsRNAs

Given the observed robust target inhibition with both single-stranded MOE gapmers, unmodified PS oligonucleotides and dsRNA when using Lipofectin as a transfection agent, but no observation of dsRNA activity when a transfection reagent was not used under the conditions described above, coupled with reports that dsRNA when administered in vivo via high pressure tail injections knock down target (McCafferey et al., Nature, 2002, 418, 38-39; Lewis et al., Nat. Genet., 2002, 32, 107-108; and Song et al., Nat. Med., 2003, 3, 347-351), it was of interest to compare MOE gapmer and dsRNA activity in vivo using conventional intravenous injections. MG-PTEN, MG-PTEN(6MM), si-PTEN and si-PTEN(6MM) were administered daily for 5 days at concentrations of either 2.5 mg/kg or 25 mg/kg. Only MG-PTEN reduced PTEN mRNA levels in liver. Further, in a separate study, animals were dosed daily for five days with si-PTEN (blunt) to concentrations as high as 50 mg/kg. Again, only MG-PTEN reduced PTEN mRNA levels in liver. No effect was observed for intraperitoneal injected siPTEN(blunt) under the conditions described above. High-pressure delivery systems may mimic in vitro transfection mediated oligonucleotide delivery by altering cell membrane permeability; however, we are unaware of any studies demonstrating mRNA knockdown with dsRNA using conventional delivery systems.

The results suggest that the in vitro primary hepatocyte model correlates both with single-strand DNA oligonucleotide (both MOE gapmer and PS oligonucleotides) and dsRNA in vivo activity. Specifically, whereas single-strand oligonucleotides effectively decrease target mRNA expression both in vitro and in vivo without the aid of a delivery system, dsRNA does not decrease target mRNA expression in hepatocytes in vitro without the aid of transfection reagents under the conditions described above or in vivo when delivered by conventional dosing methods.

Example 7

Sequential Delivery dsRNA is now shown to decrease target mRNA expression in hepatocytes in vitro without the aid of transfection reagents. The following PTEN oligomeric compounds were used in a free uptake assay in primary mouse hepatocytes, as described above: Compound 303912 antisense (TTTGTCTCTGGTCCTTACTT; SEQ ID NO:34; PS backbone, RNA sugar); Compound 316449 antisense (TTTGTCTCTGGTCCTTACTT; SEQ ID NO: 34; PS backbone, 3' 3× Ome sugar); Compound 347849 antisense (TTTGTCTCTGGTCCTTACTTT; SEQ ID NO:36; PO backbone, RNA sugar); Compound 341315 sense (AAGTAAGGACCAGAGACAAA; SEQ ID NO:37; PS backbone, full Ome sugar); and Compound 308746 sense (AAGTAAGGACCAGAGACAAA; SEQ ID NO: 37; PO backbone, RNA sugar). The mRNA target levels were normalized to total RNA (RiboGreen). The results are expressed as % UTC and are reported in Table 13. The following Table 2 shows the delivery protocol and results of treatment of each group.

Oligomeric siRNA compound combinations 303912:341315 and 316449:341315 show activity in this free uptake system. Sequentially treating with these antisense sequences first followed by the sense strand do not show appreciable target reduction. In contrast, sequentially treating with the sense strand first followed by the antisense strand shows good activity except at the one hour strand switching. In addition, sequential treatment with 303912 is as potent as the corresponding siRNA. Further, sequential treatment with 316449 is more potent than the corresponding siRNA. Even further, chemical modification of the terminal three 3' nucleotides to comprise 2'-Ome sugar residues, as in Compound 316449, is suitable.

A dose-response study was also performed in the primary hepatocyte free uptake assay with the following oligomeric compounds: Compound 303912 antisense (TTTGTCTCTGGTCCTTACTT; SEQ ID NO:34; PS backbone, RNA sugar); Compound 335449 antisense (TTTGTCTCTGGTCCTTACTT; SEQ ID NO: 34; PO backbone, RNA sugar); Compound 341315 sense (AAGTAAGGACCAGAGACAAA; SEQ ID NO:37; PS backbone, full 2'-Ome sugar); Compound 330696 sense (AAGTAAGGACCAGAGACAAA; SEQ ID NO: 37; PO backbone, full 2'-Ome sugar); and Compound 344178 sense (AAGTAAGGACCAGAGACAAA; SEQ ID NO: 37; PS backbone, RNA sugar). Results are shown in FIG. 1.

Example 8

Sequential Delivery-Effects of Modifications

The following PTEN oligomeric compounds were used in a free uptake assay in primary mouse hepatocytes, as described above: Compound 303912 antisense (TTTGTCTCTGGTCCTTACTT; SEQ ID NO:34; PS backbone, RNA sugar, 5' phosphate); Compound 335449 antisense (TTTGTCTCTGGTCCTTACTT; SEQ ID NO: 34; PO backbone, RNA sugar, 5' phosphate); Compound 317502 antisense (TTTGTCTCTGGTCCTTACTTT; SEQ ID NO: 36; PS backbone, RNA sugar with 2' Fluoro modifications at the bolded positions, 5' phosphate); Compound 354626 antisense (TTTGTCTCTGGTCCTTACTT; SEQ ID NO: 34; PS backbone, RNA sugar, 5' hydroxyl); Compound 116847 antisense (TTTGTCTCTGGTCCTTACTT; SEQ ID NO: 34; PS backbone, MOE/DNA sugar having 2'MOE groups at positions 1-5 and 16-20); Compound 344178 sense (AAGTAAG-GACCAGAGACAAA; SEQ ID NO: 37; PS backbone, RNA sugar); Compound 341315 sense (AAGTAAGGACCA-GAGACAAA; SEQ ID NO:37; PS backbone, full 2'O-methyl sugar); Compound 354622 sense (AAGCAACGAGAAGC-GATAAA; SEQ ID NO: 37; PS backbone, full 2'O-methyl sugar; 6base mismatch to Compound 341315) and Compound 330696 sense (AAGTAAGGACCAGAGACAAA; SEQ ID NO: 37; PO backbone, full 2'-O-methyl sugar). The mRNA target levels were normalized to total RNA (RiboGreen). The results are expressed as % UTC and are reported in Table 14. The following Table 3 shows the delivery protocol and results of treatment of each group.

Oligomeric siRNA compound combinations 303912:344178 and 354626:344178 show activity in this free uptake system. Sequentially treating with the sense strand of these duplexes first followed by the antisense strand shows good activity at every time point tested. In addition, sequential treatment with 303912 or 354626 at the one hour time point is as potent as the corresponding siRNA (compare sequential treatments B and N with siRNA treatments Y and Z). Even further, chemical modification with a fluoro group at select 2' positions in the antisense strand was also found to effectively reduce target RNA levels.

Example 9

Sequential Delivery-Comparison of Backbone Chemistry in 2'OMe Background Construct The following PTEN oligomeric compounds were used in a free uptake assay in primary mouse hepatocytes, as described above: Compound 303912 antisense (TTTGTCTCTGGTCCTTACTT; SEQ ID NO:34; PS backbone, RNA sugar, 5' phosphate); Compound 335449 antisense (TTTGTCTCTGGTCCTTACTT; SEQ ID NO: 34; PO backbone, RNA sugar, 5' phosphate); Compound 317502 antisense (TTTGTCTCTGGTCCTTACTTT; SEQ ID NO: 36; PS backbone, RNA sugar with 2' Fluoro modifications at the bolded positions, 5' phosphate); Compound 354626 antisense (TTTGTCTCTGGTCCTTACTT; SEQ ID NO: 34; PS backbone, RNA sugar, 5' hydroxyl); Compound 116847 antisense (TTTGTCTCTGGTCCTTACTT; SEQ ID NO: 34; PS backbone, MOE/DNA sugar having 2'MOE groups at positions 1-5 and 16-20); Compound 341315 sense (AAGTAAG-GACCAGAGACAAA; SEQ ID NO:37; PS backbone, full 2'O-methyl sugar); and Compound 330696 sense (AAG-TAAGGACCAGAGACAAA; SEQ ID NO: 37; PO backbone, full 2'-O-methyl sugar). The mRNA target levels were normalized to total RNA (RiboGreen). The results are expressed as % UTC and are reported in Table 15. The following Table 15 shows the delivery protocol and results of treatment of each group. Entry of "ND" in the Table indicates at least one reagent or construct was limiting and no data were gathered for this group.

Oligomeric siRNA compound combinations 354626:341315 show activity in this free uptake system. Sequentially treating with the sense strand of these duplexes first followed by the antisense strand shows good activity at every time point tested.

Even further, sequentially treating with compound 341315, a sense strand having a phosphorothioate backbone and which is fully modified with OMe at the 2' positions, followed by either the antisense strand of compound 303912 or 354626 (differing in the 5' terminal moiety) show equally potent results, suggesting that the 5' terminus is not the determinant factor in target reduction for these constructs.

Example 10

Activity For Backbone Chemistry

PTEN constructs and results are shown in Table 16. As shown in Table 16, 2' MOE in both strands improves activity.

PTEN constructs and results are shown in Table 17. As shown in Table 17, MOE gapmer sense strands enhance the potency of siRNA duplexes.

Figure 2:
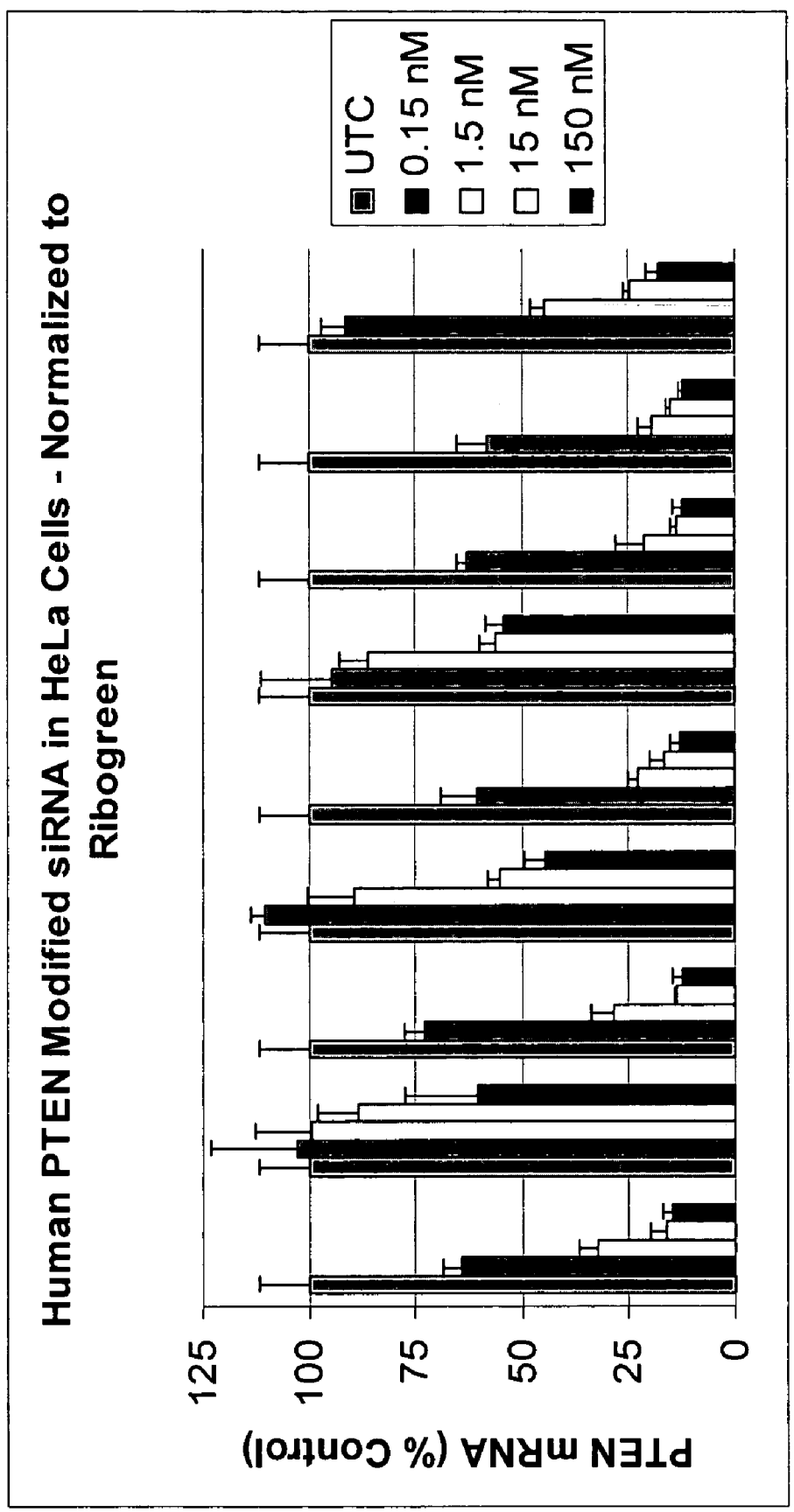
FIG. 2 shows 2'-OMe and 2'-MOE modification resulted in highly potent siRNA.

PTEN 2'-OMe and 2'-MOE modified constructs and results are shown in Table 18 and FIG. 2. As shown in Table 18 and FIG. 2, 2'-OMe and 2'-MOE modification resulted in highly potent siRNA. A similar trend was observed for other targets.

Figure 3:
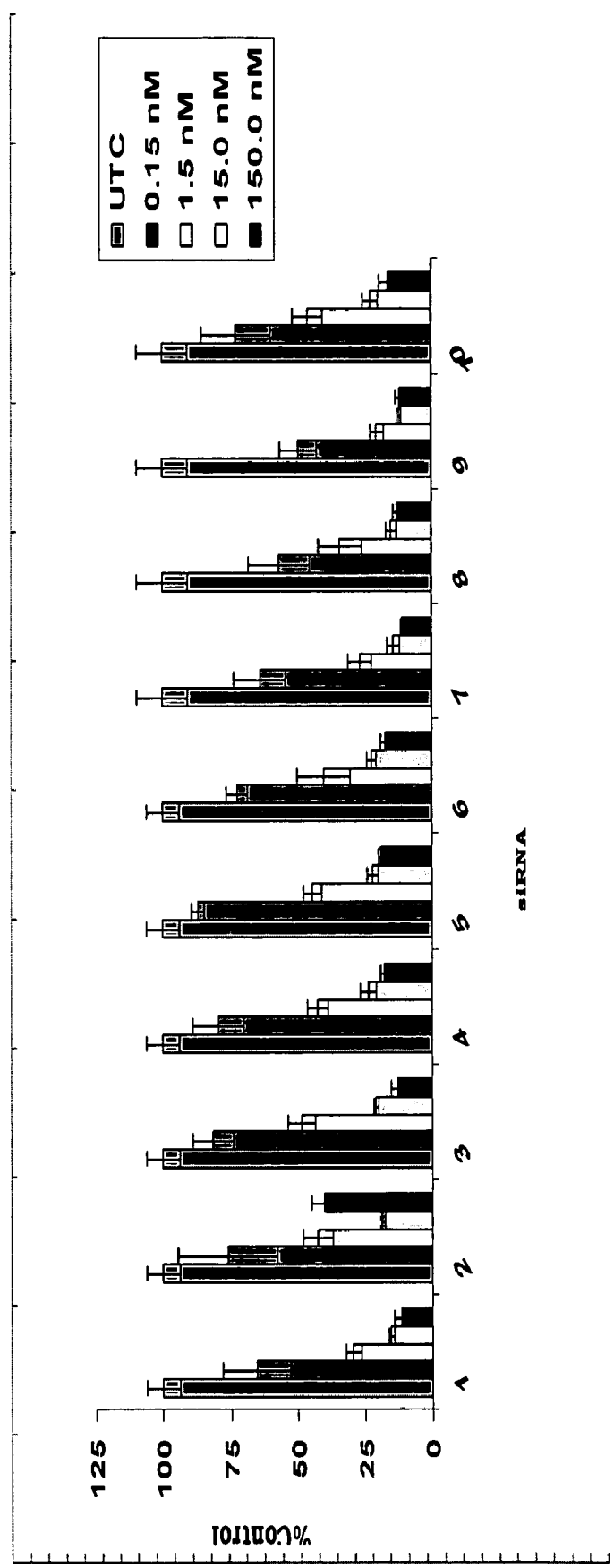
FIG. 3 shows 4'-thio modification resulted in increased stability and activity to RNA on sense and antisense strand.

PTEN 4'-Thio modified constructs and results are shown in Table 19 and FIG. 3. As shown in Table 19 and FIG. 3, 4'-Thio modification resulted in increased stability and activity to RNA on sense and antisense strand.

Example 11

In Vivo Activity

Figure 4:
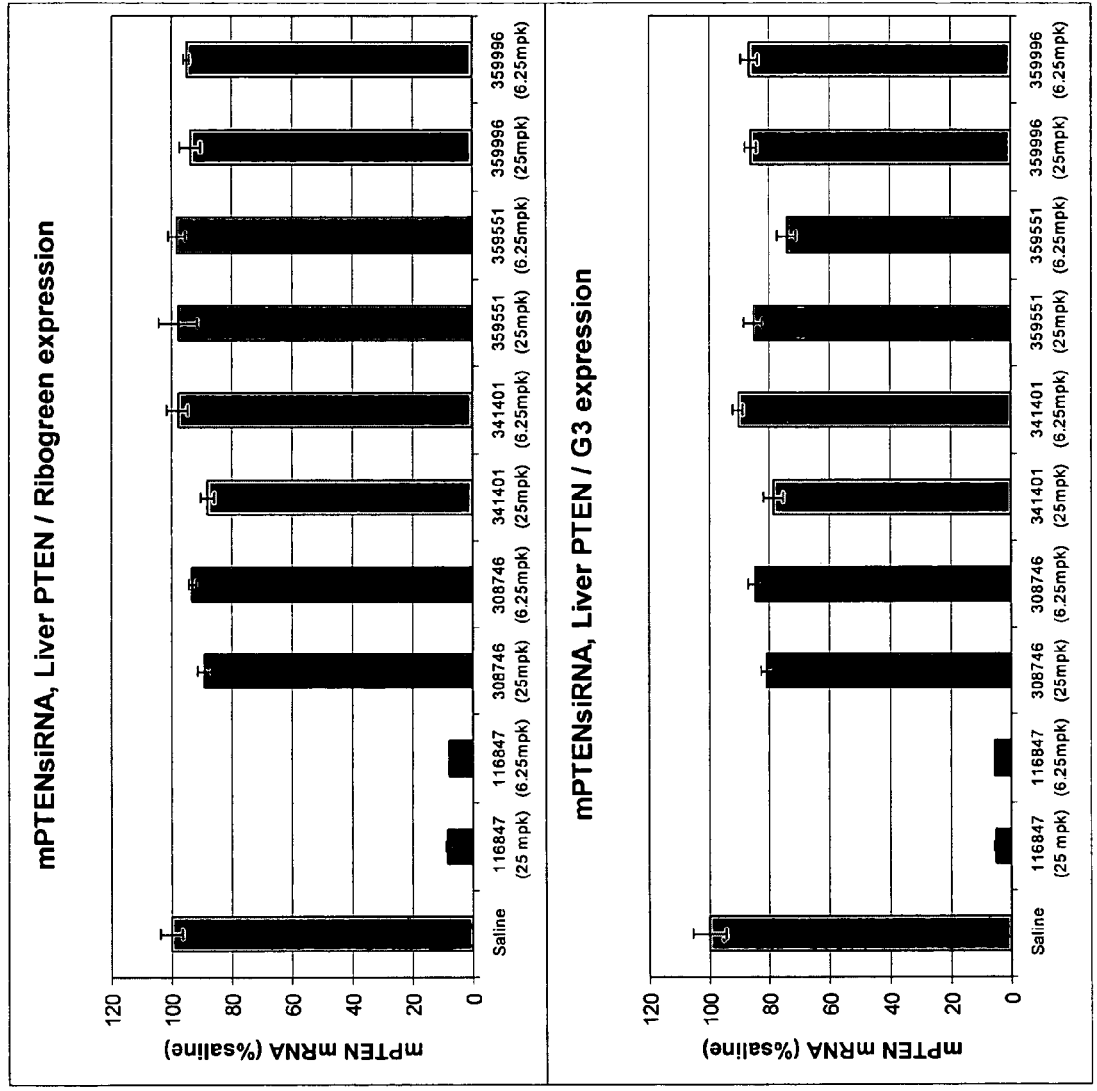
FIG. 4 shows levels of PTEN mRNA upon treatment with MOE gapmer, 4'-thio gapmer, unmodified, alternating PO/PS, and alternating OMe/F siRNA constructs.
Figure 5:
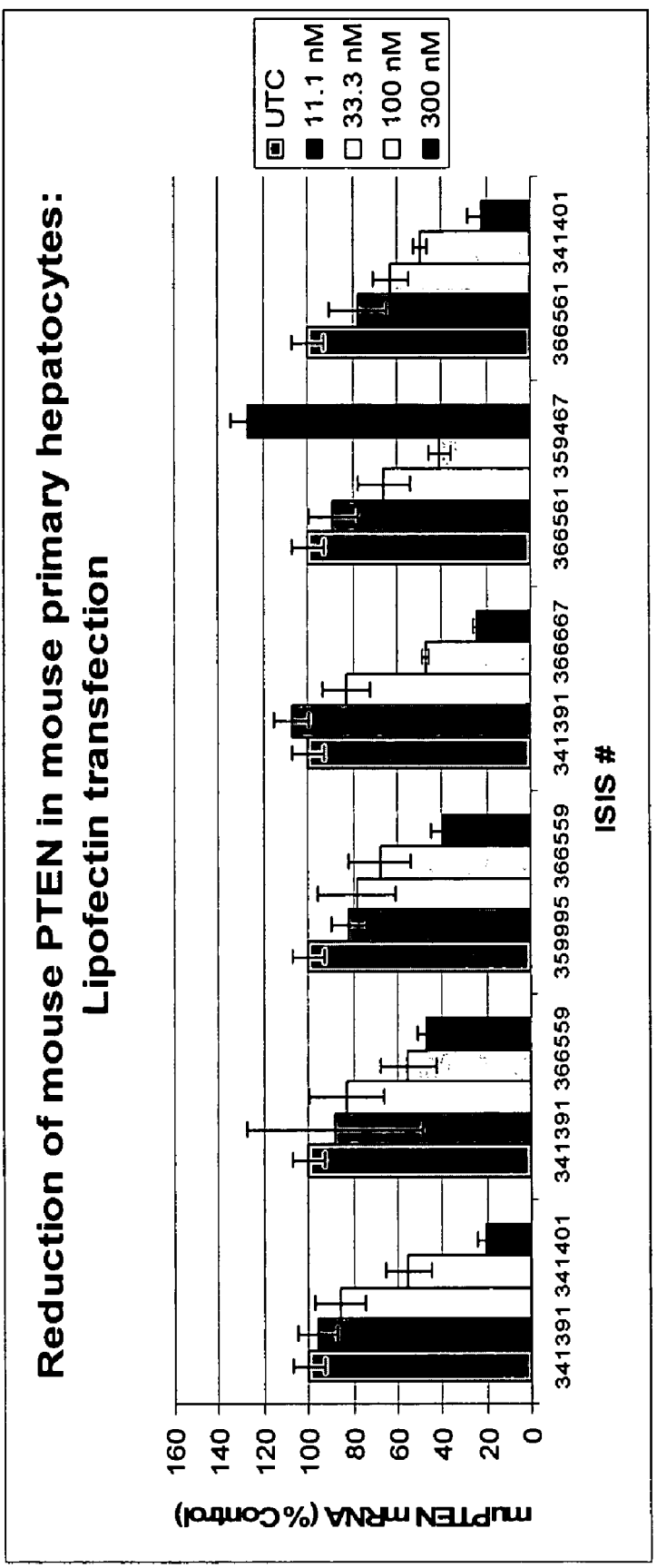
FIG. 5 shows reduction of mouse PTEN mRNA in mouse primary hepatocyts via lipofectin transfection using particular constructs.
Figure 6:
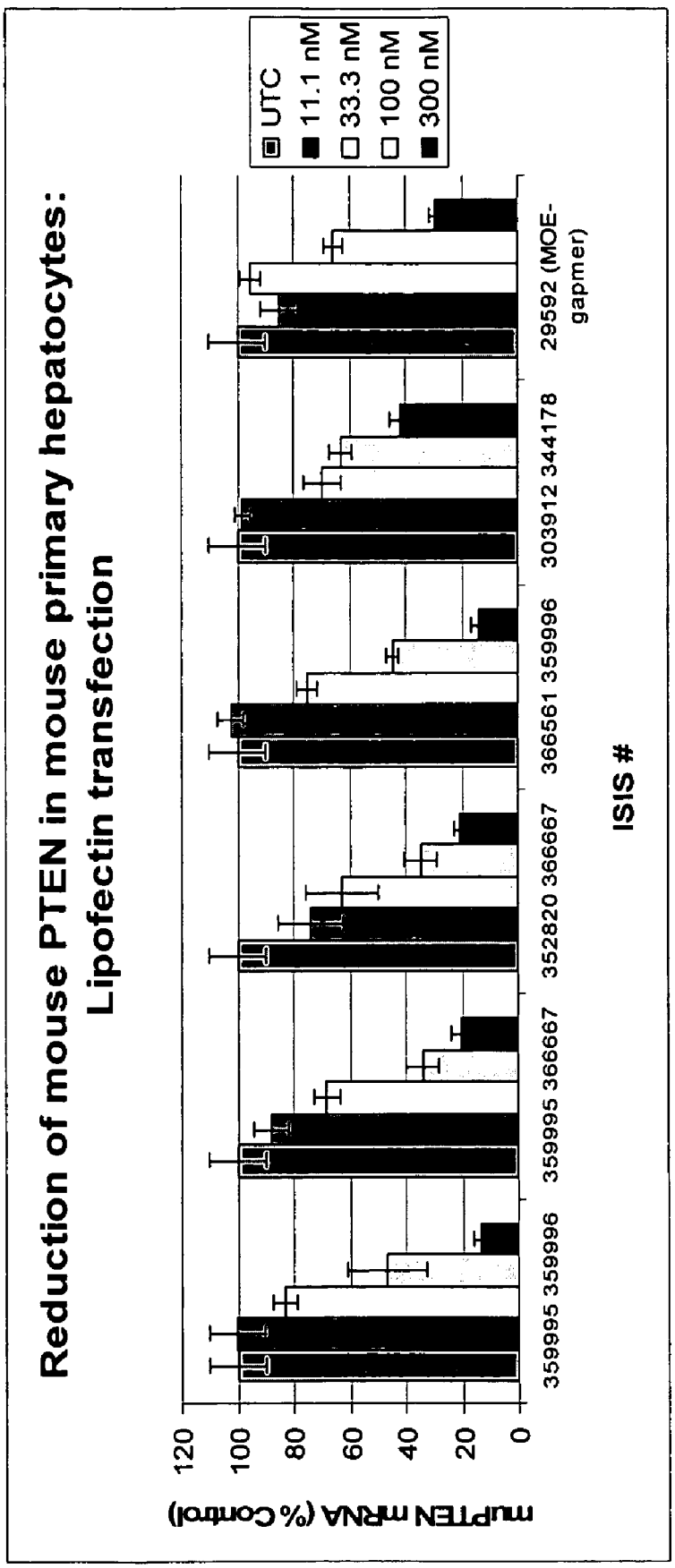
FIG. 6 shows reduction of mouse PTEN mRNA in mouse primary hepatocyts via lipofectin transfection using particular constructs.
Figure 7:
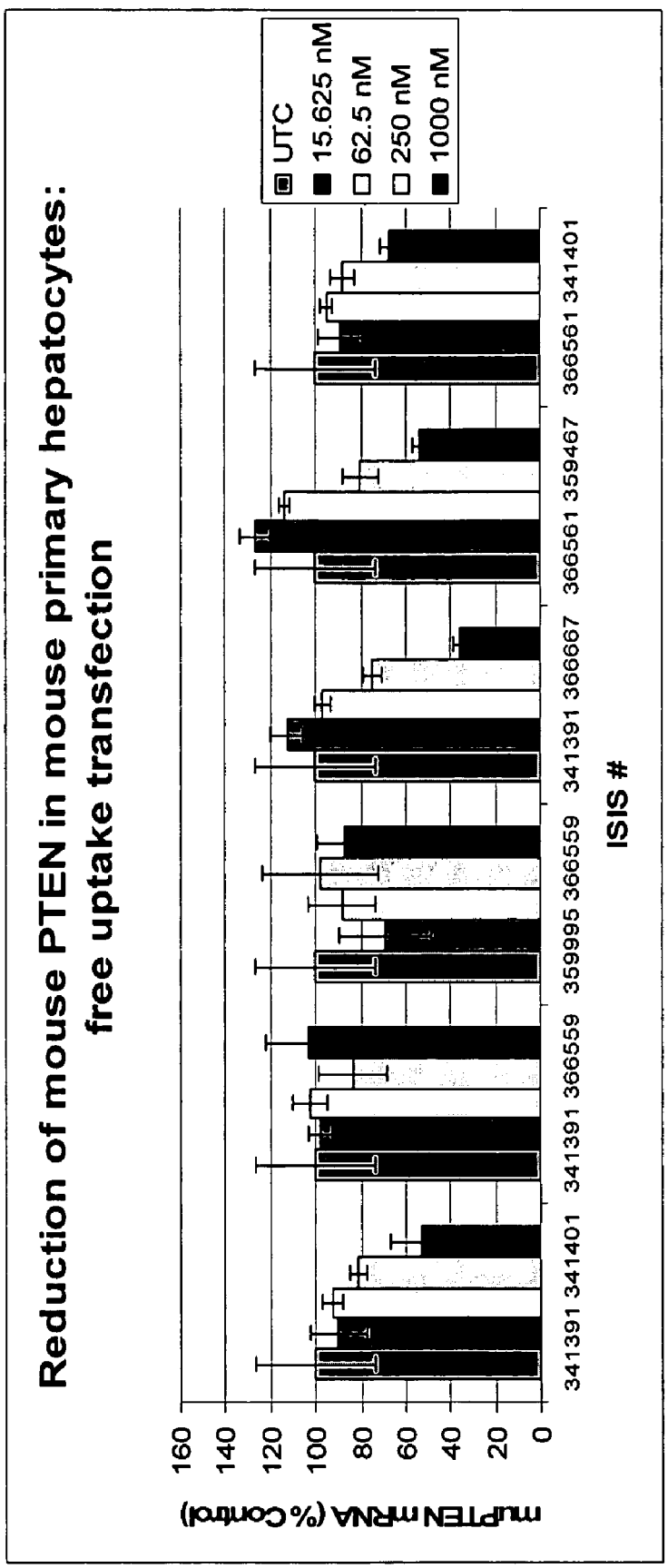
FIG. 7 shows reduction of mouse PTEN mRNA in mouse primary hepatocyts via free uptake transfection using particular constructs.
Figure 8:
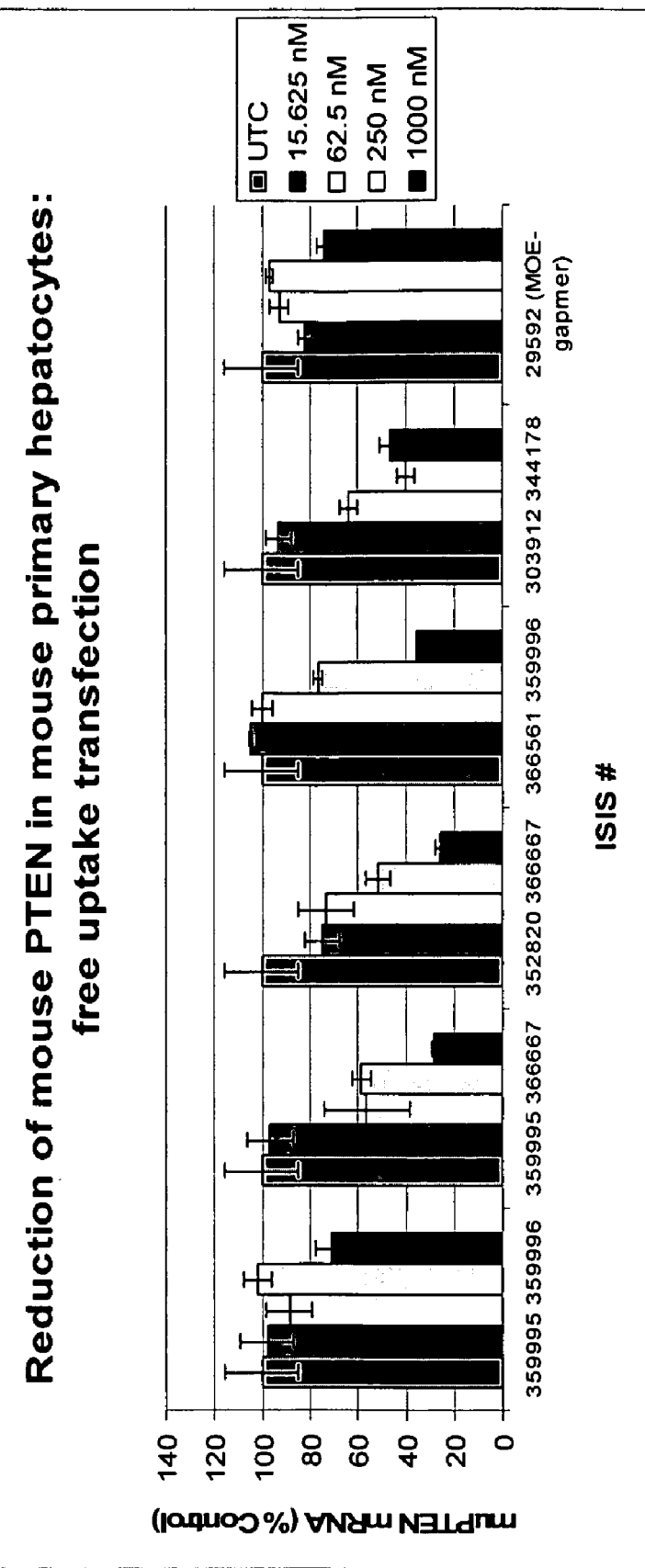
FIG. 8 shows reduction of mouse PTEN mRNA in mouse primary hepatocyts via free uptake transfection using particular constructs.

4 Balb/c per group were dosed at 25 and 6.25 mg/kg twice daily via I.P., and were sacrificed after the 9$^{th}$ dose. In some embodiments, PTEN mRNA levels and glucose were measured. In some embodiments, AST, ALT, triglycerides, and organ weight were measured. In some embodiments, liver, kidney, and urine wew collected for PK. Results are shown in Table 20 and FIG. 4. Referring to FIG. 4, after the saline group is: MOE gapmer, 4'-thio gapmer, unmodified, alternating PO/PS, and alternating OMe/F. There was no observed change in AST or ALT levels in any siRNA group. There was also no observed change in liver, spleen, kidney, or WAT weights in any group. There was also no observed change in glucose, cholesterol, or triglycerides.

A sandwich ELISA assay was developed to measure the levels of sense and antisense strands in tissue and urine. Less than 0.06 nM concentration of either sense or antisense RNA strand was detected in the liver. See Table 21.

Example 12

In Vitro Analysis of Cholesterol Conjugates

An in vitro analysis of cholesterol conjugates was also carried out, the results of which are set forth in Tables 22-25 and FIGS. 5-8. Sense strand 3'-cholesterol conjugated siRNA showed comparable activity to 5'-conjugated constructs in lipofectine mediated in vitro assays. 5'-cholesterol conjugated siRNA showed better activity in mouse primary hepatocytes in free uptake assays. Conjugtaes with OMe/F alternating chemistries resulted in improved potency.

Example 13

General Target X Chemistries and Activity Thereof

The compounds listed in Table 26 were administered IV at 25 mg/kg, BIDx2 (8 hours apart on day 1 and 4 hours apart on day 2. Target X siRNA 1 is antisense and sense blunted siRNA. Target X siRNA 2 is antisense (3 bases 4'-thio at 5' and 3' ends) and sense (blunted) siRNA. Target X siRNA 3 is antisense (2'-OMe internal and 3') and sense (alternating 2'-MOE). Target X siRNA 4 is antisense and sense alternating 2'-OMe and 2'-F. Tissues (liver, kidney, and serum) were collected 2 hours after the last dose. Normalized to Target Y, the Target X siRNA 1 demonstrated no inhibition (results not shown). Normalized to Target Y, Target X siRNA 2 demonstrated 48.37±10.52% inhibition (data not shown). Normalized to Target Y, Target X siRNA 2 demonstrated 44.39±12.47% inhibition (data not shown). Normalized to Target Y, Target X siRNA 4 demonstrated 59.62±10.22% inhibition (data not shown). In sum, 1) blunted naked siRNA duplex 1 did not show protein reduction; 2) inhibition of target X expression was observed with siRNAs modified with 4'-thio, 2'-O-Me/2'-MOE, and with alternating 2'-O-Me/2'-F modification; and 3) alternating 2'-O-Me/2'-F modifications of both sense and antisense strands of Target X siRNA appeared to be more potent than other modifations.

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

TABLE 1

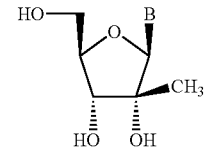

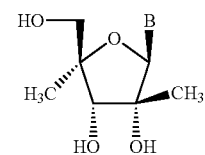

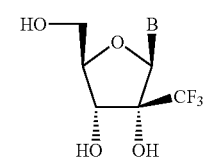

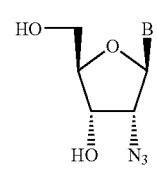

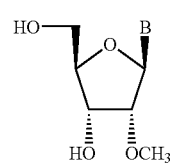

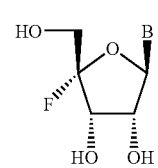

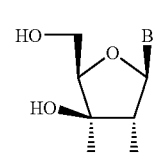

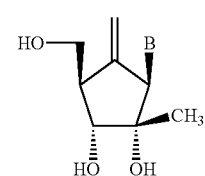

TABLE 1-continued

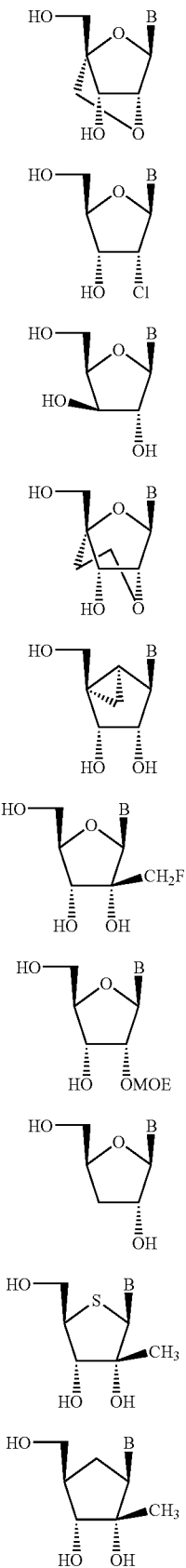

TABLE 1-continued

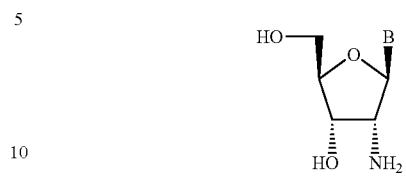

TABLE 2

Modified DNA strand having 2'-substituent groups that gave an overall increase in Tm against an RNA complement:

Positive ∈Tm/mod

| 2'-substituents | 2'-OH |
|---|---|
| | 2'-O—$C_1$-$C_4$ alkyl |
| | 2'-O—$(CH_2)_2CH_3$ |
| | 2'-O—$CH_2CH$=$CH_2$ |
| | 2'-F |
| | 2'-O—$(CH_2)_2$—O—$CH_3$ |
| | 2'-(O—$(CH_2)_2)_2$—O—$CH_3$ |
| | 2'-(O—$(CH_2)_2)_3$—O—$CH_3$ |
| | 2'-(O—$(CH_2)_2)_4$—O—$CH_3$ |
| | 2'-(O—$(CH_2)_2)_3$—O—$(CH_2)_8CH_3$ |
| | 2'-O—$(CH_2)_2CF_3$ |
| | 2'-O—$(CH_2)_2OH$ |
| | 2'-O—$(CH_2)_2F$ |
| | 2'-O—$CH_2CH(CH_3)F$ |
| | 2'-O—$CH_2CH(CH_2OH)OH$ |
| | 2'-O—$CH_2CH(CH_2OCH_3)OCH_3$ |
| | 2'-O—$CH_2CH(CH_3)OCH_3$ |
| | 2'-O—$CH_2$—$C_{14}H_7O_2$(—$C_{14}H_7O_2$ = Anthraquinone) |
| | 2'-O—$(CH_2)_3$—$NH_2$* |
| | 2'-O—$(CH_2)_4$—$NH_2$* |

These modifications can increase the Tm of oligonucleotides but can also decrease the Tm depending on positioning and number (motiff dependant).

TABLE 3

Modified DNA strand having modified sugar ring (see structure x) that gave an overall increase in Tm against an RNA complement:

Positive ∈Tm/mod

| Q | —S— |
|---|---|
| | —$CH_2$— |

Note:
In general ring oxygen substitution with sulfur or methylene had only a minor effect on Tm for the specific motiffs studied. Substitution at the 2'-position with groups shown to stabilize the duplex were destabilizing when $CH_2$ replaced the ring O. This is thought to be due to the necessary gauche interaction between the ring O with particular 2'-substituents (for example —O—$CH_3$ and —(O—$CH_2CH_2)_3$—O—$CH_3$.

TABLE 4

Modified DNA strand having modified sugar ring that give an overall increase in Tm against an RNA complement:

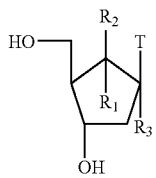

Positive εTm/mod

| —C(H)R$_1$ effects | OH |
| --- | --- |
| (R$_2$, R$_3$ both = H) | CH$_3$* |
|  | CH$_2$OH* |
|  | OCH$_3$* |

These modifications can increase the Tm of oligonucleotides but can also decrease the Tm depending on positioning and number (motiff dependant).

TABLE 5

Modified DNA strand having bicyclic substitute sugar modifications that give an overall increase in Tm against an RNA complement:

| Formula | Positive εTm/mod |
| --- | --- |
| I | + |
| II | + |

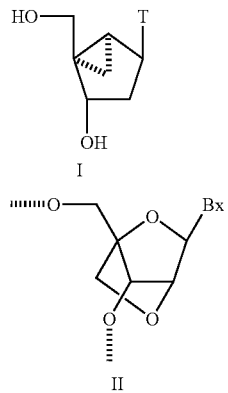

TABLE 6

Modified DNA strand having modified heterocyclic base moieties that give an overall increase in Tm against an RNA complement:

| Modification/Formula | Positive εTm/mod |
| --- | --- |
| Heterocyclic base modifications | 2-thioT |
|  | 2'-O-methylpseudoU |
|  | 7-halo-7-deaza purines |
|  | 7-propyne-7-deaza purines |
|  | 2-aminoA(2,6-diaminopurine) |

TABLE 6-continued

| (R$_2$, R$_3$ = H), R$_1$ = | Br |
| --- | --- |
|  | C/C—CH$_3$ |
|  | (CH$_2$)$_3$NH$_2$ |
|  | CH$_3$ |
| Motiffs-disubstitution | |
| R$_1$ = C/C—CH$_3$, R$_2$ = H, R$_3$ = | F |
| R$_1$ = C/C—CH$_3$, R$_2$ = H | R$_3$ = O—(CH$_2$)$_2$—O—CH$_3$ |
| R$_1$ = O—CH$_3$, R$_2$ = H, | R$_3$ = O—(CH$_2$)$_2$—O—CH$_3$* |

This modification can increase the Tm of oligonucleotides but can also decrease the Tm depending on positioning and number (motiff dependant).

TABLE 7

DNA strand having at least one modified phosphorus containing internucleoside linkage and the effect on the Tm against an RNA complement:

| ∈Tm/mod+ | ∈Tm/mod− |
| --- | --- |
| phosphoramidate (the 3'-bridging atom replaced with an N(H)R group, stabilization effect enhanced when also have 2'-F) | phosphorothioate[1] phosphoramidate[1] methyl phosphonates[1] |

([1] one of the non-bridging oxygen atoms replaced with S, N(H)R or —CH$_3$)

TABLE 8

DNA strand having at least one non-phosphorus containing internucleoside linkage and the effect on the Tm against an RNA complement:
Positive ∈Tm/mod —CH$_2$C(=O)NHCH$_2$—*
—CH$_2$C(=O)N(CH$_3$)CH$_2$—*
—CH$_2$C(=O)N(CH$_2$CH$_2$CH$_3$)CH$_2$—*
—CH$_2$C(=O)N(H)CH$_2$—(motiff with 5'-propyne on T's)
—CH$_2$N(H)C(=O)CH$_2$—*
—CH$_2$N(CH$_3$)OCH$_2$—*
—CH$_2$N(CH$_3$)N(CH$_3$)CH$_2$—*

This modification can increase the Tm of oligonucleotides but can also decrease the Tm depending on positioning and number (motiff dependant).
Notes:
In general carbon chain internucleotide linkages were destabilizing to duplex formation. This destabilization was not as severe when double and tripple bonds were utilized. The use of glycol and flexible ether linkages were also destabilizing.

TABLE 9

Relative energies* of the C3'-endo and C2'-endo conformations of representative nucleosides.

| | HF/6-31G | MP2/6-31-G | CONTINUUM | AMBER | MODEL |
| --- | --- | --- | --- | --- | --- |
| dG | 0.60 | 0.56 | 0.88 | 0.65 | |
| rG | −0.65 | −1.41 | −0.28 | −2.09 | |
| 2'-O-MeG | −0.89 | −1.79 | −0.36 | −0.86 | |
| 2'-S-MeG | 2.55 | 1.41 | 3.16 | 2.43 | |

*energies are in kcal/mol relative to the C2'-endo conformation

TABLE 10

Average helical parameters derived from the last 500 ps of simulation time.
(canonical A-and B-form values are given for comparison)

| Helicoidal Parameter | B-DNA (x-ray) | B-DNA (fibre) | A-DNA (fibre) | DNA:RNA | OMe_DNA:RNA | SMe_DNA:RNA |
|---|---|---|---|---|---|---|
| X-disp | 1.2 | 0.0 | −5.3 | −4.5 | −5.4 | −3.5 |
| Inclination | −2.3 | 1.5 | 20.7 | 11.6 | 15.1 | 0.7 |
| Propeller | −16.4 | −13.3 | −7.5 | −12.7 | −15.8 | −10.3 |

TABLE 11

Minor groove widths averaged over the last 500 ps of simulation time

| Phosphate Distance | DNA:RNA | OMe_DNA:RNA | Sme_DNA:RNA | DNA:RNA (B-form) | RNA:RNA (A-form) |
|---|---|---|---|---|---|
| P5-P20 | 15.27 | 16.82 | 13.73 | 14.19 | 17.32 |
| P6-P19 | 15.52 | 16.79 | 15.73 | 12.66 | 17.12 |
| P7-P18 | 15.19 | 16.40 | 14.08 | 11.10 | 16.60 |
| P8-P17 | 15.07 | 16.12 | 14.00 | 10.98 | 16.14 |
| P9-P16 | 15.29 | 16.25 | 14.98 | 11.65 | 16.93 |
| P10-P15 | 15.37 | 16.57 | 13.92 | 14.05 | 17.69 |

TABLE 12

| | Isis No. | Target | Strand | Sequence (5' to 3') | SEQ ID NO: | Composition |
|---|---|---|---|---|---|---|
| ASOs | | | | | | |
| | 160847 | PTEN | as | CTGCTAGCCTCTGGATTTGA | 16 | 2'-deoxy P=S; 5-MeC |
| ODN-PTEN (6 MM) | 160848 | PTEN | as (6 MM) | CTTCTGGCATCCGGTTTAGA | 17 | 2'-deoxy P=S; 5-MeC |
| MG-PTEN | 116847 | PTEN | as | CTGCTAGCCTCTGGATTTGA | 16 | 5_10_5 2'MOE Gapmer; 5-MeC |
| MG-PTEN (6 MM) | 116848 | PTEN | as (6 MM) | CTTCTGGCATCCGGTTTAGA | 17 | 5_10_5 2'MOE Gapmer; 5-MeC |
| MG-Fas | 22023 | Fas | as | TCCAGCACTTTCTTTTCCGG | 20 | 5_10_5 2'MOE Gapmer; 5-MeC |
| MG-Fas (6 MM) | 29836 | Fas | as (6 MM) | TCCATCTCCTTTTATGCCGG | 21 | 5_10_5 2'MOE Gapmer; 5-MeC |
| MG-MTTP | 144477 | MTTP | as | CCCAGCACCTGGTTTGCCGT | 22 | 5_10_5 2'MOE Gapmer; 5-MeC |
| MG-ApoB | 147764 | Apo B | as | GTCCCTGAAGATGTCAATGC | 23 | 5_10_5 2'MOE Gapmer; 5-MeC |
| siRNAs† | | | | | | |
| si-PTEN | 263186 | PTEN | as | CU*GC*UA*GC*CU*CU*GG*AU*UU*GdT*dT | 24 | alt *P=S, P=O linkage; 3'-dTdT overhang |
| | 263187 | PTEN | s | CA*AA*UC*CA*GA*GG*CU*AG*CA*GdT*dT | 25 | alt *P=S, P=O linkage; 3'-dTdT overhang |
| si-PTEN (6 MM) | 263188 | PTEN | as (6 MM) | CU*UC*UG*GC*AU*CC*GG*UU*UA*GdT*dT | 26 | alt *P=S, P=O linkage; 3'-dTdT overhang |
| | 263189 | PTEN | s (6 MM) | CU*AA*AC*CG*GA*UG*CC*AG*AA*GdT*dT | 27 | alt *P=S, P=O linkage; 3'-dTdT overhang |

TABLE 12-continued

| | Isis No. | Target | Strand | Sequence (5' to 3') | SEQ ID NO: | Composition |
|---|---|---|---|---|---|---|
| si-PTEN (blunt) | 278626 | PTEN | as | CUGCUAGCCUCUGGAUUUGAC | 28 | unmodified RNA |
| | 278627 | PTEN | s | GUCAAAUCCAGAGGCUAGCAG | 29 | unmodified RNA |
| si-Fas‡ | ------ | Fas | as | 5'-P GUCUGGUUUGCACUUGCAC dTdT | 30 | unmodified RNA; 5'-Phosphate, 3'-dTdT overhang |
| | ------ | Fas | s | 5'-P GUGCAAGUGCAAACCAGAC dTdT | 31 | unmodified RNA; 5'-Phosphate, 3'-dTdT overhang |
| si-Fas (6 MM) | 328798 | Fas | as (6 MM) | 5'-P GUGUCGUGUUCAGUUCCAC dTdT | 32 | unmodified RNA; 5'-Phosphate, 3'-dTdT overhang |
| | 328799 | Fas | s (6 MM) | 5'-P GUGGAACUGAACACGACAC dTdT | 33 | unmodified RNA; 5'-Phosphate, 3'-dTdT overhang |

†siRNAs are named as dsRNA sets (e.g., si-PTEN includes the antisense strand 263186 and sense strand 263187)
‡si-Fas sequences from Song et. al. (2003)
Legend: as - antisense strand, s - sense strand, ApoB - Apolipoprotein B, PTEN - Phosphotase and Tensin homolog deleted on chromosome Ten, MTTP - Microsomal Triglyceride Transfer Protein

TABLE 13

| | 0 | 1 | 2 | 4 | % UTC |
|---|---|---|---|---|---|
| A | 303912 | | | add 341315 (4 uM) | 130 |
| B | 303912 | replace with 341315 (replaced with 303912 instead by mistake) | | | 105 |
| C | 303912 | | replace with 341315 | | 104 |
| D | 303912 | | | replace with 341315 | 94 |
| E | 316449 | | | add 341315 (4 uM) | 141 |
| F | 316449 | replace with 341315 | | | 103 |
| G | 316449 | | replace with 341315 | | 107 |
| H | 316449 | | | replace with 341315 | 114 |
| I | 341315 | | | add 303912 (4 uM) | 31 |
| J | 341315 | replace with 303912 | | | 122 |
| K | 341315 | | replace with 303912 | | 23 |
| L | 341315 | | | replace with 303912 | 29 |
| M | 341315 | | | add 316449 (4 uM) | 50 |
| N | 341315 | replace with 316449 | | | 120 |
| O | 341315 | | replace with 316449 | | 42 |
| P | 341315 | | | replace with 316449 | 50 |
| Q | 303912:341315 | | | | 31 |
| R | 316449:341315 | | | | 68 |
| S | 303912 | | | | 82 |
| T | 316449 | | | | 89 |
| U | 347849:308746 | | | | 83 |

A, E, I & M - cells were treated at time 0 with one strand; after four hours, the other strand was added.

B, F, J & N - cells were treated at time 0 with one strand; after 1 hour, the first treatment is removed and replaced with the one containing the other strand.

C, G, K & O - cells were treated at time 0 with one strand; after 2 hours, the first treatment is removed and replaced with the one containing the other strand.

D, H, L & P - cells were treated at time 0 with one strand; after 4 hours, the first treatment is removed and replaced with the one containing the other strand.

Q-U - these were treated at time 0 and left untouched until lysis time.

TABLE 14

Free Uptake in mouse hepatocytes-effects of chemical modifications

| | Time (hr) | | | | |
|---|---|---|---|---|---|
| | 0 | 1 | 2 | 4 | % UTC |
| A | 344178 | | | add 303912 (2 uM) | 45 |
| B | 344178 | replace with 303912 | | | 28 |
| C | 344178 | | replace with 303912 | | 41 |
| D | 344178 | | | replace with 303912 | 43 |
| E | 344178 | | | add 317502 (2 uM) | 50 |
| F | 344178 | replace with 317502 | | | 40 |
| G | 344178 | | replace with 317502 | | 66 |
| H | 344178 | | | replace with 317502 | 73 |
| I | 344178 | | | add 335449 (2 uM) | 89 |
| J | 344178 | replace with 335449 | | | 79 |
| K | 344178 | | replace with 335449 | | 82 |
| L | 344178 | | | replace with 335449 | 82 |
| M | 344178 | | | add 354626 (2 uM) | 49 |
| N | 344178 | replace with 354626 | | | 29 |
| O | 344178 | | replace with 354626 | | 45 |
| P | 344178 | | | replace with 354626 | 47 |
| Q | 354622 | | | add 303912 (2 uM) | 98 |
| R | 354622 | replace with 303912 | | | 86 |
| S | 354622 | | replace with 303912 | | 88 |
| T | 354622 | | | replace with 303912 | 94 |
| U | 303912 | | | | 95 |
| V | 317502 | | | | 122 |
| W | 354626 | | | | 96 |
| X | 116847 | | | | 7 |
| Y | 303912:344178 | | | | 23 |
| Z | 354626:344178 | | | | 23 |

A, E, I, M and Q - cells were treated at time 0 with one strand; after four hours, the other strand was added.

B, F, J, N and R - cells were treated at time 0 with one strand; after 1 hour, the first treatment is removed and replaced with the one containing the other strand.

C, G, K, O and S - cells were treated at time 0 with one strand; after 2 hours, the first treatment is removed and replaced with the one containing the other strand.

D, H, L, P and T - cells were treated at time 0 with one strand; after 4 hours, the first treatment is removed and replaced with the one containing the other strand.

U, V, W, X, Y and Z - these were treated at time 0 and left untouched until lysis time.

TABLE 15

Free Uptake in mouse hepatocytes-effects of backbone modifications

| | Time (hr) | | | | |
|---|---|---|---|---|---|
| | 0 | 1 | 2 | 4 | % UTC |
| A | 330696 | | | add 303912 (2 µM) | ND |
| B | 330696 | replace with 303912 | | | ND |
| C | 330696 | | replace with 303912 | | ND |
| D | 330696 | | | replace with 303912 | ND |
| E | 330696 | | | add 335449 (2 µM) | 84 |
| F | 330696 | replace with 335449 | | | 86 |
| G | 330696 | | replace with 335449 | | 85 |
| H | 330696 | | | replace with 335449 | 104 |
| I | 341315 | | | add 303912 (2 µM) | ND |
| J | 341315 | replace with 303912 | | | 24 |
| K | 341315 | | replace with 303912 | | 27 |
| L | 341315 | | | replace with 303912 | 32 |
| M | 341315 | | | add 317502 (2 µM) | 79 |
| N | 341315 | replace with 317502 | | | 52 |
| O | 341315 | | replace with 317502 | | 69 |
| P | 341315 | | | replace with 317502 | 97 |
| Q | 341315 | | | add 335449 (2 µM) | 96 |
| R | 341315 | replace with 335449 | | | 89 |
| S | 341315 | | replace with 335449 | | 94 |
| T | 341315 | | | replace with 335449 | 105 |
| U | 341315 | | | add 354626 (2 µM) | 35 |

TABLE 15-continued

Free Uptake in mouse hepatocytes-effects of backbone modifications

| | Time (hr) | | | | |
|---|---|---|---|---|---|
| | 0 | 1 | 2 | 4 | % UTC |
| V | 341315 | replace with 354626 | | | 29 |
| W | 341315 | | replace with 354626 | | 37 |
| X | 341315 | | | replace with 354626 | 39 |
| Y | 354626:341315 | | | | 34 |
| Z | 116847 | | | | 9 |

A, E, I, M, Q and U - cells were treated at time 0 with one strand; after four hours, the other strand was added.
B, F, J, N, R and V - cells were treated at time 0 with one strand; after 1 hour, the first treatment is removed and replaced with the one containing the other strand.
C, G, K, O, S and W - cells were treated at time 0 with one strand; after 2 hours, the first treatment is removed and replaced with the one containing the other strand.
D, H, L, P, T and X - cells were treated at time 0 with one strand; after 4 hours, the first treatment is removed and replaced with the one containing the other strand.
Y and Z - these were treated at time 0 and left untouched until lysis time.

TABLE 16

MOE in Both Strands Improves Activity

| Compound (sense_antisense) | Construct (sense 5' to 3'/antisense) | IC$_{50}$ (nM) | Efficacy (% UTC) |
|---|---|---|---|
| Unmodified sense/antisense | P-5'-AAGUAAGGACCAGAGACAA-3' (SEQ ID NO: 35) 3'-UUCAUUCCUGGUCUCUGUUU-5'-P (SEQ ID NO: 38) | 2.8 | 17 |
| Unmodified sense/MOE modified antisense | P-5'-AAGUAAGGACCAGAGACAA-3' (SEQ ID NO: 35) 3'-UUCAUUCCUGGUCUCUGUUU-5'-P (SEQ ID NO: 38) | <0.1 | 17 |
| Modified sense & antisense | P-5'-AAGUAAGGACCAGAGACAA-3' (SEQ ID NO: 35) 3'-UUCAUUCCUGGUCUCUGUUU-5'-P (SEQ ID NO: 38) | 0.9 | 20 | bolded nucleotides indicated point of modification.

TABLE 17

MOE Gapmer Sense Strands Enhance Potentcy of siRNA Duplexes

| Compound | Construct (Sense 5' to 3'/Antisense) | IC$_{50}$ (nM) | Efficacy (% UTC) |
|---|---|---|---|
| Unmodified | 5'-AAGUAAGGACCAGAGACAA-3' (SEQ ID NO: 35) 3'-UUCAUUCCUGGUCUCUGUU-5' (SEQ ID NO: 38) | 0.9 | 14 |
| MOE gapmer sense Unmodified antisense | 5'-AAGUAAGGACCAGAGACAA-3' (SEQ ID NO: 35) 3'-UUCAUUCCUGGUCUCUGUU-5' (SEQ ID NO: 38) | 0.5 | 13 |
| Unmodified sense 4'-thio gap-mer antisense | 5'-AAGUAAGGACCAGAGACAA-3' (SEQ ID NO: 35) 3'-UUCAUUCCUGGUCUCUGUU-5' (SEQ ID NO: 38) | 5.0 | 18 |
| MOE gapmer sense 4'-thio gap-mer antisense | 5'-AAGUAAGGACCAGAGACAA-3' (SEQ ID NO: 35) 3'-UUCAUUCCUGGUCUCUGUU-5' (SEQ ID NO: 38) | 0.5 | 15 |

TABLE 17-continued

MOE Gapmer Sense Strands Enhance Potentcy of siRNA Duplexes

| Compound | Construct (Sense 5' to 3'/Antisense) | IC$_{50}$ (nM) | Efficacy (% UTC) |
|---|---|---|---|
| Unmodified sense OME/4'-thio gap antisense | 5'-AAGUAAGGACCAGAGACAA-3' (SEQ ID NO: 35) 3'-UUCAUUCCUGGUCUCUGUU-5' (SEQ ID NO: 38) | 0.7 | 15 |
| MOE gapmer sense OMe/4'-thio gap antisense | 5'-AAGUAAGGACCAGAGACAA-3' (SEQ ID NO: 35) 3'-UUCAUUCCUGGUCUCUGUU-5' (SEQ ID NO: 38) | 0.2 | 11 | bolded nucleotides indicated point of modification.

TABLE 18

Human PTEN Modified siRNA in HeLa Cells - Normalized to Riboqreen

| # | Sense_Antisense | |
|---|---|---|
| 1 | 5'-AAGUAAGGACCAGAGACAA-3' (SEQ ID NO: 35) 3'-UUCAUUCCUGGUCUCUGUU-5' (SEQ ID NO: 40) | |
| 2 | P-5'-AAGUAAGGACCAGAGACAA-3' (SEQ ID NO: 35) 3'-UUCAUUCCGUGGUCUCUGUU-5' (SEQ ID NO: 40) | MOE MOE |
| 3 | P-5'-AAGUAAGGACCAGAGACAA-3' (SEQ ID NO: 35) 3'-UUCAUUCCUGGUCUCUGUU-5' (SEQ ID NO: 40) | OMe OMe |
| 4 | 5'-AAGUAAGGACCAGAGACAA-3' (SEQ ID NO: 35) 3'-UUCAUUCCUGGUCUCUGUU-5' (SEQ ID NO: 40) | MOE |
| 5 | 5'-AAGUAAGGACCAGAGACAA-3' (SEQ ID NO: 35) 3'-UUCAUUCCUGGUCUCUGUU-5' (SEQ ID NO: 40) | MOE |

TABLE 18-continued

Human PTEN Modified siRNA in HeLa Cells - Normalized to Ribogreen

| # | Sense_Antisense | |
|---|---|---|
| 6 | 5'-AAGUAAGGACCAGAGACAA-3' (SEQ ID NO: 35)<br>3'-UUCAUUCCUGGUCUCUGUU-5' (SEQ ID NO: 40) | MOE<br>OMe |
| 7 | 5'-AAGUAAGGACCAGAGACAA-3' (SEQ ID NO: 35)<br>3'-UUCAUUCCUGGUCUCUGUU-5' (SEQ ID NO: 40) | MOE<br>OMe |
| 8 | 5'-AAGUAAGGACCAGAGACAA-3' (SEQ ID NO: 35)<br>3'-UUCAUUCCUGGUCUCUGUU-5' (SEQ ID NO: 40) | OMe<br>OMe |
| 9 | P-5'-AAGUAAGGACCAGAGACAA-3' (SEQ ID NO: 35)<br>3'-UUCAUUCCUGGUCUCUGUU-5' (SEQ ID NO: 40) | MOE<br>OMe |

TABLE 19

Human PTEN Sense Strand 4'-Thioribose

| # | Sense_Antisense, 5'_3' | IC₅₀ nM | Efficacy % UTC |
|---|---|---|---|
| 1 | AAGUAAGGACCAGAGACACAA-3' (SEQ ID NO: 39)<br>UUCAUUCCUGGUCUCUGUUU-5' (SEQ ID NO: 38) | 0.4 | 10 |
| 2 | AAGUAAGGACCAGAGACAA-3' (SEQ ID NO: 35)<br>UUCAUUCCUGGUCUCUGUU-5' (SEQ ID NO: 40) | 1.0 | 20 |
| 3 | AAGUAAGGACCAGAGACAAA-3' (SEQ ID NO: 39)<br>uucAUUCCUGGUCUCUGUUU-5' (SEQ ID NO: 38) | 1.9 | 10 |
| 4 | AAGUAAGGACCAGAGACAAA-3' (SEQ ID NO: 39)<br>UUCAUUCCUGGUCUCUGUUU-5' (SEQ ID NO: 38) | 1.7 | 20 |
| 5 | AAGUAAGGACCAGAGACAAA-3' (SEQ ID NO: 39)<br><u>UUC</u>AUUCCUGGUC<u>UC</u>UGU<u>UU</u>-5' (SEQ ID NO: 38) | 2.4 | 20 |
| 6 | AAGUAAGGACCAGAGACAAA-3' (SEQ ID NO: 39)<br>UUCAUUCCUGGUCUCUGUUU-5' (SEQ ID NO: 38) | 1.0 | 20 |
| 7 | AAGUAAGGACCAGAGACAAA-3' (SEQ ID NO: 39)<br>UUCAUUCCUGGUCUCUGUUU-5' (SEQ ID NO: 38) | 0.3 | 10 |
| 8 | AAGUAAGGACCAGAGACAAA-3' (SEQ ID NO: 39)<br>UUCAUUCCUGGUCUCUGUUU-5' (SEQ ID NO: 38) | 0.2 | 10 |
| 9 | AAGUAAGGACCAGAGACAAA-3' (SEQ ID NO: 39)<br>uucAUUCCUGGUCUCUGUUU-5' (SEQ ID NO: 38) | <0.1 | 10 |

TABLE 19-continued

Human PTEN Sense Strand 4'-Thioribose

| # | Sense_Antisense, 5'_3' | IC₅₀ nM | Efficacy % UTC |
|---|---|---|---|
| 10 | AAGUAAGGACCAGAGACAAA-3' (SEQ ID NO: 39)<br><u>UUC</u>AUUCCUGGUCUCUGU<u>UU</u>-5' (SEQ ID NO: 38) | 1.4 | 20 | bolded nucleotides = 4'-thio; small letter nucleotides = OMe

TABLE 20

In Vivo Constructs

| Compound (Sense_anti-sense) | Construct (Sense 5'→3'/Antisense) | Target |
|---|---|---|
| 341401_341391 | 5'-AAGUAAGGACCAGAGACAA-3' P0 (SEQ ID NO: 35)<br>3'-UUCAUUCCUGGUCUCUGUU-5' (SEQ ID NO: 40) | PTEN |
| 359551_359550 | 5'-A₅AG₅UA₅AG₅GA₅CC₅AG₅AG₅AC₅AA-3' P0/PS (SEQ ID NO: 35)<br>3'-UU₅CA₅UU₅CC₅UG₅UC₅UC₅UG₅U-5' (SEQ ID NO: 40) | PTEN |
| 352821_352820 | 5'-AaGuAaGgAcCaGaGaCaA-3' OMe/F* P0 (SEQ ID NO: 35)<br>3'-uUcAuUcCuGgUcUcUgUu-5' (SEQ ID NO: 40) | PTEN |
| 308746_342851 | 5'-AAGUAAGGACGAGAGACAAA-3' (20-mer)(SEQ ID NO: 35)<br>3'-UUCAUUCCUGGUCUCUGUUU-5' (SEQ ID NO: 40)<br>4' Thio P0 | PTEN |

*small letter nucleotides = OMe; bolded nucleotides = F

TABLE 21

Concentration of PTEN siRNA Constructs in Mice

| Dose group I.D. | (+)RNA:(−)RNA | URINE (nmoles/l urine) | KIDNEY (nmoles/kg kidney) | LIVER (nmoles/kg liver) |
|---|---|---|---|---|
| D | 308746:361779 | 180:160 | <20:<20* | <20:<20* |
| F | 341401:341391 | <20:<20* | <20:<20* | <20:<20* |
| H | 359551:359550 | 4,000:400 | <20:<20* | 20:100 |

TABLE 22

In Vitro Analysis of Cholesterol Conjugates

| # | Sense Antisense | SEQ ID NO. |
|---|---|---|
| 341401 | 5'-AAGUAAGGACCAGAGACAA-3' | 35 |
| 341391 | 3'-UUCAUUCCUGGUCUCUGUU-5' | 40 |
| 366559 | AAGUAAGGACCAGAGACAA-3'chol | 35 |
| 341391 | UUCAUUCCUGGUCUCUGUU-5' | 40 |
| 366559 | AAGUAAGGACCAGAGACAA-3'chol | 35 |
| 359995 | uUcAuUcCuGgUcUcUgUu-5' | 40 |
| 366667 | 5'chol-AaGuAaGgAcCaGaGaCaA | 35 |
| 341391 | 3'-     UUCAUUCCUGGUCUCUGUU | 40 |

TABLE 22-continued

In Vitro Analysis of Cholesterol Conjugates

| # | Sense_Antisense | SEQ ID NO. |
|---|---|---|
| 359467 | 5'-        AAGUAAGGACCAGAGACAA | 35 |
| 366561 | 3'chol-uUcAuUcCuGgUcUcUgUu | 40 |
| | | |
| 341401 | 5'-        AAGUAAGGACCAGAGACAA | 35 |
| 366561 | 3'chol-uUcAuUcCuGgUcUcUgUu | 40 |

*small letter nucleotides = OMe; bolded nucleotides = F

TABLE 23

In Vitro Analysis of Cholesterol Conjugates

| # | Sense_Antisense | SEQ ID NO. |
|---|---|---|
| 359996 | 5'-AaGuAaGgAcCaGaGaCaA-3' | 35 |
| 359995 | 3'-uUcAuUcCuGgUcUcUgUu-5' | 40 |
| | | |
| 366667 | 5'chol-AaGuAaGgAcCaGaGaCaA | 35 |
| 359995 | 3'-   uUcAuUcCuGgUcUcUgUu | 40 |
| | | |
| 366667 | 5'chol-AaGuAaGgAcCaGaGaCaA | 35 |
| 352820 | 3'-   uUcAuUcCuCgUcUcUgUu-P | 40 |
| | | |
| 359996 | 5'-     AaGuAaGgAcCaGaGaCaA | 35 |
| 366561 | 3'-chol uUcAuUcCuGgUcUcUgUu | 40 |
| | | |
| 344178 | 5'-<u>AAGUAAGGACCAGAGACAAA</u> | 39 |
| 303912 | 3'-<u>UUCAUUCCUGGUGUCUGUUA</u> | 41 |
| | | |
| 29592 | 3'-<u>T*T*C*A*TTCCTGGTCTC*T*G*T*</u>-5' | 42 |

*small letter nucleotides = OMe; bolded nucleotides = F; * = MOE

TABLE 24

In Vitro Analysis of Cholesterol Conjugates

| # | Sense_Antisense | SEQ ID NO. |
|---|---|---|
| 341401 | 5'-AAGUAAGGACCAGAGACAA-3' | 35 |
| 341391 | 3'-UUCAUUCCUGGUCUCUGUU-5' | 40 |
| | | |
| 366559 | AAGUAAGGACGAGAGACAA-3' chol | 35 |

TABLE 24-continued

In Vitro Analysis of Cholesterol Conjugates

| # | Sense_Antisense | SEQ ID NO. |
|---|---|---|
| 341391 | UUCAUUCCUGGUCUCUGUU-5' | 40 |
| | | |
| 366559 | AAGUAAGGACCAGAGACAA-3' chol | 35 |
| 359995 | uUcAuUcCuGgUcUcUgUu-5' | 40 |
| | | |
| 366667 | 5' chol-AaGuAaGgAcCaGaGaCaA | 35 |
| 341391 | 3'-     UUCAUUCCUGGUCUCUGUU | 40 |
| | | |
| 359467 | 5'-     <u>AAGUAAGGACCAGAGACAA</u> | 35 |
| 366561 | 3' chol-uUcAuUcCuGgUcUcUgUu | 40 |
| | | |
| 341401 | 5'-     AAGUAAGGACCAGAGACAA | 35 |
| 366561 | 3' chol-uUcAuUcCuGgUcUcUgUu | 40 |

*small letter nucleotides = OMe; bolded nucleotides = F

TABLE 25

In Vitro Analysis of Cholesterol Conjugates

| # | Sense_Antisense | SEQ ID NO. |
|---|---|---|
| 359996 | 5'-AaGuAaGgAcCaGaGaCaA-3' | 35 |
| 359995 | 3'-uUcAuUcCuGgUcUcUgUu-5' | 40 |
| | | |
| 366667 | 5'chol-AaGuAaGgAcCaGaGaCaA | 35 |
| 359995 | 3'-   uUcAuUcCuGgUcUcUgUu | 40 |
| | | |
| 366667 | 5'chol-AaGuAaGgAcCaGaGaCaA | 35 |
| 352820 | 3'-   uUcAuUcCuGgUcUcUgUu-P | 40 |
| | | |
| 359996 | 5'-     AaGuAaGgAcCaGaGaCaA | 35 |
| 366561 | 3'-chol-uUcAuUcCuGgUcUcUgUu | 40 |
| | | |
| 344178 | 5'-<u>AAGUAAGGACCAGAGACAAA</u> | 35 |
| 303912 | 3'-<u>UUCAUUCCUGGUCUCUGUUA</u> | 40 |
| | | |
| 29592 | 3'-<u>T*T*C*A*TTCCTGGTCTC*T*G*T*</u>-5' | 42 |

*small letter nucleotides = OMe; bolded nucleotides = F; * = MOE

TABLE 26

In Vitro mRNA and Protein Reduction Results with Target X Chemistries

| Compound | Construct (Sense 5'→3'/Antisense) | $IC_{50}$ (nM) | Efficacy (% UTC) | Protein $IC_{50}$ (nM) | Stability $t\frac{1}{2}$ (h) |
|---|---|---|---|---|---|
| siRNA 1 | XXXXXXXXXXXXXXXXXXXX XXXXXXXXXXXXXXXXXXXX | 0.60 | 14 | <1.0 | <1 |
| siRNA 2 | XXXXXXXXXXXXXXXXXXXX X†X†X†XXXXXXXXXXXXXX†X†X† | 0.2 | 26 | <1.0 | >4 |
| siRNA 3 | XX*XX*XX*XX*XX*XX*XX*XX*X xxxXXXXXxxXXxxXXXXX | .12 | 8 | 2.9 | >4 |
| siRNA 4 | XxXxXxXxXxXxXxXxXxX xXxXxXxXxXxXxXxXxXx | 0.06 | 8 | 4.0 | >4 |

*small letter nucleotides = OMe;
bolded nucleotides = F;
*= MOE;
†= 4'-Thio

What is claimed is:

1. A method for reducing the level of target mRNA in a cell comprising:
    contacting the cell with a single-stranded sense oligonucleotide consisting of 10 to 40 linked nucleosides; and
    contacting the cell with a single-stranded antisense oligonucleotide consisting of 10 to 40 linked nucleosides at least one hour after contacting the cell with the sense oligonucleotide;
    wherein the antisense oligonucleotide is complementary to the target mRNA, the sense and antisense oligonucleotides are fully complementary to each other, the contacting occurs in the absence of a transfection reagent, and the sense oligonucleotide is a symmetric gapped oligomeric compound comprising
    a 5' region consisting of three to five 2'-O—(CH$_2$)$_2$—OCH$_3$ modified nucleosides;
    a central region consisting of nine to twenty β-D-ribonucleosides; and
    a 3' region consisting of three to five 2'-O—(CH$_2$)$_2$—OCH$_3$ modified nucleosides; and
thereby reducing the level of target mRNA in the cell.

2. The method of claim 1, wherein the cell is a rodent primary hepatocyte or a primate primary hepatocyte.

3. The method of claim 1 wherein the cell is a mammalian tissue-derived cell.

4. The method of claim 1 wherein the cell is contacted with the antisense oligonucleotide at least two hours after the cell is contacted with the sense oligonucleotide.

5. The method of claim 1 wherein each of the nucleosides of the antisense oligonucleotide comprises a β-D-ribofuranose sugar group.

6. The method of claim 1 wherein the 3'-terminus of at least one of the sense and antisense oligonucleotides, independently, comprises a stabilizing or conjugate group.

7. The method of claim 6 wherein the stabilizing group is a capping group or a dTdT dimer.

8. The method of claim 1 wherein at least one of the sense and antisense oligonucleotides comprises a 5'-phosphate group.

9. The method of claim 1 wherein the 5'-terminus of at least one of the sense and antisense oligonucleotides, independently, comprises a stabilizing or conjugate group.

10. The method of claim 9 wherein the stabilizing group is a capping group.

11. The method of claim 1 wherein each of the internucleoside linking groups of at least one of the sense oligonucleotide and the antisense oligonucleotide is, independently, a phosphorothioate.

12. The method of claim 1 wherein the sense and antisense oligonucleotides are capable of hybridizing to form a duplex having 3'-dTdT overhangs.

13. The method of claim 1 wherein the sense and antisense oligonucleotides are capable of hybridizing to form a duplex having blunt ends.

14. The method of claim 1 wherein at least one of the sense and antisense oligonucleotides comprises at least one terminal cap moiety.

15. The method of claim 14 wherein the terminal cap moiety is attached to one or both of the 3'-terminal and 5'-terminal ends of the at least one oligonucleotide.

16. The method of claim 14 wherein the terminal cap moiety is an inverted deoxy abasic moiety.

17. The method of claim 1 wherein the antisense oligonucleotide comprises a 2'-substituent selected from the group consisting of —F, —O—CH$_2$CH$_2$—O—CH$_3$, —O—CH$_3$, —O—CH$_2$—CH=CH$_2$ or —O—CH$_2$—CH—CH$_2$—NH (R$_j$), where R$_j$ is H or C$_1$-C$_{10}$ alkyl.

* * * * *

SEQUENCE LISTING

<160> NUMBER OF SEQ ID NOS: 42

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
atgacaatca tgttgcagca attc                                          24

<210> SEQ ID NO 2
<211> LENGTH: 25
<212> TYPE: DNA
<213> ORGANISM: Artificial Sequence
<220> FEATURE:
<223> OTHER INFORMATION: Primer

<400> SEQUENCE: 2
cgatgcaata aatatgcaca aatca                                         25

<210> SEQ ID NO 3
<211> LENGTH: 26
<212> TYPE: DNA
<213> ORGANISM: Artificial Sequence
<220> FEATURE:
<223> OTHER INFORMATION: Probe

<400> SEQUENCE: 3
gtaaagctgg aaagggacgg actggt                                        26

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
tccaagacac agctgagcag a                                             21

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
tgcatcactc ttcccatgag at                                            22

<210> SEQ ID NO 6
<211> LENGTH: 26
<212> TYPE: DNA
<213> ORGANISM: Artificial Sequence
<220> FEATURE:
<223> OTHER INFORMATION: Probe

<400> SEQUENCE: 6
agtccagctg ctcctgtgct ggtacc                                        26

<210> SEQ ID NO 7
<211> LENGTH: 19

```
<212> TYPE: DNA
<213> ORGANISM: Artificial Sequence
<220> FEATURE:
<223> OTHER INFORMATION: Primer

<400> SEQUENCE: 7
cgtgggctcc agcattcta                                                    19

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
agtcatttct gcctttgcgt c                                                 21

<210> SEQ ID NO 9
<211> LENGTH: 22
<212> TYPE: DNA
<213> ORGANISM: Artificial Sequence
<220> FEATURE:
<223> OTHER INFORMATION: Probe

<400> SEQUENCE: 9
ccaatggtcg ggcactgctc aa                                                22

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
gagcggtctg gatttacaac g                                                 21

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
aggtagtgac agatgtggct tttg                                              24

<210> SEQ ID NO 12
<211> LENGTH: 23
<212> TYPE: DNA
<213> ORGANISM: Artificial Sequence
<220> FEATURE:
<223> OTHER INFORMATION: Probe

<400> SEQUENCE: 12
caaaccaggt gctgggcgtc agt                                               23

<210> SEQ ID NO 13
<211> LENGTH: 15
<212> TYPE: DNA
<213> ORGANISM: Artificial Sequence
<220> FEATURE:
<223> OTHER INFORMATION: Primer

<400> SEQUENCE: 13
```

```
tcgccgcttg ctgca                                                    15
```

<210> SEQ ID NO 14
<211> LENGTH: 17
<212> TYPE: DNA
<213> ORGANISM: Artificial Sequence
<220> FEATURE:
<223> OTHER INFORMATION: Primer

<400> SEQUENCE: 14

```
atcggccgtg atgtcga                                                  17
```

<210> SEQ ID NO 15
<211> LENGTH: 23
<212> TYPE: DNA
<213> ORGANISM: Artificial Sequence
<220> FEATURE:
<223> OTHER INFORMATION: Probe

<400> SEQUENCE: 15

```
ccatggtcaa ccccaccgtg ttc                                           23
```

<210> SEQ ID NO 16
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 16

```
ctgctagcct ctggatttga                                               20
```

<210> SEQ ID NO 17
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 17

```
cttctggcat ccggtttaga                                               20
```

<210> SEQ ID NO 18
<211> LENGTH: 12
<212> TYPE: RNA
<213> ORGANISM: Artificial Sequence
<220> FEATURE:
<223> OTHER INFORMATION: Oligomeric Compound

<400> SEQUENCE: 18

```
cgcgaauucg cg                                                       12
```

<210> SEQ ID NO 19
<211> LENGTH: 12
<212> TYPE: RNA
<213> ORGANISM: Artificial Sequence
<220> FEATURE:
<223> OTHER INFORMATION: Oligomeric Compound

<400> SEQUENCE: 19

```
gcgcuuaagc gc                                                       12
```

<210> SEQ ID NO 20
<211> LENGTH: 20
<212> TYPE: DNA
<213> ORGANISM: Artificial Sequence

```
<220> FEATURE:
<223> OTHER INFORMATION: Oligomeric Compound

<400> SEQUENCE: 20
tccagcactt tcttttccgg                                               20

<210> SEQ ID NO 21
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 21
tccatctcct tttatgccgg                                               20

<210> SEQ ID NO 22
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 22
cccagcacct ggtttgccgt                                               20

<210> SEQ ID NO 23
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 23
gtccctgaag atgtcaatgc                                               20

<210> SEQ ID NO 24
<211> LENGTH: 21
<212> TYPE: DNA
<213> ORGANISM: Artificial Sequence
<220> FEATURE:
<223> OTHER INFORMATION: Oligomeric Compound

<400> SEQUENCE: 24
cugcuagccu cuggauuugt t                                             21

<210> SEQ ID NO 25
<211> LENGTH: 21
<212> TYPE: DNA
<213> ORGANISM: Artificial Sequence
<220> FEATURE:
<223> OTHER INFORMATION: Oligomeric Compound

<400> SEQUENCE: 25
caaauccaga ggcuagcagt t                                             21

<210> SEQ ID NO 26
<211> LENGTH: 21
<212> TYPE: DNA
<213> ORGANISM: Artificial Sequence
<220> FEATURE:
<223> OTHER INFORMATION: Oligomeric Compound

<400> SEQUENCE: 26
cuucuggcau ccgguuuagt t                                             21
```

<210> SEQ ID NO 27
<211> LENGTH: 21
<212> TYPE: DNA
<213> ORGANISM: Artificial Sequence
<220> FEATURE:
<223> OTHER INFORMATION: Oligomeric Compound

<400> SEQUENCE: 27
cuaaaccgga ugccagaagt t                                             21

<210> SEQ ID NO 28
<211> LENGTH: 21
<212> TYPE: RNA
<213> ORGANISM: Artificial Sequence
<220> FEATURE:
<223> OTHER INFORMATION: Oligomeric Compound

<400> SEQUENCE: 28
cugcuagccu cuggauuuga c                                             21

<210> SEQ ID NO 29
<211> LENGTH: 21
<212> TYPE: RNA
<213> ORGANISM: Artificial Sequence
<220> FEATURE:
<223> OTHER INFORMATION: Oligomeric Compound

<400> SEQUENCE: 29
gucaaaucca gaggcuagca g                                             21

<210> SEQ ID NO 30
<211> LENGTH: 21
<212> TYPE: DNA
<213> ORGANISM: Artificial Sequence
<220> FEATURE:
<223> OTHER INFORMATION: Oligomeric Compound

<400> SEQUENCE: 30
gucugguuug cacuugcact t                                             21

<210> SEQ ID NO 31
<211> LENGTH: 21
<212> TYPE: DNA
<213> ORGANISM: Artificial Sequence
<220> FEATURE:
<223> OTHER INFORMATION: Oligomeric Compound

<400> SEQUENCE: 31
gugcaagugc aaaccagact t                                             21

<210> SEQ ID NO 32
<211> LENGTH: 21
<212> TYPE: DNA
<213> ORGANISM: Artificial Sequence
<220> FEATURE:
<223> OTHER INFORMATION: Oligomeric Compound

<400> SEQUENCE: 32
gugucguguu caguccact t                                              21

<210> SEQ ID NO 33
<211> LENGTH: 21
<212> TYPE: DNA
<213> ORGANISM: Artificial Sequence
<220> FEATURE:
<223> OTHER INFORMATION: Oligomeric Compound

<400> SEQUENCE: 33
guggaacuga acacgacact t                                              21

<210> SEQ ID NO 34
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 34
tttgtctctg gtccttactt                                                20

<210> SEQ ID NO 35
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 35
aaguaaggac cagagacaa                                                 19

<210> SEQ ID NO 36
<211> LENGTH: 21
<212> TYPE: DNA
<213> ORGANISM: Artificial Sequence
<220> FEATURE:
<223> OTHER INFORMATION: Oligomeric Compound

<400> SEQUENCE: 36
tttgtctctg gtccttactt t                                              21

<210> SEQ ID NO 37
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 37
aagtaaggac cagagacaaa                                                20

<210> SEQ ID NO 38
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 38
uucauuccug gucucuguuu                                                20

<210> SEQ ID NO 39
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 39
aaguaaggac cagagacaaa                                                20

<210> SEQ ID NO 40

-continued

```
<211> LENGTH: 19
<212> TYPE: RNA
<213> ORGANISM: Artificial Sequence
<220> FEATURE:
<223> OTHER INFORMATION: Oligomeric Compound

<400> SEQUENCE: 40
uucauuccug gucucuguu                                                   19

<210> SEQ ID NO 41
<211> LENGTH: 20
<212> TYPE: RNA
<213> ORGANISM: Artificial Sequence
<220> FEATURE:
<223> OTHER INFORMATION: Oligomeric Compound

<400> SEQUENCE: 41
uucauuccug gucucuguua                                                  20

<210> SEQ ID NO 42
<211> LENGTH: 18
<212> TYPE: DNA
<213> ORGANISM: Artificial Sequence
<220> FEATURE:
<223> OTHER INFORMATION: Oligomeric Compound

<400> SEQUENCE: 42
ttcattcctg gtctctgt                                                    18
```